(12) United States Patent
Bolli et al.

(10) Patent No.: US 8,410,151 B2
(45) Date of Patent: Apr. 2, 2013

(54) AMINOMETHYL BENZENE DERIVATIVES

(75) Inventors: Martin Bolli, Allschwil (CH); Cyrille Lescop, Kembs (FR); Boris Mathys, Pratteln (CH); Claus Mueller, Weil am Rhein (DE); Oliver Nayler, Arlesheim (CH); Beat Steiner, Dornach (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

(21) Appl. No.: 12/920,574

(22) PCT Filed: Mar. 3, 2009

(86) PCT No.: PCT/IB2009/050844
§ 371 (c)(1),
(2), (4) Date: Oct. 6, 2010

(87) PCT Pub. No.: WO2009/109904
PCT Pub. Date: Sep. 11, 2009

(65) Prior Publication Data
US 2011/0028449 A1   Feb. 3, 2011

(51) Int. Cl.
*A61K 31/4245* (2006.01)
*C07D 271/06* (2006.01)

(52) U.S. Cl. ........................ 514/364; 548/131
(58) Field of Classification Search ............... 514/364; 548/131
See application file for complete search history.

(56) References Cited

U.S. PATENT DOCUMENTS

| | | | |
|---|---|---|---|
| 6,090,804 A | 7/2000 | Kimura et al. | |
| 7,834,039 B2 * | 11/2010 | Hobson et al. | 514/364 |
| 8,003,800 B2 | 8/2011 | Bolli et al. | |
| 8,133,910 B2 | 3/2012 | Bolli et al. | |
| 8,148,410 B2 | 4/2012 | Bolli et al. | |
| 2007/0043014 A1 | 2/2007 | Doherty et al. | |
| 2007/0270438 A1 | 11/2007 | Bhattacharya et al. | |
| 2008/0113961 A1 | 5/2008 | Nishi et al. | |
| 2008/0306124 A1 | 12/2008 | Albert et al. | |
| 2010/0063108 A1 | 3/2010 | Bolli et al. | |
| 2010/0087417 A1 | 4/2010 | Bolli et al. | |
| 2010/0087495 A1 | 4/2010 | Bolli et al. | |
| 2010/0168005 A1 | 7/2010 | Bolli et al. | |
| 2010/0234346 A1 | 9/2010 | Bolli et al. | |
| 2012/0108638 A1 | 5/2012 | Bolli et al. | |

FOREIGN PATENT DOCUMENTS

| | | |
|---|---|---|
| EP | 1873153 | 1/2008 |
| JP | 2008120794 | 5/2008 |
| WO | WO 91/15583 | 10/1991 |
| WO | WO 99/46277 | 9/1999 |
| WO | WO 01/12627 | 2/2001 |
| WO | WO 02/058695 | 8/2002 |
| WO | WO 03/062248 | 7/2003 |
| WO | WO 03/062252 | 7/2003 |
| WO | WO 2004/035538 | 4/2004 |
| WO | WO 2005/014525 | 2/2005 |
| WO | WO 2005/032465 | 4/2005 |
| WO | WO 2005/058848 | 6/2005 |
| WO | WO 2005/115382 | 12/2005 |
| WO | WO 2006/047195 | 5/2006 |
| WO | WO 2006/114400 | 11/2006 |
| WO | WO 2006/115188 | 11/2006 |
| WO | WO 2006/131336 | 12/2006 |
| WO | WO 2007/001973 | 1/2007 |
| WO | WO 2007/085451 | 8/2007 |
| WO | WO 2007/098474 | 8/2007 |
| WO | WO 2007/132307 | 11/2007 |
| WO | WO 2008/037476 | 4/2008 |
| WO | WO 2008/076356 | 6/2008 |
| WO | WO 2008/091967 | 7/2008 |
| WO | WO 2009/043889 | 4/2009 |
| WO | WO 2009/043890 | 4/2009 |
| WO | WO 2009/060278 | 5/2009 |
| WO | WO 2009/151529 | 12/2009 |
| WO | WO 2011/007324 | 1/2011 |

OTHER PUBLICATIONS

STN_preliminary search report_12920574_12142011 (2011).*
U.S. Appl. No. 12/920,656, filed Sep. 2, 2010, Bolli, et al.
U.S. Appl. No. 12/920,569, filed Sep. 1, 2010, Bolli, et al.
U.S. Appl. No. 12/920,572, filed Sep. 1, 2010, Bolli, et al.
U.S. Appl. No. 12/673,918, filed Feb. 17, 2010, Bolli, et al.
Abdel-Magid, A.F., et al., "Reductive Amination of Aldehydes and Ketones with Sodium Triacetoxyborohydride. Studies on Direct and Indirect Reductive Amination Procedures", J. Org. Chem., vol. 61, pp. 3849-3862, (1996).

(Continued)

*Primary Examiner* — Yong Chu
(74) *Attorney, Agent, or Firm* — Hoxie & Associates, LLC

(57) ABSTRACT

The invention relates to novel aminomethyl benzene derivatives, their preparation and their use as pharmaceutically active compounds. Said compounds particularly act as immunomodulating agents.

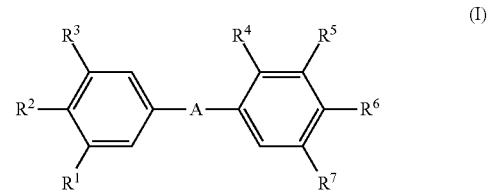

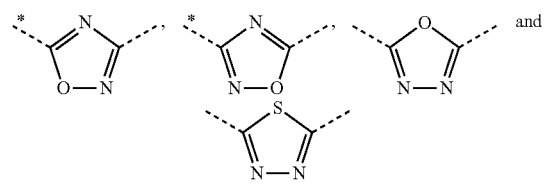

10 Claims, No Drawings

OTHER PUBLICATIONS

Battistuzzi, G., et al., "3-Arylpropanoate Esters through the Palladium-Catalyzed Reaction of Aryl Halides with Acrolein Diethyl Acetal", Synlett, vol. 8, pp. 1133-1136, (2003).

Benkeser, R.A., et al., "Additivity of Electrical Effects in Aromatic Electrophilic Substitutions as Determined by Desilylation Reactions", J. Am. Chem. Soc., vol. 80, pp. 5289-5293, (1958).

Boschelli, D.H., et al., "Synthesis and Src Kinase Inhibitory Activity of 2-Pheyl- and 2-Thienyl-7-phenylaminothieno[3,2-1Apyridine-6-carbonitriles", J. Med. Chem., vol. 48, pp. 3891-3902, (2005).

Brain, C.T., et al., "Novel procedure for the synthesis of 1,3,4-oxadiazoles from 1,2-diacylhydrazines using polymer-supported Burgess reagent under microwave conditions", Tetrahedron Lett., vol. 40, pp. 3275-3278, (1999).

Colandrea, V.J., et al., "2,5-Disubstituted Pyrrolidine Carboxylates as Potent, Orally Active Sphingosine-1-phosphate (S1P) Receptor Agonists", Bioorg. Med. Chem. Lett., vol. 16, pp. 2905-2908, (2006).

Cosmo, R., et al., "Steric Effects. Internal Rotation of 1-Aryl-8-phenylnaphthalenes", Aust. J. Chem., vol. 40, pp. 1107-1126, (1987).

Chakraborti, A.K., et al., "One-Pot Synthesis of Nitriles from Aldehydes Under Microwave Irradiation: Influence of the Medium and Mode of Microwave Irradiation on Product Formation", Tetrahedron, vol. 55, pp. 13265-13268, (1999).

Cui, J., et al., "Design and Synthesis of Highly Constrained Factor Xa Inhibitors: Amidine-Substituted Bis(benzoyl)[1,3]-diazepan-2-ones and Bis(benzylidene)-bis(gem-dimethyl)cycloketones", Biorg. Med. Chem., vol. 11, pp. 3379-3392 (2003).

Doyle, M.P., et al., "Alkyl Nitrite-Metal Halide Deamination Reactions. 2. Substitutive Deamination of Arylamines by Alkyl Nitrites and Copper (II) Halides. A Direct and Remarkably Efficient Conversion of Arylamines to Aryl Halides", J. Org. Chem., vol. 42, pp. 2426-2429, (1977).

Fei, Z., et al., "Stereo- and Regioselective Glycosylations to the Bis-C-arylglycoside of Kidamycin", Organic Letters, vol. 9, No. 18, pp. 3547-3550, (2007).

Gangloff, A.R., et al., "Synthesis of 3,5-disubstituted-1,2,4-oxadiazoles using tetrabutylammonium fluoride as a mild and efficient catalyst", Tetrahedron Lett., vol. 42, pp. 1441-1443, (2001).

Garcia, M.A., et al., "Synthesis, Biological Evaluation, and Three-Dimensional Quantitative Structure-Activity Relationship Study of Small-Molecule Positive Modulators of Adrenomedullin", J. Med. Chem., vol. 48, pp. 4068-4075, (2005).

Goswami, S., et al., "A Simple and Convenient Manganese Dioxide Oxidation of Benzyl Halides to Aromatic Aldehydes under Neutral Condition", Chemistry Letters, vol. 34, No. 2, pp. 194-195, (2005).

Gould, P.L., "Salt Selection for Basic Drugs", International Journal of Pharmaceutics, vol. 33, pp. 201-217, (1986).

Greene, T.W., et al., Protective Groups in Organic Synthesis, 2nd Edition, Wiley New York, (1991).

Hamze, A., et al., "Synthesis of Various 3-Substituted 1,2,4-Oxadiazole-Containing Chiral ã3- and r-Amino Acids from Fmoc-Protected Aspartic Acid", J. Org. Chem., vol. 68, pp. 7316-7321, (2003).

Hla, T., et al., "An Abundant Transcript Induced in Differentiating Human Endothelial Cells Encodes a Polypeptide with Structural Similarities to G-protein-coupled Receptors", Biol. Chem., vol. 265, pp. 9308-9313, (1990).

Ise, T., et al., "Syntheses, Crystal Structures, and Magnetic Properties of Nitronyl Nitroxide Triradicals Composed of Ground-State Singlet Biradicals and Monoradicals: Molecular Spin Clusters in the Crystal", Chemistry of Materials, vol. 17, pp. 4486-4492, (2005).

John, E.O., et al., "Reactions of (Difluoroamino)difluoroacetonitrile and (Difluoroamino) difluoroacetamidoxime", Inorganic Chemistry, vol. 27, pp. 3100-3104, (1988).

Kaboudin, B., et al., "One-Pot Synthesis of 1,2,4-Oxadiazoles Mediated by Microwave Irradiation Under Solvent-Free Condition", Heterocycles, vol. 60, No. 10, pp. 2287-2292, (2003).

Kende, A.S., et al., "Ring Formylation of Bromobenzoate Esters by Direct Metalation", Synthetic Communications, vol. 29, pp. 3401-3407, (1999).

Kerins, F., et al., "Generation of Substituted Styrenes via Suzuki Cross-Coupling of Aryl Halides with 2,4,6-Trivinylcyclotriboroxane", J. Org. Chem., vol. 67 pp. 4968-4971, (2002).

Kiryanov, A. A., et al., "Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis", J. Org. Chem., vol. 66, pp. 7925-7929, (2001).

Kocienski, P. J., Protecting Groups, Thieme Stuttgart, (1994).

Lu, T., et al., "Oxyguanidines. Part 2: Discovery of a Novel Orally Active Thrombin Inhibitor through Structure-Based Drug Design and Parallel Synthesis", Bioorganic & Medicinal Chemistry Letters, vol. 14, pp. 3727-3731, (2004).

Matsushita, H., et al., "Palladium-Catalyzed Reactions of Allylic Electrophiles with Organometallic Reagents. A Regioselective 1,4-Elimination and a Regio- and Stereoselective Reduction of Allylic Derivatives", J. Org. Chem., vol. 47, pp. 4161-4165, (1982).

Meyer, E., et al., "Synthesis of New 1,2,4- and 1,3,4-Oxadiazole Derivatives", Synthesis, No. 6, pp. 899-905, (2003).

Miyata, O., et al., "An Improved Synthesis of (−)-Martinellic Acid via Radical Addition-Cyclization-Elimination Reaction of Chiral Oxime Ether", Synlett, pp. 893-896, (2006).

Molina, P., et al., "An Efficient One-Pot Syntheis of Pyrrolo[4,3,2-ij]isoquinoline Derivatives by a Consecutive Aza-Wittig/Electrocyclic Ring-Closure/Intramolecular Acylation Process", Synthesis, pp. 293-296, (1992).

Narasimhan, S., et al., "Calcium Borohydride: A Reagent for Facile Conversion of Carboxylic Esters to Alcohols and Aldehydes", Synthetic Communications, vol. 25, pp. 1689-1697, (1995).

Poulain, R.F., et al. "Parallel synthesis of 1,2,4-oxadiazoles from carboxylic acids using an improved, uronium-based, activation", Tetrahedron Lett., vol. 42, pp. 1495-1498, (2001).

Remington, "The Science and Practice of Pharmacy, $21^{st}$ Edition (2005), Part 5," Pharmaceutical Manufacturing [published by Lippincott Williams & Wilkins].

Roesch, K.R., et al., "Synthesis of Isoquinolines and Pyridines by the Palladium-Catalyzed Iminoannulation of Internal Alkynes", J. Org. Chem., vol. 66, pp. 8042-8051, (2001).

Roth, B., et al., "2,4-Diamino-5-benzylpyrimidines and Analogues as Antibacterial Agents. 9. Lipophilic Trimethoprim Analogues as Antigonococcal Agents", J. Med. Chem., vol. 31, pp. 122-129, (1988).

Sawada, Y., et al., "Synthesis and Insecticidal Activity of 3,5-Dimethylbenzoyl Moiety Modified Analogues of N-tert-Butyl-N′ — (4-ethylbenzoyl)-3,5-dimethylbenzohydrazide", J. Pesticide Sci., vol. 27, pp. 365-373, (2002).

Sayigh, A.A.R., et al., "Michael Addition of Hydroxylamines to Activated Double Bonds. A Convenient Synthesis of N,N-Dialkyl Hydroxylamines", J. Org. Chem., vol. 29, pp. 2042-2043, (1964).

Sinha, S., et al., "Selective para Metalation of Unprotected 3-methoxy and 3,5-dimethoxy Benzoic Acids with n-butyl Lithium-potassium tert-butoxide (LIC-KOR): Synthesis of 3,5-dimethoxy-4-methyl benzoic Acid", Tetrahedron Letters, vol. 41, pp. 3157-3160, (2000).

Srivastava, R.M., et al., Synthesis of 3-Aryl-5-[Thien-3-Yl Methyl]-1,2,4-Oxadiazoles, Synthetic Commun., vol. 29, pp. 1437-1450, (1999).

Suzuki, T., et al., "Synthesis of the Selective 5-Hydroxytryptamine4 (5-HT$_4$) Receptor Agonist (+)-(S)-2-Chloro-5-methoxy-4-[5-(2-piperidylmethyl)-1,2,4-oxadiazol-3-yl]aniline", Chem. Pharm. Bull., vol. 47, No. 1, pp. 120-122, (1999).

Trapani, G., et al., "Propofol Analogues. Synthesis, Relationships between Structure and Affinity at GABAA Receptor in Rat Brain, and Differential Electrophysiological Profile at Recombinant Human GABAA Receptors". J. Med. Chem., vol. 41, pp. 1846-1854, (1998).

Yan, L., et al., "Discovery of 3-arylpropionic acids as potent agonists of sphingosine-1-phosphate receptor-1 (S1P1) with high selectivity against all other known S1P receptor subtypes", Bioorganic & Med. Chem. Lett., vol. 16, pp. 3679-3683, (2006).

Zanon, J., et al., "Copper-Catalyzed Domino Halide Exchange-Cyanation of Aryl Bromides", J. Am. Chem. Soc., vol. 125, pp. 2890-2891, (2003).

Zhao, D., et al., "Synthesis and Self-Association of an Imine-Containing m-Phenylene Ethynylene Macrocycle", J. Org. Chem., vol. 67, pp. 3548-3554, (2002).

Zhao, H., et al., "A Practical and Convenient Synthesis of Methyl 5-Formyl-3-Methoxybenzoate", Synthetic Communications, vol. 31, pp. 1921-1926, (2001).

Horuk et al; The Journal of Biological Chemisty vo. 5(12); p. 4199-4204; (2001).

Notice of Allowance dated Jun. 13, 2012 for U.S. Appl. No. 12/310,763.

Notice of Allowance dated Jun. 20, 2012 for U.S. Appl. No. 12/738,110.

Notice of Allowance dated Nov. 18, 2011 for U.S. Appl. No. 12/747,280.

Notice of Allowance dated Sep. 26, 2011 for U.S. Appl. No. 12/442,203.

Office Action—Final dated Jun. 8, 2011 for U.S. Appl. No. 12/442,203.

Office Action—Non-Final dated Mar. 13, 2012 for U.S. Appl. No. 12/738,110.

Office Action—Non-Final dated Nov. 23, 2010 for U.S. Appl. No. 12/442,203.

Office Action—Restriction dated Jul. 24, 2012 for U.S. Appl. No. 12/920,569.

Office Action—Restriction dated May 24, 2012 for U.S. Appl. No. 12/920,656.

Office Action—Restriction dated Sep. 16, 2010 for U.S. Appl. No. 12/442,203.

Office Action—Restriction dated Sep. 29, 2011 for U.S. Appl. No. 12/747,280.

Office Action dated Apr. 26, 2012 for U.S. Appl. No. 12/531,374.

Office Action dated Dec. 2, 2011 for U.S. Appl. No. 12/531,374.

Office Action dated Feb. 17, 2012 for U.S. Appl. No. 12/673,918.

Office Action dated Jun. 11, 2012 for U.S. Appl. No. 12/673,918.

Office Action dated Oct. 31, 2012 for U.S. Appl. No. 12/920,656.

Silverman; "The Organic Chemistry of Drug Design and Drug Action"; 2004; Elsevier, pp. 29-32.

Silverman; "The Organic Chemistry of Drug Design and Drug Action"; 2004; Elsevier, pp. 9.

* cited by examiner

AMINOMETHYL BENZENE DERIVATIVES

CROSS REFERENCE TO RELATED APPLICATIONS

This application is a United States Application under 35 U.S.C. 371 claiming benefit of PCT Application No. PCT/IB2009/050844, filed on Mar. 3, 2009, which claims the benefit of PCT Application No. PCT/IB2008/050841, filed on Mar. 7, 2008, the contents of each of which are incorporated herein by reference.

FIELD OF THE INVENTION

The present invention relates to S1P1/EDG1 receptor agonists of formula (I) and their use as active ingredients in the preparation of pharmaceutical compositions. The invention also concerns related aspects including processes for the preparation of the compounds, pharmaceutical compositions containing a compound of the formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation; however, they exhibit considerable side effects. Alternative treatments include agents that activate or block cytokine signalling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO 91/15583 published 17 Oct. 1991; WO 99/46277 published 16 Sep. 1999. The potency and efficacy of the compounds of formula (I) are assessed using a GTPγS assay to determine $EC_{50}$ values and by measuring the circulating lymphocytes in the rat after oral administration, respectively (see in Examples).

i) The invention relates to novel amino-pyridine compounds of the formula (I)

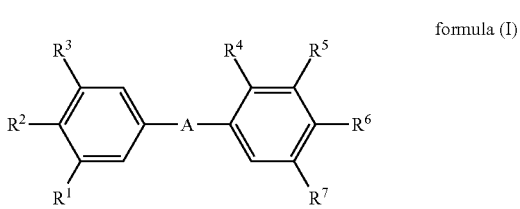

wherein
A represents one of the groups

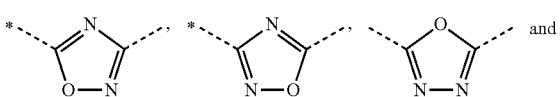

-continued

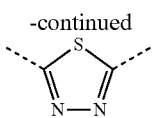

wherein the asterisks indicate the bond that is linked to the phenyl group bearing the substituents $R^1$, $R^2$ and $R^3$;
$R^1$ represents —$CH_2$—$NR^{1a}R^{1b}$, $R^2$ represents hydrogen, and $R^3$ represents hydrogen, $C_{1-4}$ alkyl, or $C_{1-3}$-alkoxy; or
$R^1$ represents —$CH_2$—$NR^{1a}R^{1b}$, $R^2$ represents $C_{1-4}$-alkyl or $C_{1-3}$-alkoxy, and $R^3$ represents hydrogen or methyl; or
$R^1$ represents hydrogen, $C_{1-4}$-alkyl or $C_{1-3}$-alkoxy, $R^2$ represents —$CH_2$—$NR^{2a}R^{2b}$, and $R^3$ represents hydrogen or methyl;
$R^{1a}$ represents $C_{1-4}$-alkyl,
$R^{1b}$ represents hydrogen, or $C_{1-2}$-alkyl, or $R^{1a}$ and $R^{1b}$ together with the nitrogen atom to which they are attached form an azetidine or a pyrrolidine ring;
$R^{2a}$ represents $C_{1-4}$-alkyl,
$R^{2b}$ represents hydrogen, or $C_{1-2}$-alkyl, or $R^{2a}$ and $R^{2b}$ together with the nitrogen atom to which they are attached form an azetidine or a pyrrolidine ring;
$R^4$ represents hydrogen, methyl, methoxy or chloro;
$R^5$ represents hydrogen, $C_{1-3}$-alkyl, methoxy, fluoro or chloro;
$R^6$ represents hydroxy-$C_{1-4}$-alkyl, 2,3-dihydroxypropyl, —$CH_2$—$(CH_2)_n$—$NR^{61}R^{62}$, —$CH_2$—$(CH_2)_n$—$NHCOR^{64}$, —$CH_2$—$(CH_2)_n$—$NHSO_2R^{63}$, —$CH_2$—$CH_2$—$COOH$, —$CH_2$—$CH_2$—$CONR^{61}R^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, —$CH_2$—$CH(OH)$—$CH_2$—$NR^{61}R^{62}$, —$CH_2$—$CH(OH)$—$CH_2$—$NHCOR^{64}$, —$CH_2$—$CH(OH)$—$CH_2$—$NHSO_2R^{63}$, hydroxy, hydroxy-$C_{2-4}$-alkoxy, 1-hydroxymethyl-2-hydroxy-ethoxy, 2,3-dihydroxypropoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —$OCH_2$—$CH(OH)$—$CH_2$—$NR^{61}R^{62}$, —$OCH_2$—$CH(OH)$—$CH_2$—$NHCOR^{64}$, —$OCH_2$—$CH(OH)$—$CH_2$—$NHSO_2R^{63}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, —$NR^{61}R^{62}$, —$NHCO$—$R^{64}$;
$R^{61}$ represents hydrogen, methyl, ethyl, 2-hydroxyethyl, 3-hydroxypropyl, 2-aminoethyl, 2-($C_{1-4}$-alkylamino)ethyl, 2-(di-($C_{1-4}$-alkyl)amino)ethyl, carboxymethyl, ($C_{1-4}$-alkylcarboxy)methyl, 2-carboxyethyl, or 2-($C_{1-4}$-alkylcarboxy) ethyl;
$R^{62}$ represents hydrogen or methyl;
$R^{63}$ represents methyl, ethyl, methylamino, or dimethylamino;
$R^{64}$ represents hydroxymethyl, 2-hydroxyethyl, methylaminomethyl, dimethylaminomethyl, or 2-methylamino-ethyl;
m represents the integer 1 or 2;
n represents 0, 1 or 2; and
$R^7$ represents hydrogen, or $C_{1-2}$-alkyl.

The general terms used hereinbefore and hereinafter preferably have, within this disclosure, the following meanings, unless otherwise indicated:

The term "$C_{x-y}$-alkyl", x and y being integers, refers to a straight or branched alkyl chain with x to y carbon atoms. For example, the term "$C_{1-4}$-alkyl" refers to a straight or branched alkyl chain with one to four carbon atoms. Examples of $C_{1-4}$-alkyl groups are methyl, ethyl, n-propyl, iso-propyl, n-butyl and iso-butyl (methyl, ethyl, n-propyl, iso-propyl and iso-butyl being preferred). Examples of $C_{1-3}$-alkyl groups are methyl, ethyl, n-propyl and iso-propyl (methyl and ethyl being preferred).

The term "$C_{x-y}$-alkoxy", x and y being integers, refers to a O—$C_{x-y}$-alkyl group, wherein the $C_{x-y}$-alkyl group is as defined previously. For example, the term "$C_{1-4}$-alkoxy" refers to a straight or branched alkoxy chain with one to four carbon atoms. Examples of $C_{1-4}$-alkoxy groups are methoxy, ethoxy, propoxy, iso-propoxy and iso-butoxy (methoxy being preferred). Preferred examples of $C_{2-4}$-alkoxy groups are ethoxy, propoxy and iso-propoxy.

Room temperature means 20° C.

ii) A further embodiment of the invention relates to aminomethyl benzene derivatives according to embodiment i), wherein A represents one of the groups

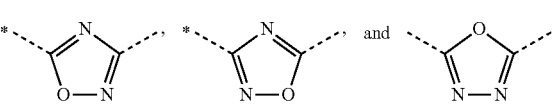

wherein the asterisks indicate the bond that is linked to the phenyl group bearing the substituents $R^1$, $R^2$ and $R^3$.

iii) Another embodiment of the invention relates to aminomethyl benzene derivatives according to embodiment i) or ii), wherein A represents the group

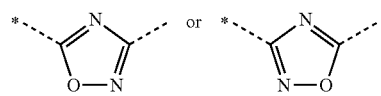

wherein the asterisks indicate the bond that is linked to the phenyl group bearing the substituents $R^1$, $R^2$ and $R^3$.

iv) Another embodiment of the invention relates to aminopyridine derivatives according to one of embodiments i) to iii), wherein A represents the group

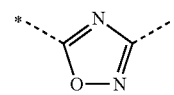

wherein the asterisk indicates the bond that is linked to the phenyl group bearing the substituents $R^1$, $R^2$ and $R^3$.

v) Another particular embodiment of the invention relates to aminomethyl benzene derivatives according to embodiments i) to iv), wherein $R^1$ represents —$CH_2$—$NR^{1a}R^{1b}$, $R^2$ represents hydrogen and $R^3$ represents hydrogen, $C_{1-4}$-alkyl or $C_{1-3}$-alkoxy.

vi) Another particular embodiment of the invention relates to aminomethyl benzene derivatives according to embodiments i) to iv), wherein $R^1$ represents —$CH_2$—$NR^{1a}R^{1b}$, $R^2$ represents hydrogen, and $R^3$ represents $C_{1-2}$-alkyl.

vii) Another particular embodiment of the invention relates to aminomethyl benzene derivatives according to embodiments i) to iv), wherein $R^1$ represents —$CH_2$—$NR^{1a}R^{1b}$, $R^2$ represents $C_{1-4}$-alkyl or $C_{1-3}$-alkoxy, and $R^3$ represents hydrogen or methyl.

viii) Another particular embodiment of the invention relates to aminomethyl benzene derivatives according to embodiments i) to iv), wherein $R^1$ represents —CH$_2$—NR$^{1a}$R$^{1b}$, $R^2$ represents C$_{1-4}$-alkyl, and $R^3$ represents hydrogen.

ix) Another particular embodiment of the invention relates to aminomethyl benzene derivatives according to any one of the embodiments i) to viii), wherein $R^{1a}$ represents C$_{1-4}$-alkyl, and $R^{1b}$ represents C$_{1-2}$-alkyl.

x) Another particular embodiment of the invention relates to aminomethyl benzene derivatives according to embodiments i) to iv), wherein $R^1$ represents hydrogen, C$_{1-4}$-alkyl or C$_{1-3}$-alkoxy, $R^2$ represents —CH$_2$—NR$^{2a}$R$^{2b}$, and $R^3$ represents hydrogen or methyl.

xi) Another particular embodiment of the invention relates to aminomethyl benzene derivatives according to embodiments i) to iv), wherein $R^1$ represents hydrogen or C$_{1-4}$-alkyl, $R^2$ represents —CH$_2$—NR$^{2a}$R$^{2b}$, and $R^3$ represents hydrogen.

xii) Another particular embodiment of the invention relates to aminomethyl benzene derivatives according to any one of the embodiments i) to iv) and x) to xi), wherein $R^{2a}$ represents C$_{1-4}$-alkyl, and $R^{2b}$ represents C$_{1-2}$-alkyl.

xiii) Another embodiment of the invention relates to pyridine derivatives according to any one of the embodiments i) to xii), wherein at least one of $R^4$, $R^5$ and $R^7$ represents a group other than hydrogen.

xiv) Another particular embodiment of the invention relates to aminomethyl benzene derivatives according to any one of the embodiments i) to xii), wherein $R^4$ represents methoxy, and $R^5$ and $R^7$ represent hydrogen.

xv) Another particular embodiment of the invention relates to aminomethyl benzene derivatives according to any one of the embodiments i) to xii), wherein $R^4$ represents hydrogen, $R^5$ represents C$_{1-3}$-alkyl or methoxy (and notably C$_{1-3}$-alkyl), and $R^7$ represents C$_{1-2}$-alkyl or chloro (and notably C$_{1-2}$-alkyl).

xvi) Another particular embodiment of the invention relates to aminomethyl benzene derivatives according to any one of the embodiments i) to xii), wherein $R^4$ represents hydrogen, $R^5$ represents C$_{1-2}$-alkyl or methoxy, and $R^7$ represents methyl or chloro.

xvii) Another particular embodiment of the invention relates to aminomethyl benzene derivatives according to any one of the embodiments i) to xii), wherein $R^4$ represents hydrogen, $R^5$ represents ethyl or methoxy, and $R^7$ represents methyl or chloro.

xviii) Another particular embodiment of the invention relates to aminomethyl benzene derivatives according to any one of the embodiments i) to xii), wherein $R^4$ represents hydrogen, $R^5$ represents ethyl, and $R^7$ represents methyl.

xix) Another particular embodiment of the invention relates to aminomethyl benzene derivatives according to any one of the embodiments i) to xviii), wherein $R^6$ represents di-(hydroxy-C$_{1-4}$-alkyl)-C$_{1-4}$-alkyl, 2,3-dihydroxypropyl, —CH$_2$—(CH$_2$)$_n$—NHCOR$^{64}$, —CH$_2$—(CH$_2$)$_n$—NHSO$_2$R$^{63}$, —CH$_2$—CH$_2$—COOH, —CH$_2$—CH$_2$—CONR$^{61}$R$^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, —CH$_2$—CH(OH)—CH$_2$—NR$^{61}$R$^{62}$, —CH$_2$—CH(OH)—CH$_2$—NHCOR$^{64}$, —CH$_2$—CH(OH)—CH$_2$—NHSO$_2$R$^{63}$, —CO—NHR$^{61}$, hydroxy-C$_{2-4}$-alkoxy, di-(hydroxy-C$_{1-4}$-alkyl)-C$_{1-4}$-alkoxy, 2,3-dihydroxypropoxy, 2-hydroxy-3-methoxy-propoxy, —OCH$_2$—(CH$_2$)$_m$—NR$^{61}$R$^{62}$, —OCH$_2$—(CH$_2$)$_m$—NHCOR$^{64}$, —OCH$_2$—(CH$_2$)$_m$—NHSO$_2$R$^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —OCH$_2$—CH(OH)—CH$_2$—NR$^{61}$R$^{62}$, —OCH$_2$—CH(OH)—CH$_2$—NHCOR$^{64}$, —OCH$_2$—CH(OH)—CH$_2$—NHSO$_2$R$^{63}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, or —NR$^{61}$R$^{62}$.

xx) Another particular embodiment of the invention relates to aminomethyl benzene derivatives according to any one of the embodiments i) to xviii), wherein $R^6$ represents —CH$_2$—CH$_2$—COOH, —CH$_2$—CH$_2$—CONR$^{61}$R$^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, hydroxy, hydroxy-C$_{2-4}$-alkoxy, di-(hydroxy-C$_{1-4}$-alkyl)-C$_{1-4}$-alkoxy, 2,3-dihydroxypropoxy, —OCH$_2$—(CH$_2$)$_m$—NR$^{61}$R$^{62}$, —OCH$_2$—(CH$_2$)$_m$—NHCOR$^{64}$, —OCH$_2$—(CH$_2$)$_m$—NHSO$_2$R$^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —OCH$_2$—CH(OH)—CH$_2$—NR$^{61}$R$^{62}$, —OCH$_2$—CH(OH)—CH$_2$—NHCOR$^{64}$, —OCH$_2$—CH(OH)—CH$_2$—NHSO$_2$R$^{63}$, 3-[(azetidine-3-carboxylic acid)-1-yl]-2-hydroxypropoxy, 2-hydroxy-3-[(pyrrolidine-2-carboxylic acid)-1-yl]-propoxy or 2-hydroxy-3-[(pyrrolidine-3-carboxylic acid)-1-yl]-propoxy.

xxi) Another particular embodiment of the invention relates to aminomethyl benzene derivatives according to any one of the embodiments i) to xviii), wherein $R^6$ represents —CH$_2$—CH$_2$—CONR$^{61}$R$^{62}$, hydroxy, hydroxy-C$_{2-4}$-alkoxy, di-(hydroxy-C$_{1-4}$-alkyl)-C$_{1-4}$-alkoxy, 2,3-dihydroxypropoxy, —OCH$_2$—(CH$_2$)$_m$—NR$^{61}$R$^{62}$, —OCH$_2$—(CH$_2$)$_m$—NHCOR$^{64}$, —OCH$_2$—(CH$_2$)$_m$—NHSO$_2$R$^{63}$, —OCH$_2$—CH(OH)—CH$_2$—NR$^{61}$R$^{62}$, —OCH$_2$—CH(OH)—CH$_2$—NHCOR$^{64}$ or —OCH$_2$—CH(OH)—CH$_2$—NHSO$_2$R$^{63}$.

xxii) Another particular embodiment of the invention relates to aminomethyl benzene derivatives according to any one of the embodiments i) to xviii), wherein $R^6$ represents di-(hydroxy-C$_{1-4}$-alkyl)-C$_{1-4}$-alkoxy, 2,3-dihydroxypropoxy, —OCH$_2$—(CH$_2$)$_m$—NR$^{61}$R$^{62}$, —OCH$_2$—(CH$_2$)$_m$—NHCOR$^{64}$, —OCH$_2$—CH(OH)—CH$_2$—NR$^{61}$R$^{62}$, or —OCH$_2$—CH(OH)—CH$_2$—NHCOR$^{64}$.

xxiii) Another particular embodiment of the invention relates to aminomethyl benzene derivatives according to any one of the embodiments i) to xviii), wherein $R^6$ represents di-(hydroxy-C$_{1-4}$-alkyl)-C$_{1-4}$-alkoxy, 2,3-dihydroxypropoxy, —OCH$_2$—CH(OH)—CH$_2$—NR$^{61}$R$^{62}$ or —OCH$_2$—CH(OH)—CH$_2$—NHCOR$^{64}$.

xxiv) Another particular embodiment of the invention relates to aminomethyl benzene derivatives according to any one of the embodiments i) to xviii), wherein $R^6$ represents 2,3-dihydroxypropoxy or —OCH$_2$—CH(OH)—CH$_2$—NHCOR$^{64}$ (notably —OCH$_2$—CH(OH)—CH$_2$—NHCOR$^{64}$).

xxv) According to a particular embodiment, the aminomethyl benzene derivatives of the invention according to any one of the embodiments i) to xxi) or xxiv), will be such that $R^6$ represents —OCH$_2$—CH(OH)—CH$_2$—NHCOR$^{64}$ and the absolute configuration of the OH group in the side chain $R^6$ is (S), i.e. as represented below:

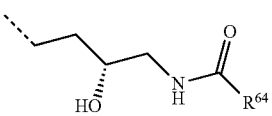

xxvi) Another particular embodiment of the invention relates to aminomethyl benzene derivatives according to any one of the embodiments i) to xxi), wherein $R^{63}$ represents methyl or methylamino.

xxvii) Another particular embodiment of the invention relates to aminomethyl benzene derivatives according to any one of the embodiments i) to xxiii), wherein $R^{61}$ represents methyl, 2-hydroxyethyl, carboxymethyl, or 2-carboxyethyl.

xxviii) Another particular embodiment of the invention relates to aminomethyl benzene derivatives according to any one of the embodiments i) to xxiii) and xxvii), wherein $R^{62}$ represents hydrogen.

xxviii) Another particular embodiment of the invention relates to aminomethyl benzene derivatives according to any one of the embodiments i) to xxv), wherein $R^{64}$ represents hydroxymethyl or 2-hydroxyethyl.

xxix) A further embodiment of the invention relates to aminomethyl benzene derivatives according to embodiment i), wherein A represents the group

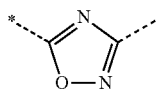

wherein the asterisk indicates the bond that is linked to the phenyl group bearing the substituents $R^1$, $R^2$ and $R^3$
$R^1$ represents —$CH_2$—$NR^{1a}R^{1b}$, $R^{1a}$ representing $C_{1-4}$-alkyl and $R^{1b}$ representing $C_{1-2}$-alkyl;
$R^2$ represents hydrogen;
$R^3$ represents $C_{1-2}$-alkyl;
$R^4$ represents hydrogen;
$R^5$ represents $C_{1-3}$-alkyl, methoxy or chloro;
$R^6$ represents —$CH_2$—$CH_2$—COOH, hydroxy, 2,3-dihydroxypropoxy, or —$OCH_2$—CH(OH)—$CH_2$—$NHCOR^{64}$;
$R^{64}$ represents hydroxymethyl; and
$R^7$ represents $C_{1-2}$-alkyl.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of formula (I) is to be understood as referring also to salts, especially pharmaceutically acceptable salts, of a compound of formula (I), as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Examples of preferred compounds are selected from the group consisting of:
N—((S)-3-{4-[5-(3-dimethylaminomethyl-5-methyl-phenyl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{3-[(ethyl-methyl-amino)-methyl]-5-methyl-phenyl}-[1,2,4]oxadiazol-3-yl)-6-methyl-phenoxy]-2-hydroxy-propyl}-2-hydroxy-acetamide;
N—{(S)-3-[2-ethyl-6-methyl-4-(5-{3-methyl-5-[(methyl-propyl-amino)-methyl]-phenyl}-[1,2,4]oxadiazol-3-yl)phenoxy]-2-hydroxy-propyl}-2-hydroxy-acetamide;
N—{(S)-3-[4-(5-{3-[(butyl-methyl-amino)-methyl]-5-methyl-phenyl}-[1,2,4]oxadiazol-3-yl)-2-ethyl-6-methyl-phenoxy]-2-hydroxy-propyl}-2-hydroxy-acetamide;
N—{(S)-3-[2-ethyl-4-(5-{3-[(isobutyl-methyl-amino)-methyl]-5-methyl-phenyl}-[1,2,4]oxadiazol-3-yl)-6-methyl-phenoxy]-2-hydroxy-propyl}-2-hydroxy-acetamide;
N—((S)-3-{4-[5-(3-Diethylaminomethyl-5-methyl-phenyl)-[1,2,4]oxadiazol-3-yl]-2-ethyl-6-methyl-phenoxy}-2-hydroxy-propyl)-2-hydroxy-acetamide;
N—{(S)-3-[4-(5-{3-[(butyl-ethyl-amino)-methyl]-5-methyl-phenyl}-[1,2,4]oxadiazol-3-yl)-2-ethyl-6-methyl-phenoxy]-2-hydroxy-propyl}-2-hydroxy-acetamide;
N—((S)-3-{2-ethyl-6-methyl-4-[5-(3-methyl-5-pyrrolidin-1-ylmethyl-phenyl)-[1,2,4]oxadiazol-3-yl]-phenoxy}-2-hydroxy-propyl)-2-hydroxy-acetamide;
N—{(S)-3-[4-(5-{4-[(butyl-ethyl-amino)-methyl]-3-methyl-phenyl}-[1,2,4]oxadiazol-3-yl)-2,6-dimethyl-phenoxy]-2-hydroxy-propyl}-2-hydroxy-acetamide;
N—((S)-3-{4-[5-(4-dimethylaminomethyl-3-methyl-phenyl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{4-[(ethyl-methyl-amino)-methyl]-3-methyl-phenyl}-[1,2,4]oxadiazol-3-yl)-6-methyl-phenoxy]-2-hydroxy-propyl}-2-hydroxy-acetamide;
N—{(S)-3-[4-(5-{4-[(butyl-methyl-amino)-methyl]-3-methyl-phenyl}-[1,2,4]oxadiazol-3-yl)-2-ethyl-6-methyl-phenoxy]-2-hydroxy-propyl}-2-hydroxy-acetamide;
N—{(S)-3-[2-ethyl-4-(5-{4-[(isobutyl-methyl-amino)-methyl]-3-methyl-phenyl}-[1,2,4]oxadiazol-3-yl)-6-methyl-phenoxy]-2-hydroxy-propyl}-2-hydroxy-acetamide; and
N—((S)-3-{4-[5-(4-diethylaminomethyl-3-methyl-phenyl)-[1,2,4]oxadiazol-3-yl]-2-ethyl-6-methyl-phenoxy}-2-hydroxy-propyl)-2-hydroxy-acetamide.

Further examples of preferred compounds are selected from the group consisting of:
N—((S)-3-{2-ethyl-4-[5-(3-ethyl-5-propylaminomethyl-phenyl)-[1,2,4]oxadiazol-3-yl]-6-methyl-phenoxy}-2-hydroxy-propyl)-2-hydroxy-acetamide;
N—((S)-3-{4-[5-(3-butylaminomethyl-5-ethyl-phenyl)-[1,2,4]oxadiazol-3-yl]-2-ethyl-6-methyl-phenoxy}-2-hydroxy-propyl)-2-hydroxy-acetamide;
N—[(S)-3-(2-ethyl-4-{5-[3-ethyl-5-(isobutylamino-methyl)-phenyl]-[1,2,4]oxadiazol-3-yl}-6-methyl-phenoxy)-2-hydroxy-propyl]-2-hydroxy-acetamide;
N—((S)-3-{4-[5-(3-dimethylaminomethyl-5-ethyl-phenyl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{3-ethyl-5-[(ethyl-methyl-amino)-methyl]-phenyl}-[1,2,4]oxadiazol-3-yl)-6-methyl-phenoxy]-2-hydroxy-propyl}-2-hydroxy-acetamide;
N—{(S)-3-[2-ethyl-4-(5-{3-ethyl-5-[(methyl-propyl-amino)-methyl]-phenyl}-[1,2,4]oxadiazol-3-yl)-6-methyl-phenoxy]-2-hydroxy-propyl}-2-hydroxy-acetamide;
N—{(S)-3-[4-(5-{3-[(butyl-methyl-amino)-methyl]-5-ethyl-phenyl}-[1,2,4]oxadiazol-3-yl)-2-ethyl-6-methyl-phenoxy]-2-hydroxy-propyl}-2-hydroxy-acetamide;
N—{(S)-3-[2-ethyl-4-(5-{3-ethyl-5-[(isobutyl-methyl-amino)-methyl]-phenyl}-[1,2,4]oxadiazol-3-yl)-6-methyl-phenoxy]-2-hydroxy-propyl}-2-hydroxy-acetamide;
N—((S)-3-{4-[5-(3-diethylaminomethyl-5-ethyl-phenyl)-[1,2,4]oxadiazol-3-yl]-2-ethyl-6-methyl-phenoxy}-2-hydroxy-propyl)-2-hydroxy-acetamide;
N—((S)-3-{2-ethyl-4-[5-(3-ethyl-5-pyrrolidin-1-ylmethyl-phenyl)-[1,2,4]oxadiazol-3-yl]-6-methyl-phenoxy}-2-hydroxy-propyl)-2-hydroxy-acetamide;
N—((S)-3-{2-ethyl-6-methyl-4-[5-(3-propyl-5-propylaminomethyl-phenyl)-[1,2,4]oxadiazol-3-yl]-phenoxy}-2-hydroxy-propyl)-2-hydroxy-acetamide;

N—((S)-3-{4-[5-(3-butylaminomethyl-5-propyl-phenyl)-[1,2,4]oxadiazol-3-yl]-2-ethyl-6-methyl-phenoxy}-2-hydroxy-propyl)-2-hydroxy-acetamide;

N—[(S)-3-(2-ethyl-4-{5-[3-(isobutylamino-methyl)-5-propyl-phenyl]-[1,2,4]oxadiazol-3-yl}-6-methyl-phenoxy)-2-hydroxy-propyl]-2-hydroxy-acetamide;

N—((S)-3-{4-[5-(3-dimethylaminomethyl-5-propyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-[(ethyl-methyl-amino)-methyl]-5-propyl-phenyl}-[1,2,4]oxadiazol-3-yl)-6-methyl-phenoxy]-2-hydroxy-propyl}-2-hydroxy-acetamide;

N—{(S)-3-[2-ethyl-6-methyl-4-(5-{3-[(methyl-propyl-amino)-methyl]-5-propyl-phenyl}-[1,2,4]oxadiazol-3-yl)-phenoxy]-2-hydroxy-propyl}-2-hydroxy-acetamide;

N—{(S)-3-[4-(5-{3-[(butyl-methyl-amino)-methyl]-5-propyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{3-[(isobutyl-methyl-amino)-methyl]-5-propyl-phenyl}-[1,2,4]oxadiazol-3-yl)-6-methyl-phenoxy]-2-hydroxy-propyl}-2-hydroxy-acetamide;

N—((S)-3-{4-[5-(3-diethylaminomethyl-5-propyl-phenyl)-[1,2,4]oxadiazol-3-yl]-2-ethyl-6-methyl-phenoxy}-2-hydroxy-propyl)-2-hydroxy-acetamide;

N—((S)-3-{2-ethyl-6-methyl-4-[5-(3-propyl-5-pyrrolidin-1-ylmethyl-phenyl)-[1,2,4]oxadiazol-3-yl]-phenoxy}-2-hydroxy-propyl)-2-hydroxy-acetamide;

N—((S)-3-{2-ethyl-4-[5-(3-isopropyl-5-propylaminomethyl-phenyl)-[1,2,4]oxadiazol-3-yl]-6-methyl-phenoxy}-2-hydroxy-propyl)-2-hydroxy-acetamide;

N—((S)-3-{4-[5-(3-butylaminomethyl-5-isopropyl-phenyl)-[1,2,4]oxadiazol-3-yl]-2-ethyl-6-methyl-phenoxy}-2-hydroxy-propyl)-2-hydroxy-acetamide;

N—[(S)-3-(2-ethyl-4-{5-[3-(isobutylamino-methyl)-5-isopropyl-phenyl]-[1,2,4]oxadiazol-3-yl}-6-methyl-phenoxy)-2-hydroxy-propyl]-2-hydroxy-acetamide;

N—((S)-3-{4-[5-(3-dimethylaminomethyl-5-isopropyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-[(ethyl-methyl-amino)-methyl]-5-isopropyl-phenyl}-[1,2,4]oxadiazol-3-yl)-6-methyl-phenoxy]-2-hydroxy-propyl}-2-hydroxy-acetamide;

N—{(S)-3-[2-ethyl-4-(5-{3-isopropyl-5-[(methyl-propyl-amino)-methyl]-phenyl}-[1,2,4]oxadiazol-3-yl)-6-methyl-phenoxy]-2-hydroxy-propyl}-2-hydroxy-acetamide;

N—{(S)-3-[4-(5-{3-[(butyl-methyl-amino)-methyl]-5-isopropyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{3-[(isobutyl-methyl-amino)-methyl]-5-isopropyl-phenyl}-[1,2,4]oxadiazol-3-yl)-6-methyl-phenoxy]-2-hydroxy-propyl}-2-hydroxy-acetamide;

N—((S)-3-{4-[5-(3-diethylaminomethyl-5-isopropyl-phenyl)-[1,2,4]oxadiazol-3-yl]-2-ethyl-6-methyl-phenoxy}-2-hydroxy-propyl)-2-hydroxy-acetamide;

N—((S)-3-{2-ethyl-4-[5-(3-isopropyl-5-pyrrolidin-1-ylmethyl-phenyl)-[1,2,4]oxadiazol-3-yl]-6-methyl-phenoxy}-2-hydroxy-propyl)-2-hydroxy-acetamide;

N—((S)-3-{4-[5-(4-dimethylaminomethyl-3-ethyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-ethyl-4-[(ethyl-methyl-amino)-methyl]-phenyl}-[1,2,4]oxadiazol-3-yl)-6-methyl-phenoxy]-2-hydroxy-propyl}-2-hydroxy-acetamide;

N—{(S)-3-[2-ethyl-4-(5-{3-ethyl-4-[(isobutyl-methyl-amino)-methyl]-phenyl}-[1,2,4]oxadiazol-3-yl)-6-methyl-phenoxy]-2-hydroxy-propyl}-2-hydroxy-acetamide;

N—((S)-3-{2-ethyl-4-[5-(3-ethyl-4-pyrrolidin-1-ylmethyl-phenyl)-[1,2,4]oxadiazol-3-yl]-6-methyl-phenoxy}-2-hydroxy-propyl)-2-hydroxy-acetamide;

N—((S)-3-{4-[5-(4-dimethylaminomethyl-3-methyl-phenyl)-[1,2,4]oxadiazol-3-yl]-2,6-dimethyl-phenoxy}-2-hydroxy-propyl)-2-hydroxy-acetamide;

(S)-3-[2-chloro-4-(5-{3-[(ethyl-methyl-amino)-methyl]-5-methyl-phenyl}-[1,2,4]oxadiazol-3-yl)-6-methyl-phenoxy]-propane-1,2-diol;

N—{(S)-3-[4-(5-{3-[(ethyl-methyl-amino)-methyl]-5-methyl-phenyl}-[1,2,4]oxadiazol-3-yl)-2,6-dimethyl-phenoxy]-2-hydroxy-propyl}-2-hydroxy-acetamide;

N—{(S)-3-[2-chloro-4-(5-{3-[(ethyl-methyl-amino)-methyl]-5-methyl-phenyl}-[1,2,4]oxadiazol-3-yl)-6-methyl-phenoxy]-2-hydroxy-propyl}-2-hydroxy-acetamide;

N—{(S)-3-[4-(5-{3-[(ethyl-methyl-amino)-methyl]-5-methyl-phenyl}-[1,2,4]oxadiazol-3-yl)-2-methoxy-6-methyl-phenoxy]-2-hydroxy-propyl}-2-hydroxy-acetamide; and (S)-3-[2-ethyl-4-(5-{3-[(ethyl-methyl-amino)-methyl]-5-methyl-phenyl}-[1,2,4]oxadiazol-3-yl)-6-methyl-phenoxy]-propane-1,2-diol.

According to a particular embodiment of this invention, the further examples of preferred compounds mentioned previously will be selected from the group consisting of:

N—((S)-3-{2-ethyl-4-[5-(3-ethyl-5-propylaminomethyl-phenyl)-[1,2,4]oxadiazol-3-yl]-6-methyl-phenoxy}-2-hydroxy-propyl)-2-hydroxy-acetamide;

N—((S)-3-{4-[5-(3-butylaminomethyl-5-ethyl-phenyl)-[1,2,4]oxadiazol-3-yl]-2-ethyl-6-methyl-phenoxy}-2-hydroxy-propyl)-2-hydroxy-acetamide;

N—[(S)-3-(2-ethyl-4-{5-[3-ethyl-5-(isobutylamino-methyl)-phenyl]-[1,2,4]oxadiazol-3-yl}-6-methyl-phenoxy)-2-hydroxy-propyl]-2-hydroxy-acetamide;

N—((S)-3-{4-[5-(3-dimethylaminomethyl-5-ethyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-ethyl-5-[(ethyl-methyl-amino)-methyl]-phenyl}-[1,2,4]oxadiazol-3-yl)-6-methyl-phenoxy]-2-hydroxy-propyl}-2-hydroxy-acetamide;

N—{(S)-3-[2-ethyl-4-(5-{3-ethyl-5-[(methyl-propyl-amino)-methyl]-phenyl}-[1,2,4]oxadiazol-3-yl)-6-methyl-phenoxy]-2-hydroxy-propyl}-2-hydroxy-acetamide;

N—{(S)-3-[4-(5-{3-[(butyl-methyl-amino)-methyl]-5-ethyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{3-ethyl-5-[(isobutyl-methyl-amino)-methyl]-phenyl}-[1,2,4]oxadiazol-3-yl)-6-methyl-phenoxy]-2-hydroxy-propyl}-2-hydroxy-acetamide;

N—((S)-3-{4-[5-(3-diethylaminomethyl-5-ethyl-phenyl)-[1,2,4]oxadiazol-3-yl]-2-ethyl-6-methyl-phenoxy}-2-hydroxy-propyl)-2-hydroxy-acetamide;

N—((S)-3-{2-ethyl-4-[5-(3-ethyl-5-pyrrolidin-1-ylmethyl-phenyl)-[1,2,4]oxadiazol-3-yl]-6-methyl-phenoxy}-2-hydroxy-propyl)-2-hydroxy-acetamide;

N—((S)-3-{2-ethyl-6-methyl-4-[5-(3-propyl-5-propylaminomethyl-phenyl)-[1,2,4]oxadiazol-3-yl]-phenoxy}-2-hydroxy-propyl)-2-hydroxy-acetamide;

N—((S)-3-{4-[5-(3-butylaminomethyl-5-propyl-phenyl)-[1,2,4]oxadiazol-3-yl]-2-ethyl-6-methyl-phenoxy}-2-hydroxy-propyl)-2-hydroxy-acetamide;

N—[(S)-3-(2-ethyl-4-{5-[3-(isobutylamino-methyl)-5-propyl-phenyl]-[1,2,4]oxadiazol-3-yl}-6-methyl-phenoxy)-2-hydroxy-propyl]-2-hydroxy-acetamide;

N—((S)-3-{4-[5-(3-dimethylaminomethyl-5-propyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-[(ethyl-methyl-amino)-methyl]-5-propyl-phenyl}-[1,2,4]oxadiazol-3-yl)-6-methyl-phenoxy]-2-hydroxy-propyl}-2-hydroxy-acetamide;
N—{(S)-3-[2-ethyl-6-methyl-4-(5-{3-[(methyl-propyl-amino)-methyl]-5-propyl-phenyl}-[1,2,4]oxadiazol-3-yl)-phenoxy]-2-hydroxy-propyl}-2-hydroxy-acetamide;
N—{(S)-3-[4-(5-{3-[(butyl-methyl-amino)-methyl]-5-propyl-phenyl}-[1,2,4]oxadiazol-3-yl)-2-ethyl-6-methyl-phenoxy]-2-hydroxy-propyl}-2-hydroxy-acetamide;
N—{(S)-3-[2-ethyl-4-(5-{3-[(isobutyl-methyl-amino)-methyl]-5-propyl-phenyl}-[1,2,4]oxadiazol-3-yl)-6-methyl-phenoxy]-2-hydroxy-propyl}-2-hydroxy-acetamide;
N—((S)-3-{4-[5-(3-diethylaminomethyl-5-propyl-phenyl)-[1,2,4]oxadiazol-3-yl]-2-ethyl-6-methyl-phenoxy}-2-hydroxy-propyl)-2-hydroxy-acetamide;
N—((S)-3-{2-ethyl-6-methyl-4-[5-(3-propyl-5-pyrrolidin-1-ylmethyl-phenyl)-[1,2,4]oxadiazol-3-yl]-phenoxy}-2-hydroxy-propyl)-2-hydroxy-acetamide;
N—((S)-3-{2-ethyl-4-[5-(3-isopropyl-5-propylaminomethyl-phenyl)-[1,2,4]oxadiazol-3-yl]-6-methyl-phenoxy}-2-hydroxy-propyl)-2-hydroxy-acetamide;
N—((S)-3-{4-[5-(3-butylaminomethyl-5-isopropyl-phenyl)-[1,2,4]oxadiazol-3-yl]-2-ethyl-6-methyl-phenoxy}-2-hydroxy-propyl)-2-hydroxy-acetamide;
N—[(S)-3-(2-ethyl-4-{5-[3-(isobutylamino-methyl)-5-isopropyl-phenyl]-[1,2,4]oxadiazol-3-yl}-6-methyl-phenoxy)-2-hydroxy-propyl]-2-hydroxy-acetamide;
N—((S)-3-{4-[5-(3-dimethylaminomethyl-5-isopropyl-phenyl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{3-[(ethyl-methyl-amino)-methyl]-5-isopropyl-phenyl}-[1,2,4]oxadiazol-3-yl)-6-methyl-phenoxy]-2-hydroxy-propyl}-2-hydroxy-acetamide;
N—{(S)-3-[2-ethyl-4-(5-{3-isopropyl-5-[(methyl-propyl-amino)-methyl]-phenyl}-[1,2,4]oxadiazol-3-yl)-6-methyl-phenoxy]-2-hydroxy-propyl}-2-hydroxy-acetamide;
N—{(S)-3-[4-(5-{3-[(butyl-methyl-amino)-methyl]-5-isopropyl-phenyl}-[1,2,4]oxadiazol-3-yl)-2-ethyl-6-methyl-phenoxy]-2-hydroxy-propyl}-2-hydroxy-acetamide;
N—{(S)-3-[2-ethyl-4-(5-{3-[(isobutyl-methyl-amino)-methyl]-5-isopropyl-phenyl}-[1,2,4]oxadiazol-3-yl)-6-methyl-phenoxy]-2-hydroxy-propyl}-2-hydroxy-acetamide;
N—((S)-3-{4-[5-(3-diethylaminomethyl-5-isopropyl-phenyl)-[1,2,4]oxadiazol-3-yl]-2-ethyl-6-methyl-phenoxy}-2-hydroxy-propyl)-2-hydroxy-acetamide;
N—((S)-3-{2-ethyl-4-[5-(3-isopropyl-5-pyrrolidin-1-ylmethyl-phenyl)-[1,2,4]oxadiazol-3-yl]-6-methyl-phenoxy}-2-hydroxy-propyl)-2-hydroxy-acetamide;
N—((S)-3-{4-[5-(4-dimethylaminomethyl-3-ethyl-phenyl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{3-ethyl-4-[(ethyl-methyl-amino)-methyl]-phenyl}-[1,2,4]oxadiazol-3-yl)-6-methyl-phenoxy]-2-hydroxy-propyl}-2-hydroxy-acetamide;
N—{(S)-3-[2-ethyl-4-(5-{3-ethyl-4-[(isobutyl-methyl-amino)-methyl]-phenyl}-[1,2,4]oxadiazol-3-yl)-6-methyl-phenoxy]-2-hydroxy-propyl}-2-hydroxy-acetamide;
N—((S)-3-{2-ethyl-4-[5-(3-ethyl-4-pyrrolidin-1-ylmethyl-phenyl)-[1,2,4]oxadiazol-3-yl]-6-methyl-phenoxy}-2-hydroxy-propyl)-2-hydroxy-acetamide;
N—((S)-3-{4-[5-(4-dimethylaminomethyl-3-methyl-phenyl)-[1,2,4]oxadiazol-3-yl]-2,6-dimethyl-phenoxy}-2-hydroxy-propyl)-2-hydroxy-acetamide;
N—{(S)-3-[4-(5-{3-[(ethyl-methyl-amino)-methyl]-5-methyl-phenyl}-[1,2,4]oxadiazol-3-yl)-2,6-dimethyl-phenoxy]-2-hydroxy-propyl}-2-hydroxy-acetamide;
N—{(S)-3-[2-chloro-4-(5-{3-[(ethyl-methyl-amino)-methyl]-5-methyl-phenyl}-[1,2,4]oxadiazol-3-yl)-6-methyl-phenoxy]-2-hydroxy-propyl}-2-hydroxy-acetamide; and
N—{(S)-3-[4-(5-{3-[(ethyl-methyl-amino)-methyl]-5-methyl-phenyl}-[1,2,4]oxadiazol-3-yl)-2-methoxy-6-methyl-phenoxy]-2-hydroxy-propyl}-2-hydroxy-acetamide.

The compounds of formula (I) and their pharmaceutically acceptable salts can be used as medicaments, e.g. in the form of pharmaceutical compositions for enteral or parenteral administration and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of formula (I) are useful for the prevention and/or treatment of diseases or disorders associated with an activated immune system.

Such diseases or disorders include rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain- Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fasciitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of formula (I) are selected from multiple sclerosis and psoriasis.

The present invention also relates to a method for the prevention or treatment of a disease or disorder mentioned herein comprising administering to a subject a pharmaceutically active amount of a compound of formula (I).

Furthermore, compounds of the formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of formula (I) for the preparation of a pharmaceutical composition, optionally for use in combination with one or several immunomodulating agents, for the prevention or treatment of the diseases and disorders mentioned herein.

The compounds of formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the formula (I) of the present invention can be prepared according to the general sequence of reactions outlined below. Only a few of the synthetic possibilities leading to compounds of formula (I) are described.

Preparation of the Compounds According to the Invention

Abbreviations

The following abbreviations are used throughout the specification and the examples:
Ac acetyl
aq. aqueous
atm atmosphere
Boc tert-butoxycarbonyl
BSA bovine serum albumin
CC column chromatography on silica gel
CDI carbonyl diimidazole
DCC dicyclohexyl carbodiimide
DCM dichloromethane
DEAD diethyl azodicarboxylate
DIPEA diisopropyl-ethylamine, Hünig's base, ethyl-diisopropylamine
DMF dimethylformamide
DMSO dimethylsulfoxide
DPPP 1,3-bis-(diphenylphosphino)-propane
EA ethyl acetate
EDC N-(3-dimethylaminopropyl)-N'-ethyl-carbodiimide
eq. equivalent(s)
Et ethyl
h hour(s)
HBTU O-(benzotriazol-1-yl)-N,N,N',N'-tetramethyluronium hexafluorophosphate
Hept heptane
HOBt 1-hydroxybenzotriazole
HPLC high performance liquid chromatography
LC-MS liquid chromatography—mass spectrometry
LiHMDS lithium 1,1,1,3,3,3-hexamethyl-disilazane
Lit. literature
Me methyl
min minute(s)
MPLC medium pressure liquid chromatography
NaOAc sodium acetate
NMP N-methyl-pyrrolidone
OAc acetate
org. organic
Pd(dppf) palladium 1,1'-bis(diphenylphosphino)ferrocene complex
Ph phenyl
PPh$_3$ triphenylphosphine
prep. preparative
PyBOP benzotriazol-1-yl-oxy-tris-pyrrolidino-phosphonium-hexafluoro-phosphate
rac racemic
rt room temperature
sat. saturated
S1P sphingosine 1-phosphate
TBME tert-butyl methyl ether TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
$t_R$ retention time given in minutes
General Preparation Methods:

The compounds of formula (I) wherein $R^1$ represents —$CH_2$—$NR^{1a}R^{1b}$ can be prepared by reacting a compound of Structure 1

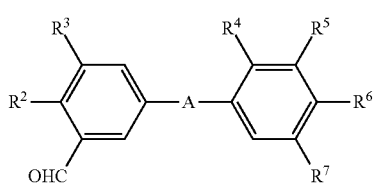

Structure 1 with a compound of Structure 2

Structure 2 in the presence of a reducing agent such as $NaBH_4$, $NaCNBH_3$, $NaBH(CH_3COO)_3$, $LiBH_4$, etc. in a solvent such as MeOH, MeCN, 1,2-dichloroethane, DCM, NMP, THF, etc., or mixtures thereof, at temperatures between rt and the boiling point of the corresponding solvent (Lit.: e.g. D. H. Boschelli et al., J. Med. Chem. 48 (2005) 3891-3902; Abdel-Magid, A. F., J. Org. Chem. 61 (1996), 3849-3862). Alternatively, the above mentioned reductive amination step may also be performed using a compound of Structure 1 and a primary amine $R^{1a}$—$NH_2$ or $R^{1b}$—$NH_2$; The second substitutent $R^{1b}$ or $R^{1a}$ may then be introduced by a subsequent alkylation reaction using a compound $R^{1b}$—X and $R^{1a}$—X, respectively, wherein X represents a reactive group such as a halogen atom e.g. chlorine, bromine or iodine. Such an alkylation reaction may be carried out in a solvent such as THF, dioxane, DMF or mixtures thereof, in the presence of a base such as NaH, LiH, LiHMDS, etc. The nature of the substituent $R^6$ influences the choice between the one-step reductive amination or the two step reductive amination—alkylation procedure.

Compounds of Structure 1 that are a 5-(3-formylphenyl)-[1,2,4]oxadiazole derivatives can be prepared by reacting compounds of Structure 3

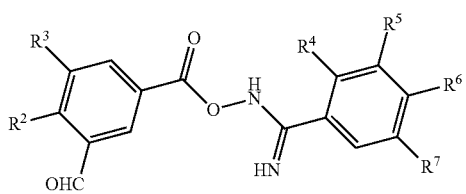

Structure 3 in a solvent such as xylene, toluene, benzene, pyridine, DMF, dichloromethane, acetic acid, TFA, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, TEA, etc.), tetraalkylammonium salts, or water removing agents (e.g. oxalyl chloride, a carboxylic acid anhydride, $POCl_3$, $PCl_5$, $P_4O_{10}$, molecular sieves, etc.) (Lit.: e.g. A. R. Gangloff, J. Litvak, E. J. Shelton, D. Sperandio, V. R. Wang, K. D. Rice, Tetrahedron Lett. 42 (2001), 1441-1443; T. Suzuki, K. Iwaoka, N. Imanishi, Y. Nagakura, K. Miyta, H. Nakahara, M. Ohta, T. Mase, Chem. Pharm. Bull. 47 (1999), 120-122; R. F. Poulain, A. L. Tartar, B. P. Déprez, Tetrahedron Lett. 42 (2001), 1495-1498; R. M. Srivastava, F. J. S. Oliveira, D. S. Machado, R. M. Souto-Maior, Synthetic Commun. 29 (1999), 1437-1450; E. O. John, J. M. Shreeve, Inorganic Chemistry 27 (1988), 3100-3104; B. Kaboudin, K. Navaee, Heterocycles 60 (2003), 2287-2292).

The compounds of Structure 3 can be prepared by reacting compounds of Structure 4

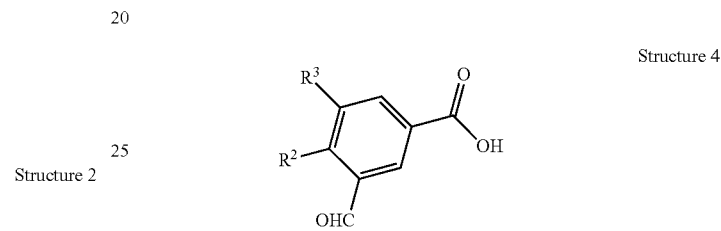

Structure 4 with compounds of Structure 5

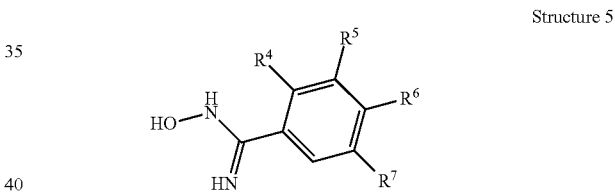

Structure 5 in a solvent such as DMF, THF, etc. in the presence of one or more coupling agents such as TBTU, DCC, EDC, HBTU, HOBt, CDI, etc. and in the presence or absence of a base such as triethylamine, Hünig's base, NaH, $K_2CO_3$, etc. (Lit.: e.g. A. Hamze, J.-F. Hernandez, P. Fulcrand, J. Martinez, J. Org. Chem. 68 (2003) 7316-7321; and the literature cited above).

Compounds of Structure 1 that are 3-(3-formylphenyl)-[1,2,4]oxadiazole derivatives can be prepared in an analogous fashion (Lit.: e.g. C. T. Brain, J. M. Paul, Y. Loong, P. J. Oakley, Tetrahedron Lett. 40 (1999) 3275-3278). Hence, compounds of Structure 1 which represent 3-(3-formylphenyl)-[1,2,4]oxadiazole derivatives can be prepared by reacting compounds of Structure 6

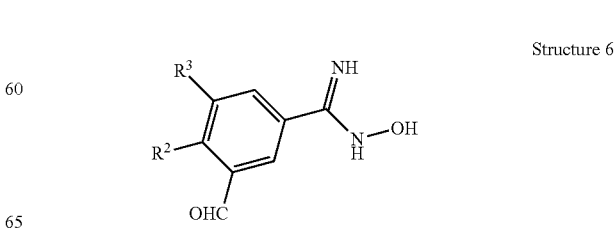

Structure 6 with compounds of Structure 7

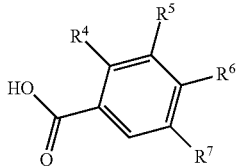

Structure 7

The compounds of Structures 5 and 6 may be prepared by reacting compounds of Structure 8

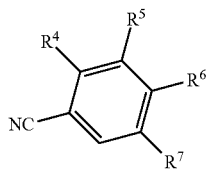

Structure 8 and Structure 9

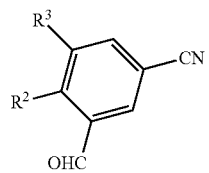

Structure 9 respectively, with hydroxylamine or one of its salts in a solvent such as MeOH, ethanol, pyridine, etc. in the presence or absence of a base such as $Na_2CO_3$, $K_2CO_3$, triethylamine, etc. (Lit.: e.g. T. Suzuki, K. Iwaoka, N. Imanishi, Y. Nagakura, K. Miyta, H. Nakahara, M. Ohta, T. Mase, *Chem. Pharm. Bull.* (1999), 47, 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* (2003), 11, 3379-3392; R. Miller, F. Lang, Z. J. Song, D. Zewge, WO 2004/035538 (Merck & Co., Inc., USA); B. Kaboudin, K. Navaee, *Heterocycles* (2003), 60, 2287-2292). For this step, the aldehyde functionality present in Structure 9 may require temporary protection.

Compounds of Structure 1 that are 2-(3-formylphenyl)-[1,3,4]oxadiazole or 2-(3-formylphenyl)-[1,3,4]thiadiazole derivatives can be prepared similarly by reacting compounds of Structure 4 with hydrazine (by using a coupling reagent such as TBTU, DCC, EDC, HBTU, PyBOP, HOBt, CDI, etc.) to form compounds of Structure 10

Structure 10 which can then be coupled with compounds of Structure 7 to give compounds of Structure 11

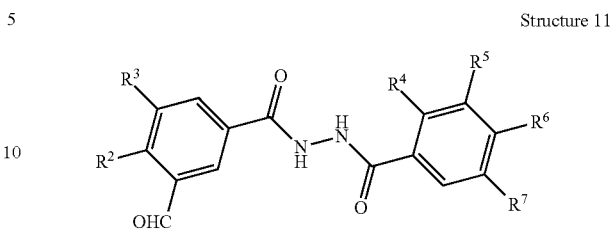

Structure 11

The aldehyde functionality present in Structure 4 may require temporary protection during these manipulations. Compounds of Structure 11 can also be prepared by following the reverse reaction order, i.e. by first coupling compounds of Structure 7 with hydrazine followed by reacting the corresponding hydrazide intermediate with compounds of Structure 4. Dehydration of compounds of Structure 11 to form the desired 2-(3-formylphenyl)-[1,3,4]oxadiazole derivative is affected by treating compounds of Structure 11 with a reagent such as $POCl_3$, $CCl_4$ or $CBr_4$ in combination with triphenylphosphine, $P_2O_5$, Burgess reagent, etc. in a solvent such as toluene, acetonitrile, dioxane, THF, $CHCl_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* (2005), 48, 4068-4075; C. T. Brain, J. M. Paul, Y. Loong, P. J. Oakley, *Tetrahedron Lett.* (1999), 40, 3275-3278). Likewise, 2-(3-formylphenyl)-[1,3,4]thiadiazole derivatives can be obtained by cyclizing compounds of Structure 11 with Lawesson's reagent, optionally in combination with $P_2S_5$, in the presence or absence of a solvent such as pyridine, toluene, THF, acetonitrile, etc. at elevated temperatures with or without microwave irradiation (Lit.: e.g. A. A. Kiryanov, P. Sampson, A. J. Seed, *J. Org. Chem.* (2001), 66, 7925-7929).

Depending on the nature of the functionalities present in the residues $R^4$ to $R^7$, in particular $R^6$, in Structures 1, 3, 5, 7, 8, and 11, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues $R^4$ to $R^7$, in particular $R^6$, may also be introduced in later steps that follow e.g. the reaction of a compound of Structure 4 or 6 with a suitable precursor of a compound of Structure 5 and 7, respectively. In addition, the desired functionalities in $R^4$ to $R^7$, in particular $R^6$, may also be established after the introduction of the $R^{1a}R^{1b}$N-moiety to the diphenyl-oxadiazole or diphenyl-thiadiazole scaffolds. The compounds of Structure 5 and 7, or their precursors are either commercially available or can be prepared according to procedures known to a person skilled in the art. Procedures that effect the transformation of a carboxylic acid of Structure 4 and 7 into a nitrile of Structure 9 and 8, respectively, are known to a person skilled in the art. Protection of the aldehyde functionality present in Structure 4 may precede the transformation of the acid into the nitrile. The protecting group may be cleaved directly after the transformation or at a later stage as convenient.

Alternatively, the $R^{1a}R^{1b}N$-moiety may also be introduced into a compound of Structure 4 already to give a compound of Structure 12

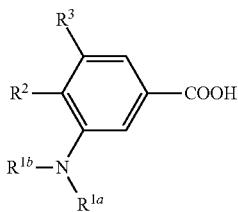

Structure 12 which is then used in the following coupling and cyclisation steps to establish the central oxadiazole or thiadiazole ring.

The compounds of formula (I) wherein $R^2$ represents —$CH_2$—$NR^{2a}R^{2b}$ may be prepared in analogy to the above-described procedure starting from compounds of Structure 13

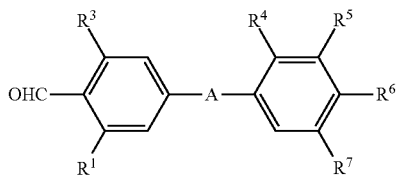

Structure 13 and compounds of Structure 14

Structure 14

As described in the previous sections for compounds of Structure 1, a compound of Structure 13 may be prepared ultimately starting from compound of Structure 15

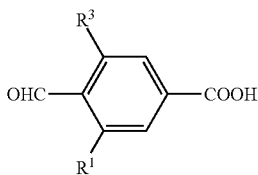

Structure 15

Among the compounds of Structure 4 and 15, 3-formyl-benzoic acid and 4-formylbenzoic acid are commercially available.

3-formyl-4-alkoxy-benzoic acids can be prepared in analogy to literature procedures (e.g. P. Molina; M. Alajarin; A. Vidal, *Synthesis* 1992, 293-296) from commercially available ethyl 4-hydroxybenzoate. 4-Alkoxy-3-formyl-5-methyl benzoic acids may be prepared in an analogous fashion starting from commercially available 4-hydroxy-3-methylbenzoic acid methyl ester.

3-formyl-4-alkyl-benzoic acids can be prepared starting from commercially available 4-bromo-3-methyl-benzoic acid methyl ester which can be oxidised according to literature procedures (e.g. O. Miyata et al. *Synlett* 2006, 893-896) to give 3-formyl-4-bromobenzoic acid methyl ester. This compounds can then be treated with the appropriate alkenyl boron derivative (e.g. 2,4,6-trivinyl-cyclotriboroxane) under Suzuki conditions (Lit.: e.g. F. Kerins, D. F. O'Shea, *J. Org. Chem.* (2002), 67, 4968-4971) followed by catalytic hydrogenation and subsequent ester cleavage to give the desired 3-formyl-4-alkyl-benzoic acid. Alternatively, the alkyl group, in particular a methyl group, may also be introduced using the appropriate alkyl-Zn reagents under Negishi conditions (e.g. H. Matsushita, E. Negishi, *J. Org. Chem.* (1982), 47, 4161-4165). The 3-formyl-group may require protection, e.g. as an acetal, during these transformations.

3-formyl-5-alkoxy-benzoic acids can be prepared in analogy to literature procedures (e.g. H. Zhao, A. Thurkauf, *Synthetic Communications* (2001), 31, 1921-1926) from commercially available 5-hydroxy-1,3-benzenedicarboxylic acid dimethyl ester.

In general, 5-alkyl-3-formyl-benzoic acids may be prepared from 5-bromo-3-formyl-benzoic acid which in turn is prepared from 3-formyl-benzoid acid according to literature procedures (e.g. D. Zhao, J. S. Moore, *J. Org. Chem.* (2002), 67, 3548-3554). Thus, a 5-bromo-3-formyl-benzoic acid ester is reacted with the appropriate alkenyl boron derivative (e.g. 2,4,6-trivinyl-cyclotriboroxane) under Suzuki conditions (Lit.: e.g. F. Kerins, D. F. O'Shea, *J. Org. Chem.* (2002), 67, 4968-4971) followed by catalytic hydrogenation and subsequent ester cleavage to give the desired 5-alkyl-3-formyl-benzoic acid. Alternatively, the alkyl group may also be introduced using the appropriate alkyl-Zn reagents under Negishi conditions (e.g. H. Matsushita, E. Negishi, *J. Org. Chem.* (1982), 47, 4161-4165). The 3-formyl-group may require protection e.g. as an acetal during these transformations. More specifically, 5-methyl-3-formyl-benzoic acid may be prepared by brominating 3,5-dimethylbenzoic acid using $Br_2$ in the presence of 2,2'-azo-bis-isobutyronitrile (Lit. e.g. Y. Sawada, et al. *J. Pesticide Sci.* (2002), 27, 365-373) to give 3-bromomethyl-5-methyl-benzoic acid which is then oxidised with $MnO_2$ (Lit. e.g. S. Goswami, et al. *Chem. Letters* 34 (2005), 194-195) to give the desired 5-methyl-3-formyl-benzoic acid.

5-alkyl-3-formyl-benzoic acids may also be prepared by reacting 1,3-dibromo-5-alkyl benzene with Mg followed by $CO_2$ to give the corresponding 3-bromo-5-alkyl-benzoic acid (lit. e.g. R. Cosmo; S. Sternhell; *Austr. J. Chem.* (1987), 40, 1107-26). After esterification the resulting 3-bromo-5-alkyl-benzoic acid ester can then be treated with butyl lithium followed by DMF (Lit. e.g. A. S. Kende; M. Zhong *Synthetic Commun.* (1999), 29, 3401-3407) to give the corresponding 5-alkyl-3-formyl-benzoic acid ester which is then hydrolysed to the desired 5-alkyl-3-formyl-benzoic acid.

3-alkoxy-4-formyl-benzoic acids can be prepared by treating commercially available 4-formyl-3-hydroxybenzoic acid with an appropriate alkylating agent such as methyl iodide, ethyl iodid, isopropyl bromide, etc. in the presence of a base such as $K_2CO_3$, $Cs_2CO_3$, etc. in analogy to literature procedures (e.g. Z. B. Fei, F. E. McDonald, *Organic Letters* (2007), 9, 3547-3550) to give the corresponding 3-alkoxy-4-formyl-benzoic acid alkyl ester which can then be cleaved to the desired 3-alkoxy-4-formyl-benzoic acid. In some instances it may be beneficial to esterify 4-formyl-3-hydroxybenzoic acid prior to the alkylation step to allow for more versatility of the synthesis.

The preparation of 4-formyl-5-methyl-5-alkoxy-benzoic acid may start by preparing 3-hydroxy-5-methyl-benzoic acid according to literature procedures (e.g. T. Lu, et al. *Bioorg. Med. Chem. Letters* (2004), 14, 3727-3731). The benzoic acid is then esterified and alkylated either in a onestep-one-pot procedure or in a two-step procedure to give an appropriate 3-alkoxy-5-methyl-benzoic acid ester. The ester is then saponified again before the resulting 3-alkoxy-5-methyl-benzoic acid is formylated by treating it with potassium tert-butoxide and butyl lithium followed by DMF at low temperature in THF in analogy to a literature procedure (e.g. S. Sinha; B. Mandel; S. Chandrasekaran; *Tetrahedron Letters* (2000), 41, 3157-3160) to give the desired 4-formyl-5-methyl-5-alkoxy-benzoic acid.

4-formyl-3-methyl-benzoic acid, 4-formyl-3-ethyl-benzoic acid and 4-formyl-3,5-dimethyl-benzoic acid can be prepared from commercially available 4-bromo-3-methyl-benzoic acid, 4-bromo-3-ethyl-benzoic acid and 4-bromo-3,5-dimethyl-benzoic acid, respectively, by treating the corresponding tert-butyl esters with butyl lithium followed by DMF in analogy to literature procedures (e.g. A. S. Kende; M. Zhong, *Synthetic Commun*. (1999), 29, 3401-3407).

A more general access to 3-alkyl-4-formyl-benzoic acids is given in the following section: Commercially available 2-bromo-terephthalic acid or 2-bromo-terephthalic acid dimethyl ester is transformed to 2-bromo-terephthalaldehyde via a reduction-oxidation sequence in analogy to litereture procedures (e.g. K. R. Roesch, H. Zhang, R. C. Larock, *J. Org. Chem*. (2001), 66, 8042-8051 (supporting information); T. Ise, D. Shiomi, K. Sato, T. Takui, *Chemistry of Materials* (2005), 17, 4486-4492; S, Narsimhan, K. G. Prasad, S. Madhavan, *Synthetic Commun*. (1995), 25, 1689-1697). 2-Bromo-terephthalaldehyde is then subjected to a Cannizzaro reaction according to a literature procedure (S. E. Hazlet, G. Bosmajian, J. H. Estes, E. F. Tallyn, *J. Org. Chem*. (1964), 29, 2034-2036) to give 3-bromo-4-hydroxymethyl-benzoic acid which is then oxidised for instance by treatment with $MnO_2$ (lit. e.g. T. Ise, D. Shiomi, K. Sato, T. Takui, *Chemistry of Materials* (2005), 17, 4486-4492; S. Goswami, et al. *Chem. Letters* (2005), 34, 194-195) to 3-bromo-4-formyl-benzoic acid. This compound is then elaborated to the desired 3-alkyl-4-formyl-benzoic acid by either treating it with the appropriate alkenyl boron derivative (e.g. 2,4,6-trivinyl-cyclotriboroxane) under Suzuki conditions (Lit.: e.g. F. Kerins, D. F. O'Shea, *J. Org. Chem*. (2002), 67, 4968-4971) followed by catalytic hydrogenation or by reacting it with the appropriate alkyl-Zn reagents under Negishi conditions (e.g. H. Matsushita, E. Negishi, *J. Org. Chem*. (1982), 47, 4161-4165). The 4-formyl-group and the carboxylic acid function may require protection e.g. as an acetal and ester, respectively, during these transformations.

4-formyl-3-alkyl-5-methyl benzoic acids can be prepared starting from commercially available 3,5-dibromo-4-methyl-benzoic acid or one of its esters. Thus, 3,5-dibromo-4-methyl-benzoic acid methyl ester is brominated using N-bromosuccinimide in $CCl_4$ (according to e.g. J. B. Doherty, et al., WO 02/058695 (Merck & Co), p. 125) to give 3,5-dibromo-4-bromomethyl-benzoic acid methyl ester which is then transformed to 3,5-dibromo-4-formyl-benzoic acid methyl ester in analogy to literature procedures (e.g. S. Goswami, et al. *Chem. Letters* (2005), 34, 194-195). This compound can then be transformed to the desired 4-formyl-3-alkyl-5-methyl benzoic acid by making use of the above mentioned Suzuki and/or Negishi reactions using the appropriate alkenyl boron derivative and alkyl-Zn reagent, respectively.

The following examples illustrate the invention but do not at all limit the scope thereof.

EXAMPLES

All temperatures are stated in ° C. Compounds were characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, h=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% MeCN in water, 1 min, with 0.04% TFA, flow: 4.5 mL/min), $t_R$ is given in min; retention times or LC-MS marked with * refer to LC run under basic conditions, i.e. eluting with a gradient of MeCN in water containing 13 mM of ammonium hydroxide, otherwise identical conditions; retention times or LC-MS marked with ** refer to a LC run under the following conditions: column: Zorbax Extended C18, 1.8 µM, 4.6×20 mm, gradient: 5-95% MeCN in water, 1 min, with 0.04% TFA, flow: 4.5 mL/min; by TLC (TLC-plates from Merck, Silica gel 60 $F_{254}$); or by melting point. Compounds were purified by prep. HPLC (column: X-terra RP18, 50×19 mm, 5 µm, gradient: 10-95% MeCN in water containing 0.5% of formic acid) or by MPLC (Labomatic MD-80-100 pump, Linear UVIS-201 detector, column: 350× 18 mm, Labogel-RP-18-5s-100, gradient: 10% MeOH in water to 100% MeOH).

3-ethyl-4-hydroxy-5-methyl-benzonitrile

The title compound is prepared from 3-ethyl-4-hydroxy-5-methyl-benzaldehyde following literature procedures (A. K. Chakraborti, G. Kaur, *Tetrahedron* (1999), 55, 13265-13268). LC-MS: $t_R$=0.90 min; $^1$H NMR ($CDCl_3$): δ 1.24 (t, J=7.6 Hz, 3H), 2.26 (s, 3H), 2.63 (q, J=7.6 Hz, 2H), 5.19 (s, 1H), 7.30 (s, 2H).

3-chloro-4-hydroxy-5-methyl-benzonitrile

The title compound is prepared from commercially available 2-chloro-6-methyl-phenol in analogy to literature procedures (see 3-ethyl-4-hydroxy-5-methyl-benzonitrile). LC-MS: $t_R$=0.85 min. $^1$H NMR ($CDCl_3$): δ2.33 (s, 3H), 6.10 (s, 1H), 7.38 (s, 1H), 7.53 (d, J=1.8 Hz, 1H).

4-hydroxy-3-methoxy-5-methyl-benzonitrile

The title compound is prepared from commercially available 2-hydroxy-3-methoxy-toluene in analogy to literature procedures (see 3-ethyl-4-hydroxy-5-methyl-benzonitrile). LC-MS: $t_R$=0.84 min. $^1$H NMR ($CDCl_3$): δ 2.27 (s, 3H), 3.93 (s, 3H), 6.24 (s, 1H), 6.97 (d, J=1.3 Hz, 1H), 7.12 (s, 1H).

3-chloro-4-hydroxy-5-methoxy-benzonitrile

The title compound is prepared from commercially available 3-chloro-4-hydroxy-5-methoxy-benzaldehyde in analogy to literature procedures (see 3-ethyl-4-hydroxy-5-methyl-benzonitrile). LC-MS: $t_R$=0.82 min; $^1$H NMR ($CDCl_3$): δ3.98 (s, 3H), 6.36 (s, 1H), 7.04 (s, 1H), 7.34 (s, 1H).

4-hydroxy-2-methoxy-benzonitrile

The title compound is prepared from commercially available 4-hydroxy-2-methoxy-benzaldehyde in analogy to literature procedures (see 3-ethyl-4-hydroxy-5-methyl-benzonitrile). LC-MS: $t_R$=0.74 min. $^1$H NMR ($D_6$-DMSO): δ 3.84 (s, 3H), 6.47 (d, J=8.5 Hz, 1H), 6.54 (s, 1H), 7.49 (d, J=8.5 Hz, 1H), 10.60 (s, 1H).

4-hydroxy-2-methyl-benzonitrile

A solution of 4-methoxy-2-methylbenzonitrile (5.0 g, 33.97 mmol) in DCM (150 mL) is cooled down to 0° C.

before adding dropwise a 1M solution of BBr$_3$ in DCM (136 mL, 136 mmol). The reaction mixture is allowed to reach rt and stirring is then continued at 45° C. for 5 days. Ice water (500 mL) is then added and the reaction mixture is stirred for 1 h before sat. aq. NaHCO$_3$ (250 mL) is added. The mixture is extracted with DCM (200 mL then 4×100 mL) and the combined org. extracts are dried over MgSO$_4$, filtered and evaporated to give the title compound as a brown solid (4.7 g). LC-MS: $t_R$=0.76 min. $^1$H NMR (D$_6$-DMSO): δ 2.38 (s, 3H), 6.73 (dd, J=8.5, 2.0 Hz, 1H), 6.79 (d, J=2.0 Hz, 1H), 7.55 (d, J=8.5 Hz, 1H), 10.49 (s, 1H).

4,N-dihydroxy-3,5-dimethyl-benzamidine

The title compound was prepared from commercially available 4-hydroxy-3,5-dimethyl-benzonitrile according to literature procedures (e.g. E. Meyer, A. C. Joussef, H. Gallardo, *Synthesis* 2003, 899-905). $^1$H NMR (CD$_3$OD): δ 7.20 (s, 2H), 2.20 (s, 6H).

3-ethyl-4,N-dihydroxy-5-methyl-benzamidine

The title compound is prepared from commercially available 2-ethyl-6-methyl-phenol (or vide infra) following literature procedures (G. Trapani, A. Latrofa, M. Franco, C. Altomare, E. Sanna, M. Usala, G. Biggio, G. Liso, *J. Med. Chem.* (1998), 41, 1846-1854; A. K. Chakraborti, G. Kaur, *Tetrahedron* (1999), 55, 13265-13268; E. Meyer, A. C. Joussef, H. Gallardo, *Synthesis* 2003, 899-905). LC-MS: $t_R$=0.55 min; $^1$H NMR (D$_6$-DMSO): δ 9.25 (br s, 1H), 7.21 (s, 2H), 5.56 (s, 2H), 2.55 (q, J=7.6 Hz, 2H), 2.15 (s, 3H), 1.10 (t, J=7.6 Hz, 3H).

4,N-dihydroxy-3-methyl-5-propyl-benzamidine

The title compound is prepared from commercially available 2-methyl-6-propyl-phenol in analogy to literature procedures (e.g. B. Roth et al., *J. Med. Chem.* (1988), 31, 122-129; and literature cited for 3-ethyl-4,N-dihydroxy-5-methyl-benzamidine). LC-MS: $t_R$=0.54 min; [M+1]$^+$=209.43; $^1$H NMR (D$_6$-DMSO): δ 0.90 (t, J=7.3 Hz, 3H), 1.48-1.59 (m, 3H), 2.19 (s, 3H), 2.56 (t, J=7.3 Hz, 2H), 7.37 (s, 1H), 7.40 (s, 1H), 9.34 (s, 1H).

3-chloro-4,N-dihydroxy-5-methyl-benzamidine

The title compound is prepared from commercially available 2-chloro-6-methyl-phenol in analogy to literature procedures (e.g. B. Roth et al., *J. Med. Chem.* (1988), 31, 122-129; and literature cited for 3-ethyl-4,N-dihydroxy-5-methyl-benzamidine). 3-chloro-4-hydroxy-5-methyl-benzaldehyde: LC-MS: $t_R$=0.49 min; [M+1]$^+$=201.00; $^1$H NMR (CDCl$_3$): δ 2.24 (s, 2H), 2.35 (s, 4H), 5.98 (br s, 1H), 7.59 (d, J=1.8 Hz, 1H), 7.73 (d, J=1.8 Hz, 1H), 9.80 (s, 1H); 3-chloro-4,N-dihydroxy-5-methyl-benzamidine: $^1$H NMR (D$_6$-DMSO): δ 2.21 (s, 3H), 5.72 (br s, 2H), 7.40 (s, 1H), 7.48 (s, 1H), 9.29 (br s, 1H), 9.48 (br s, 1H).

4,N-dihydroxy-2-methoxy-benzamidine

The title compound is prepared from commercially available 4-hydroxy-2-methoxybenzaldehyde in analogy to literature procedures (see 3-ethyl-4,N-dihydroxy-5-methyl-benzamidine). LC-MS: $t_R$=0.41 min; [M+1]$^+$=183.06; $^1$H NMR (D$_6$-DMSO): δ 3.74 (s, 3H), 5.47 (s, 2H), 6.35 (dd, J=8.3, 1.5 Hz, 1H), 6.45 (s, 1H), 7.21 (d, J=8.5 Hz, 1H), 9.42 (s, 2H).

3-[2-ethyl-4-(N-hydroxycarbamimidoyl)-6-methyl-phenyl]-propionic acid a) To an ice-cooled solution of 5-ethyl-4-hydroxy-3-methylbenzaldehyde (10.0 g, 60.9 mmol) in DCM (50 mL) and pyridine (15 mL), trifluoromethanesulfonic acid anhydride (18.9 g, 67 mmol) was added over a period of 20 min. Upon complete addition, the ice bath was removed and the reaction was stirred for further 2 h at rt. The mixture was diluted with DCM (150 mL), washed three times with water, dried over MgSO$_4$, filtered and evaporated. The residue was purified by CC eluting with Hept:EA 9:1 to give trifluoro-methanesulfonic acid 2-ethyl-4-formyl-6-methyl-phenyl ester as a pale yellow oil (10.75 g). LC-MS: $t_R$=1.07 min; $^1$H NMR (CDCl$_3$): δ 9.98 (s, 1H), 7.70 (s, 1H), 7.66 (s, 1H), 2.85 (q, J=10.1 Hz, 2H), 2.48 (s, 3H), 1.30 (t, J=10.2 Hz, 3H).

b) To a stirred solution of the above triflate (10.7 g, 36.1 mmol) in dry DMF (75 mL) were sequentially added TEA (7.3 g, 72.2 mmol), methyl acrylate (31.1 g, 361 mmol), DPPP (819 mg, 1.99 mmol) and Pd(OAc)$_2$ (405 mg, 1.81 mmol) under nitrogen. The mixture was stirred at 115° C. for 5 h, cooled to rt, diluted with Et$_2$O (350 mL) and washed twice with 1 N aq. HCl and once with sat. aq. NaHCO$_3$ solution. The org. extract was dried over MgSO$_4$, filtered and evaporated. The residue was purified by CC eluting with Hept:EA 19:1 to give 3-(2-ethyl-4-formyl-6-methyl-phenyl)-acrylic acid methyl ester as a colourless liquid (5.93 g). LC-MS: $t_R$=0.99 min.

c) A suspension of 3-(2-ethyl-4-formyl-6-methyl-phenyl)-acrylic acid methyl ester (5.93 g, 25.53 mmol) in MeOH (140 mL) and 2 N aq. NaOH (45 mL) was stirred at rt for 1 h. The MeOH was evaporated and the aq. solution was extracted twice with DCM. The aq. layer was acidified with 37% aq. HCl. The precipitate that formed was collected, washed with water and dried. The product was further purified by recrystallisation from EA (100 mL) to give 3-(2-ethyl-4-formyl-6-methyl-phenyl)-acrylic acid as yellow crystals (4.2 g). LC-MS: $t_R$=0.87 min.

d) To a solution of 3-(2-ethyl-4-formyl-6-methyl-phenyl)-acrylic acid (2.75 g, 12.6 mmol) and DIPEA (1.8 g, 13.8 mmol) in ethanol (80 mL), Pd/C (275 mg, 10% Pd, moistened with 50% water) was added. The mixture was stirred for 16 h at rt under 1 atm of H$_2$. The catalyst was filtered off and the filtrate was concentrated. The residue was dissolved in EA and washed with 2 N aq. HCl, followed by 1 N aq. HCl and brine. The org. extract was dried over Na$_2$SO$_4$, filtered and evaporated to give 3-(2-ethyl-4-hydroxymethyl-6-methyl-phenyl)-propionic acid as a white solid (2.8 g). LC-MS: $t_R$=0.76 min.

e) A solution of 3-(2-ethyl-4-hydroxymethyl-6-methyl-phenyl)-propionic acid (2.8 g, 12.6 mmol) in AcOH (50 mL) was treated with MnO$_2$ (3.9 g, 45.4 mmol) and the resulting mixture was stirred at 80° C. for 4 h. The mixture was filtered and the filtrate was concentrated. The crude product was purified by CC eluting with DCM to give 3-(2-ethyl-4-formyl-6-methyl-phenyl)-propionic acid as a beige solid (1.76 g). LC-MS: $t_R$=0.86 min.

f) A solution of 3-(2-ethyl-4-formyl-6-methyl-phenyl)-propionic acid (1.67 g, 7.58 mmol) and hydroxylamine hydrochloride (780 mg, 11.36 mmol) in 1-methyl-2-pyrrolidone was heated to 80° C. for 30 min in the microwave (300 W, active cooling during irradiation). The reaction mixture was diluted with Et$_2$O and washed with water and brine. The org. extract was dried over Na$_2$SO$_4$, filtered and evaporated to give 3-(4-cyano-2-ethyl-6-methyl-phenyl)-propionic acid as a beige solid (1.55 g). LC-MS: $t_R$=0.89 min, $^1$H NMR (D$_6$-

DMSO): δ 12.25 (s, 1H), 7.45 (s, 2H), 2.91-2.84 (m, 2H), 2.67-2.59 (m, 2H), 2.35-2.30 (m, 5H), 1.14 (t, J=7.6 Hz, 3H).

g) Potassium tert-butoxide (2.71 g, 24.1 mmol) was carefully dissolved in MeOH (25 mL). To this solution hydroxylamine hydrochloride (1.44 g, 20.7 mmol) followed by 3-(4-cyano-2-ethyl-6-methyl-phenyl)-propionic acid (1.50 g, 6.90 mmol) dissolved in MeOH (7.5 mL) was added. The mixture was refluxed for 8 h and the solvent was evaporated. The residue was dissolved in 2 N aq. HCl and extracted with EA. The pH of the aq. phase was adjusted to pH 5 by adding sat. aq. NaHCO$_3$ and the mixture was extracted three times with EA. The combined org. extracts were dried over Na$_2$SO$_4$, filtered, evaporated and dried to give 3-[2-ethyl-4-(N-hydroxycarbamimidoyl)-6-methyl-phenyl]-propionic acid as a white solid (1.4 g). LC-MS: $t_R$=0.60 min, [M+1]$^+$=251.17.

3-[4-(N-hydroxycarbamimidoyl)-2,6-dimethyl-phenyl]-propionic acid

The title compound was prepared in analogy to 3-[2-ethyl-4-(N-hydroxycarbamimidoyl)-6-methyl-phenyl]-propionic acid starting from 3,5-dimethyl-4-hydroxybenzaldehyde. LC-MS: $t_R$=0.57 min, [M+1]$^+$=237.02; $^1$H NMR (D$_6$-DMSO): δ2.29 (s, 6H), 2.30-2.36 (m, 2H), 2.80-2.87 (m, 2H), 5.66 (s, 2H), 7.30 (s, 2H), 9.46 (s, 1H).

4-bromo-2-ethyl-6-methyl-aniline

The title compound was prepared from commercially available 2-ethyl-6-methyl-aniline following literature procedures (R. A. Benkeser, R. A. Hickner, D. I. Hoke, O. H. Thomas, *J. Am. Chem. Soc.* (1958), 80, 5289-5293). $^1$H NMR (CDCl$_3$): δ 1.27 (t, J=7.3 Hz, 3H), 2.18 (s, 3H), 2.51 (q, J=7.3 Hz, 2H), 3.61 (s br, 2H), 7.09 (s, 2H).

4-amino-3-ethyl-5-methyl-benzonitrile

The title compound was prepared from 4-bromo-2-ethyl-6-methyl-aniline following literature procedures (J. Zanon, A. Klapars, S. Buchwald, *J. Am. Chem. Soc.* (2003), 125, 2890-2891). $^1$H NMR (CDCl$_3$): δ 1.29 (t, J=7.5 Hz, 3H), 2.19 (s, 3H), 2.52 (q, J=7.5 Hz, 2H), 4.10 (br s, 2H), 7.25 (s br, 2H).

4-bromo-3-ethyl-5-methyl-benzonitrile

The title compound was prepared from 4-amino-3-ethyl-5-methyl-benzonitrile and copper(II) bromide following literature procedures (M. P. Doyle, B. Siegfried, J. F. Dellaria Jr., *J. Org. Chem.* (1977), 42, 2426-2429). $^1$H NMR (CDCl$_3$): δ 1.26 (t, J=7.5 Hz, 3H), 2.47 (s, 3H), 2.83 (q, J=7.5 Hz, 2H), 7.36 (s, 1H), 7.37 (s, 1H).

3-(4-cyano-2-ethyl-6-methyl-phenyl)-propionic acid ethyl ester

The title compound was prepared from 4-bromo-3-ethyl-5-methyl-benzonitrile and commercially available acrolein diethyl acetal following literature procedures (G. Battistuzzi, S. Cacchi, G. Fabrizi, R. Bernini, *Synlett* (2003), 8, 1133-1136). LC-MS: $t_R$=0.91 min; $^1$H NMR (CDCl$_3$): δ 1.2 (m, 6H), 2.38 (s, 3H), 2.44 (m, 2H), 2.70 (q, J=7.5 Hz, 2H), 3.03 (m, 2H), 4.18 (q, J=7.3 Hz, 2H), 7.30 (s, 1H), 7.34 (s, 1H).

3-[2-ethyl-4-(N-hydroxycarbamimidoyl)-6-methyl-phenyl]-propionic acid ethyl ester 3-(4-cyano-2-ethyl-6-methyl-phenyl)-propionic acid ethyl ester was transformed to the corresponding hydroxyamidine according to literature procedures using TEA as base (e.g. E. Meyer, A. C. Joussef, H. Gallardo, *Synthesis* 2003, 899-905). LC-MS: $t_R$=0.77 min; [M+1]$^+$=279.52; $^1$H NMR (D$_6$-DMSO): δ 1.19 (m, 6H), 2.29 (s, 3H), 2.41 (m, 2H), 2.62 (q, J=7.5 Hz, 2H), 2.88 (m, 2H), 4.09 (q, J=7.0 Hz, 2H), 5.68 (br s, 2H), 7.31 (s, 1H), 7.33 (s, 1H), 9.47 (s, 1H).

rac-4-(2,2-dimethyl-[1,3]dioxolan-4-ylmethoxy)-N-hydroxy-3,5-dimethyl-benzamidine a) To a solution of 3,5-dimethyl-4-hydroxy-benzonitrile (5.0 g, 34.0 mmol) in THF (40 mL), rac-(2,2-dimethyl-[1,3]dioxolan-4-yl)-MeOH (4.49 g, 34.0 mmol) followed by PPh$_3$ (13.4 g, 50.9 mmol) was added. The mixture was cooled with an ice-bath before DEAD (8.87 g, 50.9 mmol, 23.4 mL of a 40% solution in toluene) was added dropwise. The mixture was stirred at rt for 1 h, the solvent was removed in vacuo and the residue was purified by CC eluting with Hept:EA 99:1 to 92:8 to give rac-4-(2,2-dimethyl-[1,3]dioxolan-4-ylmethoxy)-3,5-dimethyl-benzonitrile as a pale yellow oil (7.20 g). LC-MS: $t_R$=0.99 min, [M+1]$^+$=not detected.

b) To a solution of potassium tert-butylate (6.18 g, 55.1 mmol) in MeOH (125 mL), hydroxylamine hydrochloride (5.74 g, 82.7 mmol) was added. To this solution, a solution of rac-4-(2,2-dimethyl-[1,3]dioxolan-4-ylmethoxy)-3,5-dimethyl-benzonitrile (7.20 g, 27.6 mmol) in MeOH (40 mL) was added. The mixture was refluxed for 72 h before the solvent was removed in vacuo. The residue was purified by prep. HPLC (XBridge Prep C18, 30×75 mm, 5 μm, 2-95% acetonitrile in water containing 0.5% sat. aq. NH$_3$) to give the title compound as a pale yellow solid (4.85 g). LC-MS: $t_R$=0.67 min, [M+1]$^+$=295.06; $^1$H NMR (CDCl$_3$): δ1.43 (s, 3H), 1.48 (s, 3H), 2.29 (s, 6H), 3.76-3.81 (m, 1H), 3.83-3.88 (m, 1H), 3.93-3.99 (m, 1H), 4.17-4.23 (m, 1H), 4.47-4.54 (m, 1H), 5.02 (br s, 1H), 7.28 (s, 2H).

(R)-3-chloro-4-(2,2-dimethyl-[1,3]dioxolan-4-ylmethoxy)-N-hydroxy-5-methyl-benzamidine The title compound is obtained as a colorless oil (1.39 g) in analogy to rac-4-(2,2-dimethyl-[1,3]dioxolan-4-ylmethoxy)-N-hydroxy-3,5-dimethyl-benzamidine starting from 3-chloro-4-hydroxy-5-methyl-benzonitrile and L-α,β-isopropylidene glycerol. LC-MS: $t_R$=0.66 min, [M+H]$^+$=314.96.

(R)-4-(2,2-dimethyl-[1,3]dioxolan-4-ylmethoxy)-N-hydroxy-3-methoxy-5-methyl-benzamidine The title compound is obtained as a beige oil (1.16 g) in analogy to rac-4-(2,2-dimethyl-[1,3]dioxolan-4-ylmethoxy)-N-hydroxy-3,5-dimethyl-benzamidine starting from 4-hydroxy-3-methoxy-5-methyl-benzonitrile and L-α,β-isopropylidene glycerol. LC-MS: $t_R$=0.65 min, [M+H]$^+$=311.0.

(R)-3-chloro-4-(2,2-dimethyl-[1,3]dioxolan-4-ylmethoxy)-N-hydroxy-5-methoxy-benzamidine The title compound is prepared in analogy to rac-4-(2,2-dimethyl-[1,3]dioxolan-4-ylmethoxy)-N-hydroxy-3,5-dimethyl-benzamidine starting from 3-chloro-4-hydroxy-5-methoxy-benzonitrile and L-α,β-isopropylidene glycerol. LC-MS: $t_R$=0.42 min, [M+H]$^+$=331.17; $^1$H NMR (D$_6$-DMSO): δ 1.30 (s, 3H), 1.34 (s, 3H), 3.86 (s, 3H), 3.87-3.93 (m, 2H), 4.00-4.12 (m, 2H), 4.36 (quint, J=5.8 Hz, 1H), 5.90 (s, 2H), 7.32 (d, J=2.0 Hz, 1H), 7.34 (d, J=2.0 Hz, 1H), 9.71 (s, 1H).

(R)-4-(2,2-dimethyl-[1,3]dioxolan-4-ylmethoxy)-N-hydroxy-2-methoxy-benzamidine The title compound is obtained as a beige oil (2.46 g) in analogy to rac-4-(2,2-dimethyl-[1,3]dioxolan-4-ylmethoxy)-N-hydroxy-3,5-dimethyl-benzamidine starting from 4-hydroxy-2-methoxy-benzonitrile and L-α,β-isopropylidene glycerol. LC-MS: $t_R$=0.62 min, [M+H]$^+$=296.97.

(S)-4-(3-amino-2-hydroxypropoxy)-3-ethyl-5-methylbenzonitrile a) To a solution of 3-ethyl-4-hydroxy-5-methyl-benzonitrile (5.06 g, 31.4 mmol) in THF (80 mL), PPh$_3$ (9.06 g, 34.5 mmol) and (R)-glycidol (2.29 mL, 34.5 mmol) were added. The mixture was cooled to 0° C. before DEAD in toluene (15.8 mL, 34.5 mmol) was added. The mixture was stirred for 18 h while warming up to rt. The solvent was evaporated and the crude product was purified by CC eluting with Hept:EA 7:3 to give 3-ethyl-5-methyl-4-oxiranylmethoxy-benzonitrile as a yellow oil (5.85 g). LC-MS: $t_R$=0.96 min; [M+42]$^+$=259.08.

b) The above epoxide was dissolved in 7 N NH$_3$ in MeOH (250 mL) and the solution was stirred at 65° C. for 18 h. The solvent was evaporated to give crude (S)-4-(3-amino-2-hydroxypropoxy)-3-ethyl-5-methylbenzonitrile as a yellow oil (6.23 g). LC-MS: $t_R$=0.66 min; [M+1]$^+$=235.11.

N—((S)-3-[2-ethyl-4-(N-hydroxycarbamimidoyl)-6-methyl-phenoxy]-2-hydroxy-propyl)-2-hydroxy-acetamide a) To a solution of (S)-4-(3-amino-2-hydroxypropoxy)-3-ethyl-5-methylbenzonitrile (6.23 g, 26.59 mmol), glycolic acid (2.43 g, 31.9 mmol), HOBt (4.31 g, 31.9 mmol), and EDC hydrochloride (6.12 g, 31.9 mmol) were added. The mixture was stirred at rt for 18 h before it was diluted with sat. aq. NaHCO$_3$ and extracted twice with EA. The combined org. extracts were dried over MgSO$_4$, filtered and concentrated. The crude product was purified by CC with DCM containing 8% of MeOH to give (S)—N-[3-(4-cyano-2-ethyl-6-methyl-phenoxy)-2-hydroxy-propyl]-2-hydroxy-acetamide as a yellow oil (7.03 g). LC-MS: $t_R$=0.74 min; [M+1]$^+$=293.10; $^1$H NMR (CDCl$_3$): δ 1.25 (t, J=7.5 Hz, 3H), 2.32 (s, 3H), 2.69 (q, J=7.5 Hz, 2H), 3.48-3.56 (m, 3H), 3.70-3.90 (m, 3H), 4.19 (br s, 3H), 7.06 (m, 1H), 7.36 (s, 1H), 7.38 (s, 1H).

b) The above nitrile was converted to the N-hydroxy-benzamidine according to literature procedures (e.g. E. Meyer, A. C. Joussef, H. Gallardo, *Synthesis* 2003, 899-905). LC-MS: $t_R$=0.51 min; [M+1]$^+$=326.13; $^1$H NMR (D$_6$-DMSO): δ 1.17 (t, J=7.4 Hz, 3H), 2.24 (s, 3H), 2.62 (q, J=7.4 Hz, 2H), 3.23 (m, 1H), 3.43 (m, 1H), 3.67 (m, 2H), 3.83 (s, 2H), 3.93 (m, 1H), 5.27 (br s, 1H), 5.58 (br s, 1H), 5.70 (s, 2H), 7.34 (s, 1H), 7.36 (s, 1H), 7.67 (m, 1H), 9.46 (br s, 1H).

rac-2-hydroxy-N-{2-hydroxy-3-[4-(N-hydroxycarbamimidoyl)-2,6-dimethyl-phenoxy]-propyl}-acetamide The title compound was prepared in analogy to N—((S)-3-[2-ethyl-4-(N-hydroxycarbamimidoyl)-6-methyl-phenoxy]-2-hydroxy-propyl)-2-hydroxy-acetamide. LC-MS: $t_R$=0.48 min, [M+1]$^+$=312.05; $^1$H NMR (D$_6$-DMSO): δ 2.21 (s, 6H), 3.14-3.25 (m, 1H), 3.35-3.46 (m, 1H), 3.60-3.69 (m, 2H), 3.80 (s, 2H), 3.85-3.94 (m, 1H), 5.69 (s br, 2H), 7.30 (s, 2H), 7.63 (t, J=5.6 Hz, 1H), 8.11 (s, 1H).

(S)-2-hydroxy-N-{2-hydroxy-3-[4-(N-hydroxycarbamimidoyl)-2,6-dimethyl-phenoxy]-propyl}-acetamide The title compound is prepared in analogy to N—((S)-3-[2-ethyl-4-(N-hydroxycarbamimidoyl)-6-methyl-phenoxy]-2-hydroxy-propyl)-2-hydroxy-acetamide. LC-MS: $t_R$=0.23 min, [M+1]$^+$=312.25.

(S)—N—(3-[2-chloro-4-(N-hydroxycarbamimidoyl)-6-methyl-phenoxy]-2-hydroxy-propyl)-2-hydroxy-acetamide The title compound is obtained as a beige wax (1.1 g) in analogy to N—((S)-3-[2-ethyl-4-(N-hydroxycarbamimidoyl)-6-methyl-phenoxy]-2-hydroxy-propyl)-2-hydroxy-acetamide starting from 3-chloro-4-hydroxy-5-methyl-benzonitrile. LC-MS: $t_R$=0.48 min, [M+H]$^+$=331.94.

(S)-2-hydroxy-N-(2-hydroxy-3-[4-(N-hydroxycarbamimidoyl)-2-methoxy-6-methyl-phenoxy]-propyl)-acetamide The title compound is obtained as a reddish oil (1.3 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-3-methoxy-5-methyl-benzonitrile. LC-MS: $t_R$=0.49 min, [M+H]$^+$=327.98.

(S)-2-hydroxy-N-(2-hydroxy-3-[4-(N-hydroxycarbamimidoyl)-3-methyl-phenoxy]-propyl)-acetamide The title compound is obtained as a beige oil (1.0 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-2-methyl-benzonitrile. LC-MS: $t_R$=0.35 min, [M+H]$^+$=297.99.

3-ethyl-4-[(S)-2-hydroxy-3-(2-hydroxy-acetylamino)-propoxy]-5-methyl-benzoic acid a) To an ice-cold solution of H$_2$SO$_4$ (150 mL) in water (250 mL), 2-ethyl-6-methylaniline (15.0 g, 111 mmol) is added. The solution is treated with ice (150 g) before a solution of NaNO$_2$ (10.7 g, 155 mmol) in water (150 mL) and ice (50 g) is added dropwise. The mixture is stirred at 0° C. for 1 h. 50% aq. H$_2$SO$_4$ (200 mL) is added and stirring is continued at rt for 18 h. The mixture is extracted with DCM, the org. extracts are dried over MgSO$_4$ and evaporated. The crude product is purified by CC on silica gel eluting with Hept:EA 9:1 to give 2-ethyl-6-methyl-phenol as a crimson oil (8.6 g). LC-MS: $t_R$=0.89 min; $^1$H NMR (CDCl$_3$): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condenser and the mixture is refluxed for 3 h. The mixture is cooled to rt, diluted with water (100 mL) and extracted with EA. The org. extract is washed with sat. aq. NaHCO$_3$, dried over MgSO$_4$ and evaporated. The remaining solid is dissolved in EA and treated with Hept to initialize crystallisation. The solid material is collected and dried to give 3-ethyl-4-hydroxy-5-methyl-benzaldehyde as a colourless crystalline powder (3.13 g). $^1$H NMR (CDCl$_3$): δ 9.83 (s, 1H), 7.58-7.53 (m, 2H), 5.30 (br s, 1H), 2.69 (q, J=7.6 Hz, 2H), 2.32 (s, 3H), 1.28 (t, J=7.6 Hz, 3H).

c) To a solution of 3-ethyl-4-hydroxy-5-methyl-benzaldehyde (25.0 g, 152 mmol) in acetonitrile (250 mL), $K_2CO_3$ (42.1 g, 305 mmol) followed by benzyl bromide (26.0 g, 152 mmol) is added. The suspension is stirred at 60° C. for 18 h. The mixture is diluted with water (150 mL) and EA (150 mL). The org. extract is separated and the aq. phase is extracted once more with EA (100 mL). The combined org. extracts are washed with water (150 mL) and concentrated. The crude product is purified by CC on silica gel eluting with Hept:EA 9:1 to give 4-benzyloxy-3-ethyl-5-methyl-benzaldehyde as a yellow oil (27.2 g). LC-MS: $t_R$=1.09 min; $^1$H NMR ($D_6$-DMSO): δ 1.19 (t, J=7.5 Hz, 3H), 2.35 (s, 3H), 2.70 (q, J=7.5 Hz, 2H), 4.90 (s, 2H), 7.37-7.41 (m, 1H), 7.42-7.46 (m, 2H), 7.49-7.52 (m, 2H), 7.65-7.69 (m, 2H), 9.92 (s, 1H).

d) To a solution of 4-benzyloxy-3-ethyl-5-methyl-benzaldehyde (25.0 g, 98.3 mmol) in acetone (500 mL), $KMnO_4$ (20.2 g, 127.8 mmol) is added. The mixture becomes warm (45° C.). The mixture is stirred at rt for 16 h before it is filtered over glass filters. The clear, colourless filtrate is concentrated, diluted with water and acidified with 2N aq. HCl, then extracted twice with EA. The combined org. extracts are dried over $MgSO_4$, filtered, concentrated and dried to give 4-benzyloxy-3-ethyl-5-methyl-benzoic acid as a pale yellow solid (19.2 g). LC-MS: $t_R$=1.00 min; $^1$H NMR ($D_6$-DMSO): δ 1.13-1.22 (m, 3H), 2.32 (s, 3H), 2.64-2.72 (m, 2H), 4.87 (s, 2H), 7.34-7.56 (m, 5H), 7.69 (m, 2H), 12.66 (br s, 1H).

e) To a suspension of 4-benzyloxy-3-ethyl-5-methyl-benzoic acid (10.0 g, 37.0 mmol) in toluene (150 mL), N,N-dimethylformamide di-tert-butyl acetal (22.6 g, 111 mmol) is added. The mixture is refluxed for 24 h before another portion of N,N-dimethylformamide di-tert-butyl acetal (22.6 g, 111 mmol) is added. Refluxing is continued for another 24 h, then another portion of N,N-dimethylformamide di-tert-butyl acetal (22.6 g, 111 mmol) is added. The mixture is again refluxed for 24 h before it is cooled to rt, diluted with EA and washed with sat. aq. $Na_2CO_3$ solution. The org. extract is dried over $MgSO_4$, filtered and concentrated. The crude product is purified by CC on silica gel eluting with Hept:EA 9:1 to give 4-benzyloxy-3-ethyl-5-methyl-benzoic acid tert-butyl ester as a pale yellow oil (9.02 g). LC-MS: $t_R$=1.17 min.

f) To a solution of 4-benzyloxy-3-ethyl-5-methyl-benzoic acid tert-butyl ester (9.02 g, 27.6 mmol) in THF (50 mL) and ethanol (50 mL), Pd/C (400 mg, 10% Pd) is added. The slurry is stirred at rt for 24 h under 1 bar of $H_2$. The catalyst is removed by filtration and the filtrate is concentrated, dissolved again in THF (50 mL) and ethanol (50 mL), and again treated with Pd/C (400 mg, 10% Pd). The slurry is stirred at rt for 24 h under 1 bar of $H_2$. The catalyst is again removed by filtration and the filtrate is concentrated and dried to give 3-ethyl-4-hydroxy-5-methyl-benzoic acid tert-butyl ester as a pale yellow oil (7.13 g). LC-MS: $t_R$=1.01 min; $^1$H NMR ($CDCl_3$): δ 1.28 (t, J=7.8 Hz, 3H), 1.61 (s, 9H), 2.30 (s, 3H), 2.67 (q, J=7.5 Hz, 2H), 5.13 (br s, 1H), 7.67 (s, 1H), 7.69 (s, 1H).

g) 3-ethyl-4-[(S)-2-hydroxy-3-(2-hydroxy-acetylamino)-propoxy]-5-methyl-benzoic acid tert-butyl ester (5.94 g) is prepared starting from the above 3-ethyl-4-hydroxy-5-methyl-benzoic acid tert-butyl ester (6.53 g, 27.6 mmol) following the procedures given for N—((S)-3-[2-ethyl-4-(N-hydroxycarbamimidoyl)-6-methyl-phenyl]-2-hydroxy-propyl)-2-hydroxy-acetamide. LC-MS: $t_R$=0.87 min; [M+H]$^+$=368.11; $^1$H NMR ($CDCl_3$): δ1.17 (t, J=7.5 Hz, 3H), 1.53 (s, 9H), 2.28 (s, 3H), 2.66 (q, J=7.5 Hz, 2H), 3.17-3.26 (m, 1H), 3.38-3.46 (m, 1H), 3.65-3.75 (m, 2H), 3.83 (d, J=5.5 Hz, 2H), 3.91-3.97 (m, 1H), 5.28 (d, J=5.3 Hz, 1H), 5.54 (t, J=5.5 Hz, 1H), 7.59 (s, 1H), 7.60 (s, 1H), 7.68 (t, J=5.5 Hz, 1H).

h) To a cooled (0° C.) solution of 3-ethyl-4-[(S)-2-hydroxy-3-(2-hydroxy-acetylamino)-propoxy]-5-methyl-benzoic acid tert-butyl ester (5.94 g, 16.2 mmol) in DCM (100 mL), TFA (5 mL) is added. The mixture is warmed to rt and stirred for 2 h. The mixture is concentrated, dissolved in acetonitrile/water (6 mL) and separated by prep. HPLC to give the title compound as a white powder (2.20 g). LC-MS: $t_R$=0.41 min; [M+H]$^+$=312.18.

4-benzyloxy-3-ethyl-5-methyl-benzoic acid a) To an ice-cold solution of $H_2SO_4$ (150 mL) in water (250 mL) 2-ethyl-6-methylaniline (15.0 g, 111 mmol) is added. The solution is treated with ice (150 g) before a solution of $NaNO_2$ (10.7 g, 155 mmol) in water (150 mL) and ice (50 g) is added dropwise. The mixture is stirred at 0° C. for 1 h. 50% aq. $H_2SO_4$ (200 mL) is added and stirring is continued at rt for 18 h. The mixture is extracted with DCM, the org. extracts are dried over $MgSO_4$ and evaporated. The crude product is purified by CC on silica gel eluting with Hept:EA 9:1 to give 2-ethyl-6-methyl-phenol as a crimson oil (8.6 g). LC-MS: $t_R$=0.89 min; $^1$H NMR ($CDCl_3$): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condenser and the mixture is refluxed for 3 h. The mixture is cooled to rt, diluted with water (100 mL) and extracted with EA. The org. extract is washed with sat. aq. $NaHCO_3$, dried over $MgSO_4$ and evaporated. The remaining solid is dissolved in EA and treated with heptane to initialize crystallisation. The solid material is collected and dried to give 3-ethyl-4-hydroxy-5-methyl-benzaldehyde as a colourless crystalline powder (3.13 g). $^1$H NMR ($CDCl_3$): δ 9.83 (s, 1H), 7.58-7.53 (m, 2H), 5.30 (br s, 1H), 2.69 (q, J=7.6 Hz, 2H), 2.32 (s, 3H), 1.28 (t, J=7.6 Hz, 3H).

c) To a solution of 3-ethyl-4-hydroxy-5-methyl-benzaldehyde (34.9 g, 0.213 mol) in MeCN (350 mL), $K_2CO_3$ (58.7 g, 0.425 mol) and benzylbromide (36.4 g, 0.213 mol) is added. The mixture is stirred at 60° C. for 2 h before it is cooled to rt, diluted with water and extracted twice with EA. The org. extracts are washed with water and concentrated to give crude 4-benzyloxy-3-ethyl-5-methyl-benzaldehyde as an orange oil (45 g). $^1$H NMR ($CDCl_3$): δ1.29 (t, J=7.5 Hz, 3H), 2.40 (s, 3H), 2.77 (q, J=7.8 Hz, 2H), 4.90 (s, 2H), 7.31-7.52 (m, 5H), 7.62 (d, J=1.5 Hz, 1H), 7.66 (d, J=1.8 Hz, 1H), 9.94 (s, 1H).

d) To a mixture of 4-benzyloxy-3-ethyl-5-methyl-benzaldehyde (132 g, 0.519 mol) and 2-methyl-2-butene (364 g, 5.19 mol) in tert-butanol (1500 mL), a solution of $NaH_2PO_4$ dihydrate (249 g, 2.08 mol) in water (1500 mL) is added. To this mixture, $NaClO_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The org. layer is separated and washed with 20% aq. NaHS solution (1500 mL) and water (500 mL). The org. phase is then extracted 3 times with 0.5 N aq. NaOH (1000 mL), the aq. phase is acidified with 25% aq. HCl (500 mL) and extracted twice with TBME (1000 mL). These org. extracts are combined and evaporated to dryness to give 4-benzyloxy-3-ethyl-5-methylbenzoic acid. $^1$H NMR (D$_6$-DMSO): δ 1.17 (t, J=7.5 Hz, 3H), 2.31 (s, 3H), 2.67 (q, J=7.5 Hz, 2H), 4.86 (s, 2H), 7.34-7.53 (m, 5H), 7.68 (s, 2H), 12.70 (s, 1H).

4-benzyloxy-3-ethyl-5-methyl-benzoic acid hydrazide

To a solution of 4-benzyloxy-3-ethyl-3-methyl-benzoic acid (8.3 g, 30.7 mmol) in DCM (300 mL) is added DIPEA (10.7 mL) and the mixture is cooled to 0° C. before PyBOP (14.5 g, 33.8 mmol) is added. After 10 min, a solution of 1M hydrazine in THF (100 mL) is added dropwise and the mixture is slowly warmed to rt during 2 h. The reaction mixture is then washed with sat. aq. NaHCO$_3$ followed by brine. The org. phase is collected, dried over MgSO$_4$, filtered and evaporated to give the title compound as a yellow wax (24 g, 40% purity). LC-MS: $t_R$=0.82 min; [M+H]$^+$=285.10.

3-formyl-5-methyl-benzoic acid a) A solution of 2,5-dimethyl benzoic acid (6.00 g, 40 mmol), 2,2'-azo-bis(2-methylpropionitrile) (670 mg, 164 mmol) and N-bromo-succinimide (7.48 g, 42 mmol) in DCM (250 mL) was refluxed for 18 h. The mixture was extracted with 1N aq. NaOH and water. The combined aqueous extracts were acidified by adding 1N aq. HCl and extracted twice with EA. The combined org. extracts were washed with water, dried over Na$_2$SO$_4$, filtered and concentrated. The crude product was crystallised from hot EtOH (25 mL) by adding cold water (50 mL). The mixture was cooled to rt, the crystallised material was collected and dried to give 3-bromomethyl-5-methyl-benzoic acid as a white solid (4.20 g). LC-MS: $t_R$=0.64 min; [M+1]$^+$=229.05.

b) To a solution of 3-bromomethyl-5-methyl-benzoic acid (3.90 g, 17 mmol) in water (30 mL) and MeCN (30 mL), Cu(NO$_3$)$_2$ hemipentahydrate (12.77 g, 68 mmol) followed by water (50 mL) was added. The turquoise mixture was refluxed for 2 h before it was concentrated to about half of the original volume. The dark green solution was extracted three times with EA (150 mL). The org. extracts were washed twice with water (2×50 mL), combined, dried over Na$_2$SO$_4$, filtered and concentrated. The white residue was separated by prep. HPLC (XBridge Prep C18, 30×75 mm, 5 μm, 95% MeCN in water containing 0.5% of formic acid) to give 3-hydroxymethyl-5-methyl-benzoic acid as a white solid (897 mg; LC-MS*: $t_R$=0.17 min; [M-1]$^-$=164.86), along with the title compound as a white solid (160 mg). To a solution of the above 3-hydroxymethyl-5-methyl-benzoic acid (947 mg, 5.70 mmol) in MeCN (40 mL), MnO$_2$ (1.49 g, 17.1 mmol) was added and the resulting mixture was stirred at 80° C. for 16 h before another portion of MnO$_2$ (1.21 g, 13.9 mmol) and acetonitrile (40 mL) was added and stirring was continued at 80° C. for 4 h. The mixture was filtered over a glass fibre filter, the colourless filtrate was concentrated and purified by prep. HPLC (as above) to give the title compound (504 mg) as a white solid. LC-MS*: $t_R$=0.26 min; [M-1]$^-$=162.88; $^1$H NMR (D$_6$-DMSO): δ 2.47 (s, 3H), 7.96 (s, 1H), 8.07 (s, 1H), 8.26 (s, 1H), 10.06 (s, 1H), 13.28 (m, 1H).

3-formyl-5-ethyl-benzoic acid a) A solution of 3-formyl-benzoic acid (10.8 g) in H$_2$SO$_4$ (100 mL) is warmed to 60° C. before N-bromo-succinimide (13.4 g, 75.5 mmol) was added in 3 portions every 15 min. After complete addition, stirring was continued for 2 h at 60° C. The mixture is poured onto 1000 g of ice. The precipitate that formed was collected, washed with water and dried under high vacuum to give 3-formyl-5-bromo-benzoic acid as a white powder (15.1 g). LC-MS*: $t_R$=0.39 min, [M+H]$^+$=227.03.

b) Under nitrogen, Pd(dppf) (97 mg, 0.119 mmol) was added to a stirred solution of 3-formyl-5-bromo-benzoic acid (3.00 g, 11.92 mmol) in dioxane (100 mL). Diethyl zinc (14.7 g, 17.9 mmol, as a 15% solution in toluene) was added and the mixture was stirred at 75° C. for 1 h. The reaction was quenched by adding water (5 mL) and the solvent was evaporated to a volume of about 50 mL. The mixture was basified by adding sat. aq. ammonia (1 mL). The mixture was filtered and the filtrate was acidified by adding formic acid (4 mL) before it was separated by prep. HPLC to give the title compound as a colourless resin (1.17 g). LC-MS*: $t_R$=0.44 min, [M-H]$^-$=177.26; $^1$H NMR (D$_6$-DMSO): δ 1.24 (t, J=7.8 Hz, 3H), 2.77 (q, J=7.5 Hz, 2H), 7.92 (t, J=1.8 Hz), 8.08 (t, J=1.8 Hz, 1H), 8.26 (t, J=1.5 Hz, 1H), 10.06 (s, 1H).

3-formyl-5-propyl-benzoic acid

The title compound is prepared in analogy to 3-formyl-5-ethyl-benzoic (582 mg) from 3-formyl-5-bromo-benzoic acid (1.00 g, 4.37 mmol) using propyl zinc bromide. LC-MS*: $t_R$=0.56 min, [M-H]$^-$=191.32; $^1$H NMR (D$_6$-DMSO): δ 0.91 (t, J=7.3 Hz, 3H), 1.65 (h, J=7.3 Hz, 2H), 2.73 (t, J=7.3 Hz, 2H), 7.97 (s, 1H), 8.07 (s, 1H), 8.28 (s, 1H), 10.07 (s, 1H).

3-formyl-5-isopropyl-benzoic acid

The title compound is prepared in analogy to 3-formyl-5-ethyl-benzoic acid. LC-MS*: $t_R$=0.55 min, [M-H]$^-$=191.27.

3-formyl-4-methyl-benzoic acid a) To a solution of methyl 3-formyl-4-hydroxybenzoate (4.20 g, 23.3 mmol) in DCM (150 mL), pyridine (5.53 g, 69.9 mmol) was added. The mixture was cooled to 0° C. before trifluoromethane sulfonic acid anhydride (7.89 g, 28.0 mmol) was added. The mixture was stirred at 0° C. for 1 h before it was concentrated. The residue was dissolved in water (2 mL) and formic acid (2 mL) and was then separated by prep. HPLC to give 3-formyl-4-trifluoromethanesulfonyloxy-benzoic acid methyl ester as a pale yellow oil (5.70 g). LC-MS**: $t_R$=1.00 min. $^1$H NMR (D$_6$-DMSO): δ 3.94 (s, 3H), 7.79 (d, J=8.8 Hz, 1H), 8.40 (dd, J=8.5, 2.3 Hz, 1H), 8.65 (d, J=2.3 Hz, 1H), 10.16 (s, 1H).

b) Under nitrogen, Pd(dppf) (72 mg, 89 μmol) was added to a solution of 3-formyl-4-trifluoromethanesulfonyloxy-benzoic acid methyl ester (2.80 g, 8.97 mmol) in dioxane (40 mL). The mixture was stirred at rt and dimethyl zinc (11.2 g, 13.5 mmol, 12.1 mL of a 1.2M solution in toluene) was added. The mixture was stirred at 75° C. for 1 h. The mixture was cooled to rt before a 2M aq. LiOH solution (40 mL) was added. The mixture was stirred at rt for 2 h before it was concentrated. The residue was dissolved in EA and extracted with 1M aq. NaOH and water. The aq. extracts were acidified by adding 2N aq. HCl (30 mL) and then extracted with EA. The org. extract was dried over Na$_2$SO$_4$, filtered and concentrated. The crude product was purified by prep. HPLC to give the title compound as a pale yellow powder (903 mg). LC-MS*: $t_R$=0.27 min, [M-H]$^-$=162.90; $^1$H NMR (D$_6$-DMSO): δ 2.69 (s, 3H), 7.49 (d, J=7.8 Hz, 1H), 8.08 (dd, J=7.8, 1.8 Hz, 1H), 8.38 (d, J=1.8 Hz, 1H), 10.29 (s, 1H), 13.20 (s, 1H).

3-formyl-4-ethyl-benzoic acid

The title compound is prepared in analogy to 3-formyl-4-methyl-benzoic acid using diethyl zinc in step b). LC-MS*:

$t_R$=0.45 min, [M−H]⁻=177.30; ¹H NMR (D₆-DMSO): δ 1.21 (t, J=7.5 Hz, 3H), 3.10 (q, J=7.5 Hz, 2H), 7.53 (d, J=8.0 Hz, 1H), 8.11 (dd, J=7.8, 1.5 Hz, 1H), 8.39 (d, J=1.3 Hz, 1H), 10.30 (s, 1H), 13.10 (br s, 1H).

4-formyl-3-methyl benzoic acid a) To a hot (80° C.) solution of 4-bromo-3-methyl benzoic acid (3.00 g, 13.95 mmol) in toluene (250 mL), N,N-dimethylformamide di-tert-butyl acetal (11.35 g, 50.2 mmol) was added. The mixture was stirred at 80° C. for 8 h and at rt for 16 h before another portion of N,N-dimethylformamide di-tert-butyl acetal (5.67 g, 25.1 mmol) was added. Stirring was continued at 80° C. for 16 h. The mixture was cooled to rt, diluted with EA and washed with sat. aq. NaHCO₃-solution followed by water. The org. layer was separated, dried over Na₂SO₄, filtered, evaporated and dried under high vacuum at 40° C. to give tert-butyl 4-bromo-3-methyl benzoate as a pale yellow oil (2.31 g). LC-MS: $t_R$=1.10 min; [M+1]⁺=not detectable; ¹H NMR (CDCl₃): δ1.61 (s, 9H), 2.46 (s, 3H), 7.59 (d, J=8.3 Hz, 1H), 7.66 (d, J=8.3 Hz, 1H), 7.86 (s, 1H).

b) A stirred solution of tert-butyl 4-bromo-3-methyl benzoate (1.78 g, 6.57 mmol) in THF (50 mL) was cooled to −78° C. before n-butyl lithium (7.22 mL of a 1.6 M solution in hexane) was added dropwise. Upon complete addition, DMF (960 mg, 13.13 mmol) was added. Stirring was continued at −78° C. for 30 min before the mixture was warmed to rt. After stirring for 1 h at rt, the reaction was quenched by the addition of 1 N aq. HCl (20 mL). The org. solvent was evaporated and the remaining solution was extracted with EA (100 mL). The org. extract was washed with sat. aq. NaHCO₃-solution and water and the washings were extracted back with water. The combined org. extracts were dried over Na₂SO₄, filtered, concentrated and dried to give tert-butyl 4-formyl-3-methyl benzoate as a pale yellow oil (1.42 g). LC-MS: $t_R$=1.11 min.

c) A solution of tert-butyl 4-formyl-3-methyl benzoate (820 mg, 3.72 mmol) in DCM (10 mL) and TFA (10 mL) was stirred at rt for 1 h before the solvent was evaporated. The residue was dissolved in sat. aq. Na₂CO₃ solution (50 mL) and washed with EA (2×100 mL). The org. washings were extracted with sat. aq. Na₂CO₃-solution (50 mL). The aq. extracts were acidified by adding conc. aq. HCl and then extracted twice with EA. The org. extracts were washed with water, dried over Na₂SO₄, filtered, concentrated and dried to give 4-formyl-3-methyl benzoic acid as a beige solid (350 mg). LC-MS: $t_R$=0.72 min, [M+1]⁺=not detectable; ¹H NMR (D₆-DMSO): δ 2.68 (s, 3H), 7.90 (s, 1H), 7.93 (s, 2H), 10.33 (s, 1H), 13.30 (br s, 1H).

3-ethyl-4-formyl-benzoic acid

The title compound was prepared in analogy to 4-ethyl-3-formyl benzoic acid starting from 4-formyl-3-hydroxy-benzoic acid and using diethyl zinc in step b). LC-MS*: $t_R$=0.38 min, [M−H]⁻=177.28; ¹H NMR (D₆-DMSO): δ 1.21 (t, J=7.5 Hz, 3H), 3.10 (q, J=7.3 Hz, 2H), 7.93 (s, 1H), 7.94 (s, 2H), 10.34 (s, 1H), 13.36 (br s, 1H).

3-[(ethyl-methyl-amino)-methyl]-5-methyl-benzoic acid (Method B)

To a solution of 3-formyl-5-methyl-benzoic acid (2.83 g, 17.2 mmol) in DCM (100 mL) and NMP (15 mL), AcOH (3.17 g, 51.7 mmol) and N-ethyl-methylamine (4.08 g, 69.0 mmol) is added. The mixture is stirred at rt for 45 min before NaBH(OAc)₃ (8.12 g, 34.5 mmol) is added. The mixture is stirred at rt for 16 h before it is concentrated. The remaining residue is dissolved in MeCN and DMF and filtered over a paper filter. The filtrate is separated by prep. HPLC (Waters XBridge 50×50 mm+100×50 mm, eluting with a gradient of acetonitrile in water containing 0.5% of sat. aq. ammonia) to give the title compound as a white solid (1.67 g). LC-MS*: $t_R$=0.46 min, [M−H]⁻=206.28; ¹H NMR (D₆-DMSO): δ 1.03 (t, J=7.3 Hz, 3H), 2.09 (s, 3H), 2.35 (s, 3H), 2.39 (q, J=7.0 Hz, 2H), 3.46 (s, 2H), 7.31 (s, 1H), 7.63 (s, 1H), 7.67 (s, 1H).

4-dimethylaminomethyl-3-methoxy-benzoic acid a) To a solution of dimethyl amine (0.9 mL of a 5.6 M solution in ethanol) in THF (20 mL), a solution of methyl 4-(bromomethyl)-3-methoxybenzoate (500 mg, 2.06 mmol) was added. The mixture was stirred at rt for 35 min before it was diluted with water (150 mL) and sat. aq. Na₂CO₃-solution (50 mL) and extracted with EA (70 mL). The org. extract was separated, dried over Na₂SO₄, filtered, evaporated and dried to give methyl 4-dimethylaminomethyl-3-methoxy-benzoate as a colourless oil (420 mg). LC-MS: $t_R$=0.61 min, [M+1]⁺=224.04.

b) To a solution of methyl 4-dimethylaminomethyl-3-methoxy-benzoate (420 mg, 1.88 mmol) in MeOH (4 mL), 1 M aq. NaOH solution (2.5 mL) was added. The mixture was stirred at 50° C. for 2 h and at rt for 16 h before it was neutralised by adding 1 M aq. HCl (1.25 mL) and the solvent was evaporated. The residue was suspended in n-butanol (100 mL) and the mixture was refluxed for 1 h. The suspension was cooled to rt, filtered and the filtrate was concentrated and dried to give 4-dimethylaminomethyl-3-methoxy-benzoic acid as a colourless resin (380 mg). LC-MS*: $t_R$=0.44 min, [M+1]⁺=210.32.

3-[(ethyl-methyl-amino)-methyl]-5-methyl-benzoic acid hydrazide

To a solution of 3-[(ethyl-methyl-amino)-methyl]-5-methyl-benzoic acid (215 mg, 1.04 mmol) in THF (5 mL), PyBOP (541 mg, 1.04 mmol) followed by DIPEA (269 mg, 2.08 mmol) is added. The mixture is stirred until all solid material has dissolved and is then transferred into a 1M solution of hydrazine in THF (8.3 mL; 266 mg, 8.33 mmol). The resulting suspension is stirred at rt for 1 h before it is diluted with EA and washed with water. The org. extract is concentrated and dried to give the crude title compound as a white solid (640 mg). LC-MS: $t_R$=0.35 min, [M+1]⁺=222.05.

3-[3-(3-ethyl-4-hydroxy-5-methyl-phenyl)-[1,2,4]oxadiazol-5-yl]-5-methyl-benzaldehyde A solution of 3-formyl-5-methyl-benzoic acid (3.80 g, 23.2 mmol), HOBt (4.17 g, 27.8 mmol) and EDC HCl (4.44 g, 23.2 mmol) in DMF (200 mL) was stirred at rt for 5 min before 3-ethyl-4,N-dihydroxy-5-methyl-benzamidine (4.50 g, 23.2 mmol) was added. The mixture was stirred at rt for 1 h. The mixture was heated to 75° C. and stirring was continued for 3 h. The mixture was concentrated to about 40 mL, acidified by adding formic acid (0.6 mL), diluted with a small amount of acetonitrile/water and separated by prep. HPLC (Waters XBridge Prep C18, 50×50 mm+50×100 mm, 10 μm, 80% to 10% water (containing 0.5% of formic acid) in MeCN) to give the title compound as a white solid (2.14 g). LC-MS**: $t_R$=0.82 min; [M+1]⁺=323.15, ¹H NMR (D₆-DMSO): δ 1.20 (t, J=7.3 Hz, 3H), 2.28 (s, 3H), 2.55 (s, 3H), 2.69 (q, J=7.5 Hz, 2H), 7.71 (d, J=2.0 Hz, 2H), 8.05 (s, 1H), 8.32 (s, 1H), 8.49 (s, 1H), 8.95 (s, 1H), 10.14 (s, 1H).

rac-N-(3-{4-[5-(3-formyl-phenyl)-[1,2,4]oxadiazol-3-yl]-2,6-dimethyl-phenoxy}-2-hydroxy-propyl)-2-hydroxy-acetamide A solution of 3-formyl-benzoic acid (170 mg, 1.13 mmol), HOBt (184 mg, 1.36 mmol) and rac-2-hydroxy-N-{2-hydroxy-3-[4-(N-hydroxycarbamimidoyl)-2,6-dimethyl-phenoxy]-propyl}-acetamide (352 mg, 1.13 mmol) in THF (4 mL) and DMF (6 mL) was cooled to 0° C. before EDC hydrochloride (239 mg, 1.24 mmol) was added in portions. The mixture was stirred at rt for 1 h before it was diluted with THF (4 mL) and heated to 80° C. for 16 h. The mixture was concentrated and then separated by prep. HPLC (Waters XBridge Prep C18, 75×30 mm ID, 5 μm, 90% to 10% water (containing 0.5% of formic acid) in MeCN) to give the title compound as a white solid (130 mg). LC-MS*: $t_R$=0.75 min; [M+1]$^+$=425.90, $^1$H NMR (D$_6$-DMSO): δ 2.35 (s, 6H), 3.20-3.29 (m, 1H), 3.40-3.49 (m, 1H), 3.71-3.82 (m, 2H), 3.84 (d, J=5.0 Hz, 2H), 3.92-4.00 (m, 1H), 5.30 (d, J=4.8 Hz, 1H), 5.55 (t, J=5.5 Hz, 1H), 7.70 (br t, J=4.8 Hz, 1H), 7.81 (s, 2H), 7.91 (t, J=7.8 Hz, 1H), 8.24 (d, J=7.5 Hz, 1H), 8.49 (d, J=7.8 Hz, 1H), 8.69 (s, 1H), 10.18 (s, 1H).

N—((S)-3-{2-ethyl-4-[5-(3-formyl-4-methyl-phenyl)-[1,2,4]oxadiazol-3-yl]-6-methyl-phenoxy}-2-hydroxy-propyl)-2-hydroxy-acetamide The title compound (405 mg) is prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 3-formyl-4-methyl-benzoic acid (338 mg, 2.06 mmol) and N—((S)-3-[2-ethyl-4-(N-hydroxycarbamimidoyl)-6-methyl-phenoxy]-2-hydroxy-propyl)-2-hydroxy-acetamide (670 mg, 2.06 mmol). LC-MS**: $t_R$=0.68 min; [M+1]$^+$=454.17; $^1$H NMR (D$_6$-DMSO): δ 1.23 (t, J=7.5 Hz, 3H), 2.35 (s, 3H), 2.70-2.78 (m, 5H), 3.21-3.29 (m, 1H), 3.39-3.48 (m, 1H), 3.71-3.80 (m, 2H), 3.84 (d, J=5.5 Hz, 2H), 3.93-4.01 (m, 1H), 5.32 (d, J=5.3 Hz, 1H), 5.56 (t, J=5.5 Hz, 1H), 7.66 (d, J=8.3 Hz, 1H), 7.71 (t, J=5.5 Hz, 1H), 7.81 (s, 2H), 8.33 (dd, J=8.0, 1.8 Hz, 1H), 8.60 (d, J=1.8 Hz, 1H), 10.37 (s, 1H).

N—((S)-3-{2-ethyl-4-[5-(3-formyl-4-ethyl-phenyl)-[1,2,4]oxadiazol-3-yl]-6-methyl-phenoxy}-2-hydroxy-propyl)-2-hydroxy-acetamide The title compound (233 mg) is prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 3-formyl-4-ethyl-benzoic acid (360 mg, 2.02 mmol) and N—((S)-3-[2-ethyl-4-(N-hydroxycarbamimidoyl)-6-methyl-phenoxy]-2-hydroxy-propyl)-2-hydroxy-acetamide (657 mg, 2.02 mmol). LC-MS**: $t_R$=0.72 min; [M+1]$^+$=468.21; $^1$H NMR (D$_6$-DMSO): δ 1.23 (t, J=7.5 Hz, 3H), 1.26 (t, J=7.5 Hz, 3H), 2.35 (s, 3H), 2.74 (q, J=7.5 Hz, 2H), 3.17 (q, J=7.3 Hz, 2H), 3.21-3.29 (m, 1H), 3.40-3.48 (m, 1H), 3.70-3.80 (m, 2H), 3.84 (d, J=5.8 Hz, 2H), 3.93-4.01 (m, 1H), 5.32 (d, J=5.0 Hz, 1H), 5.56 (t, J=5.8 Hz, 1H), 7.68-7.73 (m, 2H), 7.81 (s, 2H), 8.37 (dd, J=8.0, 1.8 Hz, 1H), 8.61 (d, J=1.8 Hz, 1H), 10.38 (s, 1H).

N—((S)-3-{2-ethyl-4-[5-(4-formyl-3-ethyl-phenyl)-[1,2,4]oxadiazol-3-yl]-6-methyl-phenoxy}-2-hydroxy-propyl)-2-hydroxy-acetamide The title compound (183 mg) is prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide starting from 3-ethyl-4-formyl-benzoic acid (140 mg, 0.786 mmol) and N—((S)-3-[2-ethyl-4-(N-hydroxycarbamimidoyl)-6-methyl-phenoxy]-2-hydroxy-propyl)-2-hydroxy-acetamide (256 mg, 0.786 mmol). LC-MS**: $t_R$=0.72 min; [M+1]$^+$=468.25; $^1$H NMR (D$_6$-DMSO): δ 1.23 (t, J=7.8 Hz, 3H), 1.28 (t, J=7.3 Hz, 3H), 2.36 (s, 3H), 2.70-2.78 (m, 3H), 3.19 (q, J=7.3 Hz, 2H), 3.23-3.29 (m, 1H), 3.40-3.48 (m, 1H), 3.71-3.81 (m, 2H), 3.84 (d, J=5.5 Hz, 2H), 3.94-4.00 (m, 1H), 5.31 (d, J=5.3 Hz, 1H), 5.56 (t, J=5.5 Hz, 1H), 7.71 (t, J=5.8 Hz, 1H), 7.82 (s, 2H), 8.09 (d, J=8.0 Hz, 1H), 8.19-8.24 (m, 2H), 10.38 (s, 1H).

N—((S)-3-{2-ethyl-4-[5-(3-formyl-5-methyl-phenyl)-[1,2,4]oxadiazol-3-yl]-6-methyl-phenoxy}-2-hydroxy-propyl)-2-hydroxy-acetamide The title compound (407 mg) was prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide starting from 3-formyl-5-methyl-benzoic acid (340 mg, 2.07 mmol) and N—((S)-3-[2-ethyl-4-(N-hydroxycarbamimidoyl)-6-methyl-phenoxy]-2-hydroxy-propyl)-2-hydroxy-acetamide (674 mg, 2.07 mmol). LC-MS: $t_R$=0.85 min; [M+1]$^+$=454.11; $^1$H NMR (D$_6$-DMSO): δ 1.23 (t, J=7.5 Hz, 3H), 2.36 (s, 3H), 2.55 (s, 3H), 2.74 (q, J=7.5 Hz, 2H), 3.20-3.29 (m, 1H), 3.39-3.48 (m, 1H), 3.70-3.81 (m, 2H), 3.84 (d, J=4.8 Hz, 2H), 3.93-4.00 (m, 1H), 5.32 (d, J=4.8 Hz, 1H), 5.56 (t, J=5.0 Hz, 1H), 7.71 (t, J=5.8 Hz, 1H), 7.82 (s, 2H), 8.06 (s, 1H), 8.34 (s, 1H), 8.50 (s, 1H), 10.15 (s, 1H).

N—((S)-3-{2-ethyl-4-[5-(3-formyl-5-ethyl-phenyl)-[1,2,4]oxadiazol-3-yl]-6-methyl-phenoxy}-2-hydroxy-propyl)-2-hydroxy-acetamide The title compound (538 mg) was prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 3-formyl-5-ethyl-benzoic acid (600 mg, 3.37 mmol) and N—((S)-3-[2-ethyl-4-(N-hydroxycarbamimidoyl)-6-methyl-phenoxy]-2-hydroxy-propyl)-2-hydroxy-acetamide (1096 mg, 3.37 mmol). LC-MS**: $t_R$=0.74 min; [M+1]$^+$=468.26; $^1$H NMR (D$_6$-DMSO): δ 1.24 (t, J=7.5 Hz, 3H), 1.30 (t, J=7.5 Hz, 3H), 2.36 (s, 3H), 2.71-2.78 (m, 5H), 2.88 (q, J=7.8 Hz, 2H), 2.90 (s, 3H), 3.21-3.28 (m, 1H), 3.41-3.48 (m, 1H), 3.72-3.82 (m, 2H), 3.84 (s, 2H), 3.94-4.01 (m, 1H), 5.31 (br s, 1H), 5.55 (br s, 1H), 7.70 (t, J=6.0 Hz, 1H), 7.83 (s, 2H), 7.96 (s, 1H), 8.10 (s, 1H), 8.35 (s, 1H), 8.52 (s, 1H), 10.16 (s, 1H).

N—((S)-3-{2-ethyl-4-[5-(3-formyl-5-propyl-phenyl)-[1,2,4]oxadiazol-3-yl]-6-methyl-phenoxy}-2-hydroxy-propyl)-2-hydroxy-acetamide The title compound (552 mg) was prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 3-formyl-5-propyl-benzoic acid (582 mg, 3.03 mmol) and N—((S)-3-[2-ethyl-4-(N-hydroxycarbamimidoyl)-6-methyl-phenoxy]-2-hydroxy-propyl)-2-hydroxy-acetamide (985 mg, 3.03 mmol). LC-MS**: $t_R$=0.78 min; [M+1]$^+$=481.82; $^1$H NMR (D$_6$-DMSO): δ 0.95 (t, J=7.3

Hz, 3H), 1.23 (t, J=7.5 Hz, 3H), 1.71 (h, J=7.5 Hz, 2H), 2.36 (s, 3H), 2.74 (q, J=7.5 Hz, 2H), 2.82 (t, J=7.5 Hz, 2H), 3.20-3.29 (m, 1H), 3.40-3.48 (m, 1H), 3.71-3.81 (m, 2H), 3.84 (d, J=4.8 Hz, 2H), 3.93-4.01 (m, 1H), 5.31 (d, J=5.0 Hz, 1H), 5.55 (t, J=5.3 Hz, 1H), 7.70 (t, J=5.5 Hz, 1H), 7.82 (s, 2H), 8.07 (s, 1H), 8.33 (s, 1H), 8.52 (s, 1H), 10.15 (s, 1H).

N—((S)-3-{2-ethyl-4-[5-(3-formyl-5-isopropyl-phenyl)-[1,2,4]oxadiazol-3-yl]-6-methyl-phenoxy}-2-hydroxy-propyl)-2-hydroxy-acetamide The title compound (49 mg) was prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 3-formyl-5-isopropyl-benzoic acid (250 mg, 1.30 mmol) and N—((S)-3-[2-ethyl-4-(N-hydroxycarbamimidoyl)-6-methyl-phenoxy]-2-hydroxy-propyl)-2-hydroxy-acetamide (423 mg, 1.30 mmol); LC-MS**: $t_R$=0.90 min; [M+1]$^+$=481.85.

rac-N-(3-{4-[5-(4-formyl-phenyl)-[1,2,4]oxadiazol-3-yl]-2,6-dimethyl-phenoxy}-2-hydroxy-propyl)-2-hydroxy-acetamide The title compound was prepared from rac-2-hydroxy-N-{2-hydroxy-3-[4-(N-hydroxycarbamimidoyl)-2,6-dimethyl-phenoxy]-propyl}-acetamide and 4-formyl-benzoic acid in analogy to (rac)-N-(3-{4-[5-(3-formyl-phenyl)-[1,2,4]oxadiazol-3-yl]-2,6-dimethyl-phenoxy}-2-hydroxy-propyl)-2-hydroxy-acetamide. LC-MS: $t_R$=0.88 min; [M+1]$^+$=426.36.

rac-N-(3-{4-[5-(4-formyl-3-methyl-phenyl)-[1,2,4]oxadiazol-3-yl]-2,6-dimethyl-phenoxy}-2-hydroxy-propyl)-2-hydroxy-acetamide The title compound was prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 4-formyl-3-methyl benzoic acid and rac-2-hydroxy-N-{2-hydroxy-3-[4-(N-hydroxycarbamimidoyl)-2,6-dimethyl-phenoxy]-propyl}-acetamide.

LC-MS: $t_R$=0.90 min; [M+1]$^+$=440.15; $^1$H NMR (D$_6$-DMSO): δ 2.35 (s, 6H), 2.77 (s, 3H), 3.20-3.28 (m, 1H), 3.40-3.49 (m, 1H), 3.71-3.81 (m, 2H), 3.84 (d, J=5.3 Hz, 2H), 3.92-3.99 (m, 1H), 5.30 (d, J=4.8 Hz, 1H), 5.55 (t, J=5.0 Hz, 1H), 7.70 (t, J=6.0 Hz, 1H), 7.80 (s, 2H), 8.07 (d, J=8.0 Hz, 1H), 8.17-8.23 (m, 2H), 10.37 (s, 1H).

N—((S)-3-{2-ethyl-4-[5-(4-formyl-3-methyl-phenyl)-[1,2,4]oxadiazol-3-yl]-6-methyl-phenoxy}-2-hydroxy-propyl)-2-hydroxy-acetamide The title compound was prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 4-formyl-3-methyl benzoic acid and N—((S)-3-[2-ethyl-4-(N-hydroxycarbamimidoyl)-6-methyl-phenoxy]-2-hydroxy-propyl)-2-hydroxy-acetamide. LC-MS: $t_R$=0.68 min; [M+1]$^+$=454.26; $^1$H NMR (D$_6$-DMSO): δ 1.24 (t, J=7.5 Hz, 3H), 2.36 (s, 3H), 2.78 (s, 3H), 3.23-3.30 (m, 1H), 3.41-3.48 (m, 1H), 3.72-3.81 (m, 2H), 3.84 (d, J=5.3 Hz, 2H), 3.94-4.01 (m, 1H), 5.32 (d, J=5.3 Hz, 1H), 5.56 (t, J=5.8 Hz, 1H), 7.71 (t, J=5.5 Hz, 1H), 7.82 (s, 2H), 8.08 (d, J=8.0 Hz, 1H), 8.19-8.24 (m, 2H), 10.37 (s, 1H).

Examples 1 to 6 (Method A)

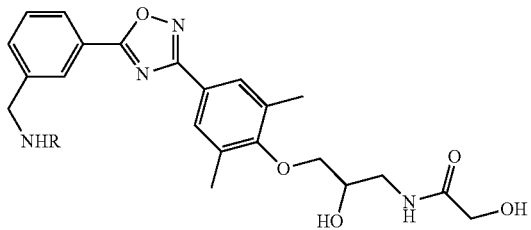

To a solution of rac-N-(3-{4-[5-(3-formyl-phenyl)-[1,2,4]oxadiazol-3-yl]-2,6-dimethyl-phenoxy}-2-hydroxy-propyl)-2-hydroxy-acetamide (8.5 mg, 20 μmol) in MeOH (1 mL) and NMP (0.2 mL), the appropriate amine (60 μmol, neat or as a solution in MeOH or ethanol) was added. The mixture was stirred at rt for 2 h before Na(BH$_3$CN) (5 mg, 80 μmol) and NaBH$_4$ (3 mg, 80 μmol) was added. Stirring was continued for 24 h before the mixture was separated by prep. HPLC (XBridge Prep C18, 50×20 mm ID, 5 μm, 80% to 10% water (containing 0.5% sat. ammonium hydroxide) in MeCN) to give the desired substituted rac-N-(3-{4-[5-(3-aminomethyl-phenyl)-[1,2,4]oxadiazol-3-yl]-2,6-dimethyl-phenoxy}-2-hydroxy-propyl)-2-hydroxy-acetamide.

|         |           | LC-MS*      |           |
|---------|-----------|-------------|-----------|
| Example | R         | $t_R$ (min) | [M + H]$^+$ |
| 1       | methyl    | 0.72        | 441.21    |
| 2       | ethyl     | 0.76        | 455.14    |
| 3       | n-propyl  | 0.80        | 469.16    |
| 4       | iso-propyl| 0.79        | 469.22    |
| 5       | n-butyl   | 0.85        | 483.22    |
| 6       | iso-butyl | 0.85        | 483.19    |

Examples 7 and 8

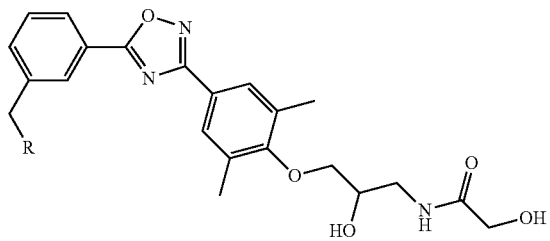

To a solution of rac-N-(3-{4-[5-(3-formyl-phenyl)-[1,2,4]oxadiazol-3-yl]-2,6-dimethyl-phenoxy}-2-hydroxy-propyl)-2-hydroxy-acetamide (8.5 mg, 20 μmol) in DCM (0.5 mL) and NMP (0.15 mL), the appropriate amine (60 μmol) followed by NaBH(OAc)$_3$ (17 mg, 80 μmol) was added. The mixture was stirred at rt for 24 h before the mixture was separated by prep. HPLC (XBridge Prep C18, 50×20 mm ID, 5 μm, 80% to 10% water (containing 0.5% sat. ammonium hydroxide) in MeCN) to give the desired substituted rac-N-(3-{4-[5-(3-aminomethyl-phenyl)-[1,2,4]oxadiazol-3-yl]-2,6-dimethyl-phenoxy}-2-hydroxy-propyl)-2-hydroxy-acetamide

| Example | R | LC-MS* t_R (min) | [M + H]+ |
|---|---|---|---|
| 7 | NMe₂ | 0.77 | 455.19 |
| 8 | NMeEt | 0.84 | 469.17 |

Examples 9 to 14

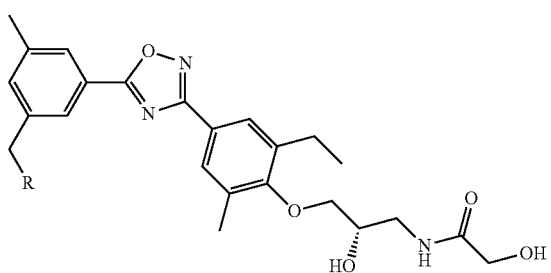

The following Example compounds were prepared starting from N—((S)-3-{2-ethyl-4-[5-(3-formyl-5-methyl-phenyl)-[1,2,4]oxadiazol-3-yl]-6-methyl-phenoxy}-2-hydroxy-propyl)-2-hydroxy-acetamide and the appropriate amines according to Method A:

| Example | R | LC-MS* t_R (min) | [M + H]+ |
|---|---|---|---|
| 9 | methyl | 0.51 | 469.12 |
| 10 | ethyl | 0.53 | 483.17 |
| 11 | n-propyl | 0.55 | 497.16 |
| 12 | iso-propyl | 0.54 | 497.18 |
| 13 | n-butyl | 0.58 | 511.23 |
| 14 | iso-butyl | 0.57 | 511.27 |

Examples 15 to 22

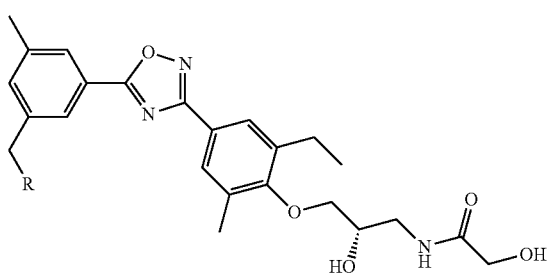

The following Example compounds were prepared starting from N—((S)-3-{2-ethyl-4-[5-(3-formyl-5-methyl-phenyl)-[1,2,4]oxadiazol-3-yl]-6-methyl-phenoxy}-2-hydroxy-propyl)-2-hydroxy-acetamide and the appropriate amines according to Method A:

| Example | R | LC-MS* t_R (min) | [M + H]+ |
|---|---|---|---|
| 15 |  | 0.52 | 483.17 |
| 16 |  | 0.54 | 497.14 |
| 17 |  | 0.56 | 511.23 |
| 18 |  | 0.59 | 525.24 |
| 19 |  | 0.58 | 525.25 |
| 20 |  | 0.55 | 511.21 |
| 21 |  | 0.54 | 539.29 |
| 22 |  | 0.54 | 509.21 |

Example 15

$^1$H NMR (D₆-DMSO): δ 1.23 (t, J=7.3 Hz, 3H), 2.22 (s, 6H), 2.35 (s, 3H), 2.45 (s, 3H), 2.73 (q, J=7.3 Hz, 2H), 3.20-3.28 (m, 1H), 3.40-3.48 (m, 1H), 3.52 (br s, 2H), 3.70-3.80 (m, 2H), 3.84 (d, J=5.5 Hz, 2H), 3.93-4.00 (m, 1H), 5.31 (d, J=5.3 Hz, 1H), 5.55 (t, J=5.8 Hz, 1H), 7.47 (s, 1H), 7.70 (t, J=5.8 Hz), 7.80 (s, 2H), 7.92 (s, 1H), 7.94 (s, 1H).

Example 19

$^1$H NMR (D₆-DMSO): δ 0.89 (d, J=6.5 Hz, 6H) 1.23 (t, J=7.5 Hz, 3H), 1.78-1.88 (m, 1H), 2.12 (d, J=7.3 Hz, 2H), 2.15 (s, 3H), 2.35 (s, 3H), 2.44 (s, 3H), 2.73 (q, J=7.8 Hz, 2H), 3.21-3.29 (m, 1H), 3.40-3.48 (m, 1H), 3.54 (s, 2H), 3.70-3.80 (m, 2H), 3.84 (d, J=5.5 Hz, 2H), 3.93-3.99 (m, 1H), 5.31 (d, J=5.0 Hz, 1H), 5.55 (t, J=5.5 Hz, 1H), 7.47 (s, 1H), 7.70 (t, J=5.5 Hz, 1H), 7.79 (s, 2H), 7.90 (s, 1H), 7.94 (s, 1H).

Example 22

$^1$H NMR (D₆-DMSO): δ 1.23 (t, J=7.5 Hz, 3H), 1.70-1.76 (m, 4H), 2.35 (s, 3H), 2.44 (s, 3H), 2.46-2.49 (m, 4H), 2.73 (q, J=7.8 Hz, 2H), 3.21-3.29 (m, 1H), 3.39-3.47 (m, 1H), 3.68 (s, 2H), 3.70-3.80 (m, 2H), 3.84 (d, J=5.5 Hz, 2H), 3.94-3.99 (m, 1H), 5.31 (d, J=5.3 Hz, 1H), 5.55 (t, J=5.8 Hz, 1H), 7.48 (s, 1H), 7.70 (t, J=6.0 Hz, 1H), 7.80 (s, 2H), 7.90 (s, 1H), 7.93 (s, 1H).

Example 23 rac-N-(3-{4-[5-(4-dimethylaminomethyl-phenyl)-[1,2,4]oxadiazol-3-yl]-2,6-di-methyl-phenoxy}-2-hydroxy-propyl)-2-hydroxy-acetamide The title compound was prepared starting from rac-N-(3-{4-[5-(4-formyl-phenyl)-[1,2,4]oxadiazol-3-yl]-2,6-dimethyl-phenoxy}-2-hydroxy-propyl)-2-hydroxy-acetamide and dimethyl amine according to Method B. LC-MS*: $t_R$=0.78 min; [M+1]$^+$=455.38, $^1$H NMR (CDCl$_3$): δ2.30 (s, 6H), 2.38 (s, 6H), 3.47-3.53 (m, 1H), 3.54 (s, 2H), 3.75-3.93 (m, 3H), 4.16-4.25 (m, 3H), 7.00 (br s, 1H), 7.53 (d, J=7.8 Hz, 2H), 7.86 (s, 2H), 8.19 (d, J=7.3 Hz, 2H).

Examples 24 to 29

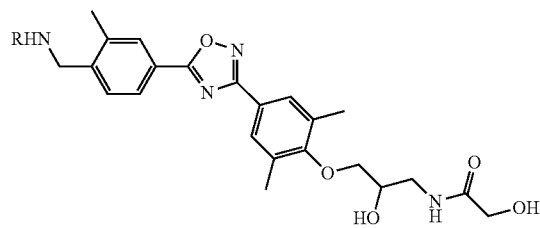

The following Example compounds were prepared following Method A starting from rac-N-(3-{4-[5-(4-Formyl-3-methyl-phenyl)-[1,2,4]oxadiazol-3-yl]-2,6-dimethyl-phenoxy}-2-hydroxy-propyl)-2-hydroxy-acetamide and the appropriate primary amines:

| Example | R | LC-MS $t_R$ (min) | [M + H]$^+$ |
|---|---|---|---|
| 24 | methyl | 0.48 | 455.17 |
| 25 | ethyl | 0.49 | 469.17 |
| 26 | n-propyl | 0.52 | 483.19 |
| 27 | iso-propyl | 0.51 | 483.20 |
| 28 | n-butyl | 0.54 | 497.13 |
| 29 | iso-butyl | 0.54 | 497.15 |

Examples 30 to 36

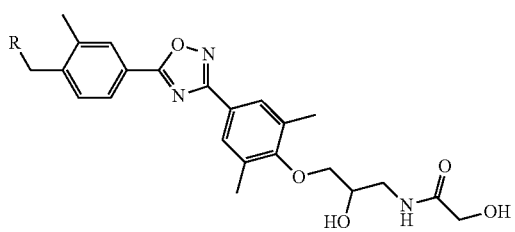

The following Example compounds were prepared following Method B starting from rac-N-(3-{4-[4-(4-formyl-3-methyl-phenyl)-[1,2,4]oxadiazol-3-yl]-2,6-dimethyl-phenoxy}-2-hydroxy-propyl)-2-hydroxy-acetamide and the appropriate secondary amines:

| Example | R | LC-MS $t_R$ (min) | [M + H]$^+$ |
|---|---|---|---|
| 30 | N-ethyl (N-methyl) | 0.50 | 483.12 |
| 31 | N-propyl (N-methyl) | 0.53 | 497.16 |
| 32 | N-butyl (N-methyl) | 0.55 | 511.23 |
| 33 | N-isobutyl (N-methyl) | 0.54 | 511.18 |
| 34 | N,N-diethyl | 0.52 | 497.12 |
| 35 | N-butyl (N-ethyl) | 0.57 | 525.22 |
| 36 | pyrrolidinyl | 0.51 | 495.20 |

Example 37 rac-N-(3-{4-[5-(4-dimethylaminomethyl-3-methoxy-phenyl)-[1,2,4]oxadiazol-3-yl]-2,6-dimethyl-phenoxy}-2-hydroxy-propyl)-2-hydroxy-acetamide The title compound was prepared in analogy to rac-N-(3-{4-[5-(3-formyl-phenyl)-[1,2,4]oxadiazol-3-yl]-2,6-dimethyl-phenoxy}-2-hydroxy-propyl)-2-hydroxy-acetamide, starting from 4-dimethylaminomethyl-3-methoxy-benzoic acid and rac-2-hydroxy-N-{2-hydroxy-3-[4-(N-hydroxycarbamimidoyl)-2,6-dimethyl-phenoxy]-propyl}-acetamide. LC-MS: $t_R$=0.71 min; [M+1]$^+$=485.27; $^1$H NMR (CDCl$_3$): δ2.36 (s, 6H), 2.54 (s, 6H), 3.45-3.54 (m, 1H), 3.74-3.91 (m, 3H), 3.92 (s, 2H), 4.01 (s, 3H), 4.15-4.20 (m, 3H), 7.13 (t, J=5.8 Hz, 1H), 7.60 (d, J=8.0 Hz, 1H), 7.72 (s, 1H), 7.81-7.86 (m, 3H), 8.50 (s, 1H) (as formate salt).

Examples 38 to 45

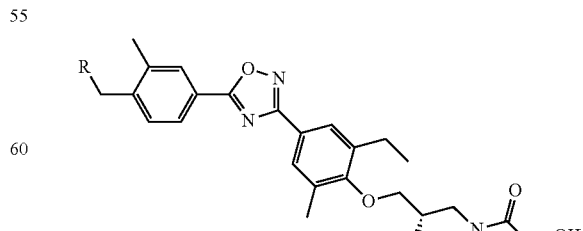

The following Example compounds were prepared following Method A or B starting from N—((S)-3-{2-ethyl-4-[5-(4- formyl-3-methyl-phenyl)-[1,2,4]oxadiazol-3-yl]-6-methyl-phenoxy}-2-hydroxy-propyl)-2-hydroxy-acetamide and the appropriate amines:

| Example | R | Method used | LC-MS** $t_R$ (min) | [M + H]+ |
|---|---|---|---|---|
| 38 | HN–CH2CH2CH3 | A | 0.48 | 497.46 |
| 39 | HN–CH(CH3)2 | A | 0.50 | 511.32 |
| 40 | N(CH3)2 | B | 0.45 | 483.30 |
| 41 | N(CH3)(C2H5) | B | 0.46 | 497.83 |
| 42 | N(CH3)(propyl) | B | 0.51 | 525.34 |
| 43 | N(CH3)(isobutyl) | B | 0.50 | 525.36 |
| 44 | N(C2H5)2 | B | 0.47 | 511.31 |
| 45 | pyrrolidine | B | 0.47 | 509.30 |

Examples 46 to 55

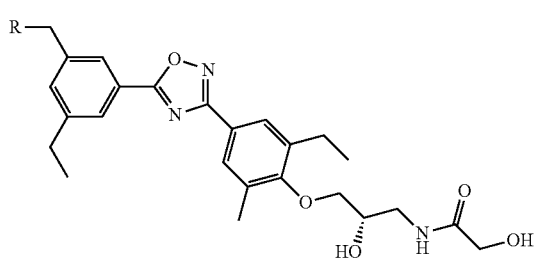

The following Example compounds were prepared following Method A or B starting from N—((S)-3-{2-ethyl-4-[5-(3-formyl-5-ethyl-phenyl)-[1,2,4]oxadiazol-3-yl]-6-methyl-phenoxy}-2-hydroxy-propyl)-2-hydroxy-acetamide and the appropriate amines:

| Example | R | Method used | LC-MS** $t_R$ (min) | [M + H]+ |
|---|---|---|---|---|
| 46 | HN–CH2CH2CH3 | A | 0.52 | 511.29 |
| 47 | HN–CH2CH2CH3 | A | 0.55 | 525.26 |
| 48 | HN–CH(CH3)2 | A | 0.54 | 525.26 |
| 49 | N(CH3)2 | B | 0.50 | 497.88 |
| 50 | N(CH3)(C2H5) | B | 0.51 | 511.27 |
| 51 | N(CH3)(C2H5) | B | 0.53 | 525.26 |
| 52 | N(CH3)(propyl) | B | 0.56 | 539.26 |
| 53 | N(CH3)(isobutyl) | B | 0.55 | 539.33 |
| 54 | N(C2H5)2 | B | 0.52 | 525.32 |
| 55 | pyrrolidine | B | 0.51 | 523.26 |

Example 53

$^1$H NMR (D$_6$-DMSO): δ 0.89 (d, J=6.5 Hz, 6H), 1.23 (t, J=7.8 Hz, 3H), 1.25 (t, J=7.5 Hz, 3H), 1.79-1.89 (m, 1H), 2.11 (d, J=7.0 Hz, 2H), 2.17 (s, 3H), 2.35 (s, 3H), 2.74 (quint, J=7.5 Hz, 4H), 3.21-3.29 (m, 1H), 3.40-3.49 (m, 1H), 3.56 (s, 2H), 3.71-3.80 (m, 2H), 3.84 (d, J=3.0 Hz, 2H), 3.93-4.01 (m, 1H), 5.30 (br s, 1H), 5.55 (br s, 1H), 7.51 (s, 1H), 7.70 (t, J=5.5 Hz, 1H), 7.80 (s, 2H), 7.91 (s, 1H), 7.96 (s, 1H).

Examples 56 to 65

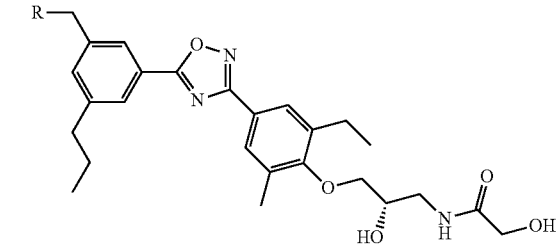

The following Example compounds were prepared following Method A or B starting from N—((S)-3-{2-ethyl-4-[5-(3- formyl-5-propyl-phenyl)-[1,2,4]oxadiazol-3-yl]-6-methyl-phenoxy}-2-hydroxy-propyl)-2-hydroxy-acetamide and the appropriate amines:

| Example | R | Method used | LC-MS** t$_R$ (min) | LC-MS* |
|---|---|---|---|---|
| 56 | HN–CH₂CH₃ | A | 0.56 | 525.23 |
| 57 | HN–propyl | A | 0.58 | 539.27 |
| 58 | HN–isopropyl | A | 0.57 | 539.28 |
| 59 | N(CH₃)–CH₃ | B | 0.53 | 511.13 |
| 60 | N(CH₃)–C₂H₅ | B | 0.54 | 525.32 |
| 61 | N(CH₃)–propyl | B | 0.56 | 539.29 |
| 62 | N(CH₃)–butyl | B | 0.59 | 553.35 |
| 63 | N(CH₃)–isobutyl | B | 0.58 | 553.33 |
| 64 | N(C₂H₅)₂ | B | 0.55 | 539.34 |
| 65 | pyrrolidine | B | 0.55 | 537.31 |

Example 62

$^1$H NMR (D$_6$-DMSO): δ 0.87 (t, J=7.3 Hz, 3H), 0.93 (t, J=7.3 Hz, 3H), 1.23 (t, J=7.5 Hz, 3H), 1.27-1.37 (m, 2H), 1.43-1.52 (m, 2H), 1.66 (h, J=7.3 Hz, 2H), 2.16 (s, 3H), 2.32-2.39 (m, 5H), 2.66-2.78 (m, 4H), 3.21-3.29 (m, 1H), 3.39-3.48 (m, 1H), 3.56 (s, 2H), 3.70-3.81 (m, 2H), 3.84 (d, J=5.5 Hz, 2H), 3.93-4.01 (m, 1H), 5.31 (d, J=5.3 Hz, 1H), 5.55 (t, J=5.8 Hz, 1H), 7.48 (s, 1H), 7.70 (t, J=5.8 Hz, 1H), 7.80 (s, 2H), 7.89 (s, 1H), 7.94 (s, 1H).

Examples 66 to 75

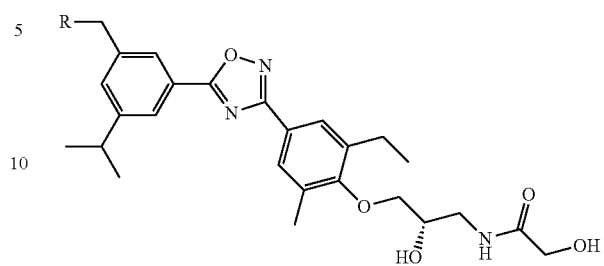

The following Example compounds were prepared following Method A or B starting from N—((S)-3-{2-ethyl-4-[5-(3-formyl-5-isopropyl-phenyl)-[1,2,4]oxadiazol-3-yl]-6-methyl-phenoxy}-2-hydroxy-propyl)-2-hydroxy-acetamide and the appropriate amines:

| Example | R | Method used | LC-MS** t$_R$ (min) | [M + H]$^+$ |
|---|---|---|---|---|
| 66 | HN–CH₂CH₃ | A | 0.55 | 525.27 |
| 67 | HN–propyl | A | 0.57 | 539.25 |
| 68 | HN–isopropyl | A | 0.57 | 539.27 |
| 69 | N(CH₃)–CH₃ | B | 0.52 | 511.28 |
| 70 | N(CH₃)–C₂H₅ | B | 0.53 | 525.27 |
| 71 | N(CH₃)–propyl | B | 0.56 | 539.30 |
| 72 | N(CH₃)–butyl | B | 0.58 | 553.32 |
| 73 | N(CH₃)–isobutyl | B | 0.57 | 553.32 |
| 74 | N(C₂H₅)₂ | B | 0.55 | 539.28 |
| 75 | pyrrolidine | B | 0.54 | 537.26 |

Example 71

$^1$H NMR (D$_6$-DMSO): δ 0.89 (t, J=7.3 Hz, 3H), 1.24 (t, J=7.3 Hz, 3H), 1.29 (d, J=7.0 Hz, 6H), 1.51 (h, J=6.8 Hz, 2H), 2.18 (s, 3H), 2.33 (m, 5H), 2.74 (q, J=7.5 Hz, 2H), 3.02-3.12 (m, 1H), 3.22-3.30 (m, 1H), 3.41-3.48 (m, 1H), 3.59 (s, 2H), 3.71-3.81 (m, 2H), 3.85 (s, 2H), 3.94-4.01 (m, 1H), 5.30 (br s, 1H), 5.55 (br s, 1H), 7.55 (s, 1H), 7.70 (t, J=5.5 Hz, 1H), 7.81 (s, 2H), 7.93 (s, 1H), 7.96 (s, 1H).

Examples 76 to 85

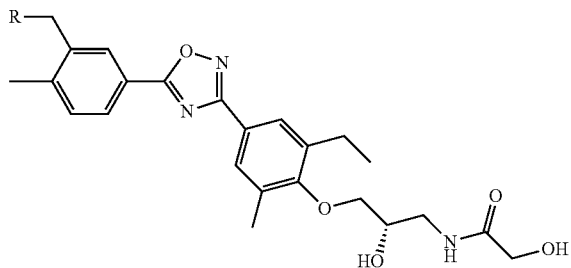

The following Example compounds were prepared following Method A or B starting from N—((S)-3-{2-ethyl-4-[5-(3-formyl-4-methyl-phenyl)-[1,2,4]oxadiazol-3-yl]-6-methyl-phenoxy}-2-hydroxy-propyl)-2-hydroxy-acetamide and the appropriate amines:

| Example | R | Method used | $t_R$ (min) | $[M + H]^+$ |
|---|---|---|---|---|
| 76 | HN-propyl | A | 0.49 | 497.12 |
| 77 | HN-butyl | A | 0.51 | 511.13 |
| 78 | HN-isopropyl | A | 0.50 | 511.27 |
| 79 | N-methyl,methyl | B | 0.46 | 484.25 |
| 80 | N-methyl,ethyl | B | 0.47 | 497.04 |
| 81 | N-methyl,propyl | B | 0.49 | 511.22 |
| 82 | N-methyl,butyl | B | 0.52 | 525.22 |
| 83 | N-methyl,isobutyl | B | 0.51 | 525.29 |
| 84 | N-ethyl,ethyl | B | 0.48 | 511.26 |
| 85 | pyrrolidinyl | B | 0.48 | 509.25 |

Examples 86 to 95

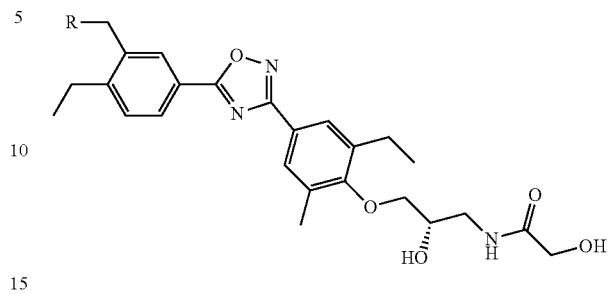

The following Example compounds were prepared following Method A or B starting from N—((S)-3-{2-ethyl-4-[5-(3-formyl-4-ethyl-phenyl)-[1,2,4]oxadiazol-3-yl]-6-methyl-phenoxy}-2-hydroxy-propyl)-2-hydroxy-acetamide and the appropriate amines:

| Example | R | Method used | $t_R$ (min) | $[M + H]^+$ |
|---|---|---|---|---|
| 86 | HN-propyl | A | 0.52 | 511.22 |
| 87 | HN-butyl | A | 0.54 | 525.29 |
| 88 | HN-isopropyl | A | 0.53 | 525.27 |
| 89 | N-methyl,methyl | B | 0.49 | 497.06 |
| 90 | N-methyl,ethyl | B | 0.50 | 511.29 |
| 91 | N-methyl,propyl | B | 0.52 | 525.24 |
| 92 | N-methyl,butyl | B | 0.55 | 539.30 |
| 93 | N-methyl,isobutyl | B | 0.54 | 539.31 |
| 94 | N-ethyl,ethyl | B | 0.51 | 525.31 |
| 95 | pyrrolidinyl | B | 0.51 | 523.26 |

Examples 96 to 105

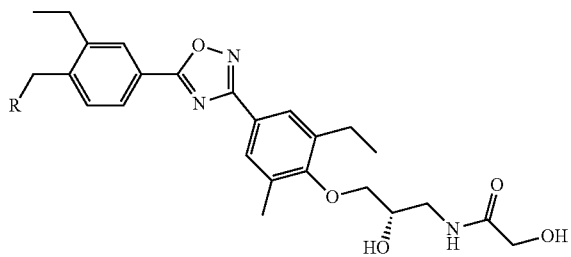

The following Example compounds were prepared following Method A or B starting from N—((S)-3-{2-ethyl-4-[5-(3-ethyl-4-formyl-phenyl)-[1,2,4]oxadiazol-3-yl]-6-methyl-phenoxy}-2-hydroxy-propyl)-2-hydroxy-acetamide and the appropriate amines:

| Example | R | Method used | $t_R$ (min) | $[M + H]^+$ |
|---|---|---|---|---|
| 96 | HN-CH2CH2CH3 | A | 0.50 | 511.32 |
| 97 | HN-CH2CH2CH2CH3 | A | 0.53 | 525.27 |
| 98 | HN-CH(CH3)CH2CH3 | A | 0.52 | 525.34 |
| 99 | N(CH3)- | B | 0.47 | 497.12 |
| 100 | N(CH3)CH2CH3 | B | 0.49 | 511.28 |
| 101 | N(CH3)CH2CH2CH3 | B | 0.51 | 525.29 |
| 102 | N(CH3)CH2CH2CH2CH3 | B | 0.53 | 539.27 |
| 103 | N(CH3)CH2CH(CH3)2 | B | 0.53 | 539.27 |
| 104 | N(CH2CH3)2 | B | 0.50 | 525.26 |
| 105 | pyrrolidinyl | B | 0.49 | 523.23 |

Example 99

$^1$H NMR (D$_6$-DMSO): δ 1.23 (t, J=7.5 Hz, 3H), 1.24 (t, J=7.3 Hz, 3H), 2.20 (s, 6H), 2.35 (s, 3H), 2.74 (q, J=7.5 Hz, 2H), 2.83 (q, J=7.5 Hz, 2H), 3.21-3.29 (m, 1H), 3.41-3.48 (m, 1H), 3.49 (s, 2H), 3.71-3.80 (m, 2H), 3.84 (d, J=5.8 Hz, 2H), 3.94-4.00 (m, 1H), 5.30 (d, J=5.3 Hz, 1H), 5.55 (t, J=5.8 Hz, 1H), 7.57 (d, J=7.8 Hz, 1H), 7.70 (t, J=5.8 Hz, 1H), 7.80 (s, 2H), 7.97-8.02 (m, 2H).

Example 106

2-ethyl-4-(5-{3-[(ethyl-methyl-amino)-methyl]-5-methyl-phenyl}-[1,2,4]oxadiazol-3-yl)-6-methyl-phenol The title compound (2.14 g) was prepared starting from 3-[3-(3-ethyl-4-hydroxy-5-methyl-phenyl)-[1,2,4]oxadiazol-5-yl]-5-methyl-benzaldehyde (2.13 g, 6.61 mmol) and N-ethyl-methylamine (1.56 g, 26.4 mmol) according to Method B. LC-MS: $t_R$=0.61 min; $[M+1]^+$=366.22; $^1$H NMR δ 1.06 (t, J=7.0 Hz, 3H), 1.19 (t, J=7.3 Hz, 3H), 2.14 (s, 3H), 2.28 (s, 3H), 2.41-2.48 (m, 5H), 2.65-2.72 (m, 2H), 3.54 (s, 2H), 7.46 (s, 1H), 7.67-7.71 (m, 2H), 7.89 (s, 1H), 7.93 (s, 1H), 8.93 (s, 1H).

Example 107

2-[4-(5-{3-[(ethyl-methyl-amino)-methyl]-5-methyl-phenyl}-[1,2,4]oxadiazol-3-yl)-2,6-dimethyl-phenoxy]-ethylamine 2-(Boc-amino)-ethylbromide (66 mg, 285 µmol) was added to a suspension of 2-ethyl-4-(5-{3-[(ethyl-methyl-amino)-methyl]-5-methyl-phenyl}-[1,2,4]oxadiazol-3-yl)-6-methyl-phenol (52 mg, 142 µmol) and K$_2$CO$_3$ (60 mg, 427 µmol) in acetonitrile (2 mL). The mixture was stirred at 70° C. for 16 h before it was filtered. The filtrate was concentrated, dissolved in DCM (1 mL) and TFA (1 mL) and stirred at rt for 10 min. The mixture was again concentrated in vacuo and the crude product was purified by prep. HPLC to give the title compound as a formate salt in the form of a white lyophilisate (40 mg). LC-MS: $t_R$=0.47 min; $[M+1]^+$=409.30; $^1$H NMR (D$_6$-DMSO): δ 1.06 (t, J=7.0 Hz, 3H), 1.26 (t, J=7.5 Hz, 3H), 2.16 (s, 3H), 2.38 (s, 3H), 2.43-2.48 (m, 5H), 2.75 (q, J=7.5 Hz, 2H), 3.26 (t, J=5.0 Hz, 2H), 3.56 (s, 2H), 3.99 (t, J=5.0 Hz, 2H), 7.48 (s, 1H), 7.83 (s, 2H), 7.91 (s, 1H), 7.93 (s, 1H), 8.17 (s, 2H, formate).

Example 108

2-[4-(5-{3-[(ethyl-methyl-amino)-methyl]-5-methyl-phenyl}-[1,2,4]oxadiazol-3-yl)-2,6-dimethyl-phenoxy]-ethanol (2-bromoethoxy)-tert-butyl-dimethylsilane (104 mg, 435 µmol) was added to a suspension of 2-ethyl-4-(5-{3-[(ethyl-methyl-amino)-methyl]-5-methyl-phenyl}-[1,2,4]oxadiazol-3-yl)-6-methyl-phenol (53 mg, 145 µmol) and K$_2$CO$_3$ (60 mg, 435 µmol) in acetonitrile (2 mL). The mixture was stirred at 70° C. for 16 h before it was filtered. The filtrate was diluted with 1N aq. HCl (0.1 mL) and 2N aq. HCl (0.1 mL). The mixture was allowed to stand at rt for 10 min before the solvent was removed in vacuo. The crude product was purified by prep. HPLC to give the title compound as a formate salt in the form of a white lyphilisate (29 mg). LC-MS: $t_R$=0.59 min; $[M+1]^+$=410.26; $^1$H NMR (D$_6$-DMOS): δ 1.06

(t, J=7.3 Hz, 3H), 1.23 (t, J=7.3 Hz, 3H), 2.15 (s, 3H), 2.36 (s, 3H), 2.42-2.48 (m, 5H), 2.75 (q, J=7.5 Hz, 2H), 3.56 (s, 2H), 3.73-3.77 (m, 2H), 3.84-3.89 (m, 2H), 7.47 (s, 1H), 7.80 (s, 2H), 7.90 (s, 1H), 7.92 (s, 1H), 8.17 (s, 1H, formate).

Example 109

4-[4-(5-{3-[(ethyl-methyl-amino)-methyl]-5-methyl-phenyl}-[1,2,4]oxadiazol-3-yl)-2,6-dimethyl-phenoxy]-butan-1-ol 4-bromobutyl acetate (186 mg, 936 μmol) was added to a suspension of 2-ethyl-4-(5-{3-[(ethyl-methyl-amino)-methyl]-5-methyl-phenyl}-[1,2,4]oxadiazol-3-yl)-6-methyl-phenol (114 mg, 312 μmol) and K₂CO₃ (129 mg, 936 μmol) in acetonitrile (2 mL). The mixture was stirred at 70° C. for 2 h before it was filtered. The filtrate was diluted with 25% aq. ammonia (0.5 mL) and a 32% aq. NaOH solution (300 μL) and the bi-phasic mixture was stirred at 70° C. for 2 h. The aq. phase was separated and 1N aq. NaOH (0.4 mL) was added. The now homogenous mixture was separated by prep. HPLC (XBridge 30×75 mm, eluting with a gradient of MeCN in water containing 0.5% of sat. aq. ammonia) to give the title compound as a white lyophilisate (53 mg). LC-MS: $t_R$=0.65 min; [M+1]⁺=438.25; ¹H NMR (D₆-DMSO): δ 1.06 (t, J=7.0 Hz, 3H), 1.23 (t, J=7.5 Hz, 3H), 1.61-1.69 (m, 2H), 1.78-1.86 (m, 2H), 2.15 (s, 3H), 2.34 (s, 3H), 2.41-2.48 (m, 5H), 2.71 (q, J=7.5 Hz, 2H), 3.47-3.53 (m, 2H), 3.55 (s, 2H), 3.81-3.86 (m, 2H), 4.47 (br s, 1H), 7.47 (s, 1H), 7.80 (s, 2H), 7.90 (s, 1H), 7.93 (s, 1H).

Example 110

2-[4-(5-{3-[(ethyl-methyl-amino)-methyl]-5-methyl-phenyl}-[1,2,4]oxadiazol-3-yl)-2,6-dimethyl-phenoxy]-propane-1,3-diol To a solution of 2-ethyl-4-(5-{3-[(ethyl-methyl-amino)-methyl]-5-methyl-phenyl}-[1,2,4]oxadiazol-3-yl)-6-methyl-phenol (100 mg, 273 μmol) in THF (2 mL), PPh₃ (107 mg, 409 μmol) followed by 2,2-dimethyl-[1,3]dioxan-5-ol (54 mg, 409 μmol) was added. The mixture was stirred at 0° C. for 10 min before DEAD (178 mg, 409 μmol, 188 μL of a 40% solution in toluene) was added. Stirring was continued at rt for 16 h. Another portion of PPh₃ (107 mg, 409 μmol) and DEAD (178 mg, 409 μmol) was added and the mixture was stirred at rt for another hour. The solvent was removed in vacuo and the residue was dissolved in MeCN and separated by prep. HPLC. The acetal intermediate containing fractions were combined and concentrated. The residue was dissolved in MeCN (0.5 mL) and 1N aq. HCl (0.4 mL) and allowed to stand at rt for 10 min before it was again purified by prep. HPLC to give the title compound as a formate salt in the form of a white lyophilisate (71 mg). LC-MS: $t_R$=0.55 min; [M+1]⁺=440.22; ¹H NMR (D₆-DMSO): δ 1.06 (t, J=7.0 Hz, 3H), 1.21 (t, J=7.5 Hz, 3H), 2.15 (s, 3H), 2.37 (s, 3H), 2.42-2.48 (m, 5H), 2.78 (q, J=7.5 Hz, 2H), 3.56 (s, 2H), 3.60 (dd, J=11.5 Hz, 5.3 Hz, 2H), 3.64 (dd, J=11.5, 5.0 Hz, 2H), 3.98 (quint, J=5.3 Hz, 1H), 4.77 (br s, 1H), 7.47 (s, 1H), 7.76-7.79 (m, 2H), 7.90 (s, 1H), 7.93 (s, 1H), 8.18 (s, 1H, formate).

Examples 111 to 121

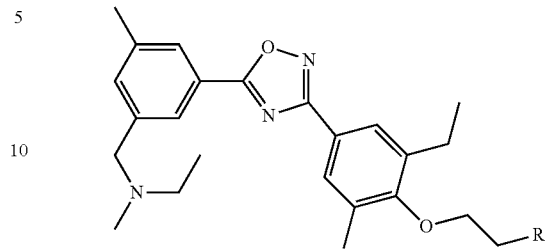

a) To a cooled (0° C.) solution of 2-[4-(5-{3-[(ethyl-methyl-amino)-methyl]-5-methyl-phenyl}-[1,2,4]oxadiazol-3-yl)-2,6-dimethyl-phenoxy]-ethanol (1.46 g, 2.91 mmol) in DCM (50 mL), triethylamine (942 mg, 9.32 mmol) was slowly added, followed by methanesulfonylchloride (400 mg, 3.49 mmol). The mixture was stirred at 5° C. for 10 min then at rt for 20 min.

Another portion of triethylamine (295 mg, 2.91 mmol) was added, followed by methanesulfonylchloride (400 mg, 3.49 mmol), and stirring was continued at rt for 10 min. Yet another portion of triethylamine (295 mg, 2.91 mmol) was added, followed by methanesulfonylchloride (200 mg, 1.75 mmol). The mixture was stirred for further 30 min before it was concentrated, dissolved in MeCN and separated by prep. HPLC (X-Bridge, 50×50 mm+100×50 mm, eluting with a gradient of MeCN in water containing 0.5% of sat. aq. ammonia) to give methanesulfonic acid 2-[2-ethyl-4-(5-{3-[(ethyl-methyl-amino)-methyl]-5-methyl-phenyl}-[1,2,4]oxadiazol-3-yl)-6-methyl-phenoxy]-ethyl ester as a pale yellow resin (1.07 g). LC-MS*: $t_R$=1.14 min; [M+1]⁺=488.11; ¹H NMR (D₆-DMSO): δ 1.06 (t, J=7.0 Hz, 3H), 1.24 (t, J=7.5 Hz, 3H), 2.15 (s, 3H), 2.37 (s, 3H), 2.41-2.49 (m, 5H), 2.75 (q, J=7.0 Hz, 2H), 3.27 (s, 3H), 3.55 (s, 2H), 4.10-4.15 (m, 2H), 4.53-4.58 (m, 2H), 7.47 (s, 1H), 7.82 (s, 2H), 7.90 (s, 1H), 7.93 (s, 1H).

b) To a solution of methanesulfonic acid 2-[2-ethyl-4-(5-{3-[(ethyl-methyl-amino)-methyl]-5-methyl-phenyl}-[1,2,4]oxadiazol-3-yl)-6-methyl-phenoxy]-ethyl ester (58 mg, 120 μmol) in acetonitrile (1 mL), the appropriate amine (840 μmol) was added. The amino acids were used as their hydrochloride salts and DIPEA (840 μmol), followed by NMP (1 mL) and DMF (1 mL), was added to these reaction mixtures. The mixture was stirred at 70° C. for 3 h. The mixture is filtered, the filtrate was separated by prep. HPLC to give the desired compound as a colourless resin (1-37 mg).

The following Example compounds were prepared using the procedures mentioned in steps a) and b) described above:

| | | LC-MS** | |
|---|---|---|---|
| Example | R | $t_R$ (min) | [M + H]⁺ |
| 111 | HN⟋ | 0.49 | 423.21 |
| 112 | HN⟋⟍ | 0.51 | 437.12 |
| 113 | N⟋⟍ | 0.50 | 437.19 |

-continued

| Example | R | LC-MS** t$_R$ (min) | [M + H]$^+$ |
|---|---|---|---|
| 114 | ![structure] | 0.52 | 451.11 |
| 115 | HN~~OH | 0.48 | 453.18 |
| 116 | N~~OH | 0.49 | 467.18 |
| 117 | HN~~~OH | 0.49 | 467.18 |
| 118 | HN~~NH$_2$ | 0.43 | 566.29 |
| 119 | HN-CH$_2$-C(O)O-CH$_3$ | 0.51 | 481.28 |
| 120 | N(CH$_3$)-CH$_2$-C(O)O-CH$_3$ | 0.53 | 495.31 |
| 121 | N-CH$_2$CH$_2$-C(O)O-CH$_3$ | 0.53 | 495.39 |

Example 112

$^1$H NMR (D$_6$-DMSO): δ 1.06 (t, J=7.0 Hz, 3H), 1.07 (t, J=7.3 Hz, 3H), 1.24 (t, J=7.5 Hz, 3H), 2.14 (s, 3H), 2.36 (s, 3H), 2.44 (m, 5H), 2.67 (q, J=7.0 Hz, 2H), 2.74 (q, J=7.5 Hz, 2H), 2.94 (t, J=5.8 Hz, 2H), 3.55 (s, 2H), 3.88 (t, J=5.8 Hz, 2H), 7.47 (s, 1H), 7.80 (s, 2H), 7.90 (s, 1H), 7.92 (s, 1H).

Example 116

$^1$H NMR (D$_6$-DMSO): δ 1.06 (t, J=7.0 Hz, 3H), 1.23 (t, J=7.5 Hz, 3H), 2.14 (s, 3H), 2.32 (s, 3H), 2.36 (s, 3H), 2.41-2.48 (m, 5H), 2.54 (t, J=6.5 Hz, 2H), 2.74 (q, J=7.5 Hz, 2H), 2.81 (t, J=6.0 Hz, 2H), 3.51 (q, J=6.3 Hz, 2H), 3.55 (s, 2H), 3.90 (t, J=6.0 Hz, 2H), 4.36 (t, J=5.5 Hz, 1H), 7.47 (s, 1H), 7.80 (s, 2H), 7.90 (s, 1H), 7.92 (s, 1H).

Example 117

$^1$H NMR (D$_6$-DMSO): δ 1.06 (t, J=7.3 Hz, 3H), 1.23 (t, J=7.5 Hz, 3H), 1.62 (quint, J=6.5 Hz, 2H), 2.14 (s, 3H), 2.36 (s, 3H), 2.40-2.48 (m, 5H), 2.72 (m, 4H), 2.94 (t, J=5.5 Hz, 2H), 3.50 (t, J=6.3 Hz, 2H), 3.55 (s, 2H), 3.89 (t, J=5.5 Hz, 2H), 7.47 (s, 1H), 7.80 (s, 2H), 7.90 (s, 1H), 7.92 (s, 1H).

Example 120

$^1$H NMR (D$_6$-DMSO): δ 1.06 (t, J=7.0 Hz, 3H), 1.23 (t, J=7.5 Hz, 3H), 2.14 (s, 3H), 2.35 (s, 3H), 2.41-2.47 (m, 8H), 2.73 (q, J=7.5 Hz, 2H), 2.96 (t, J=5.8 Hz, 2H), 3.45 (s, 2H), 3.55 (s, 2H), 3.64 (s, 3H), 3.91 (t, J=5.8 Hz, 2H), 7.47 (s, 1H), 7.80 (s, 2H), 7.90 (s, 1H), 7.92 (s, 1H).

Examples 122 to 126

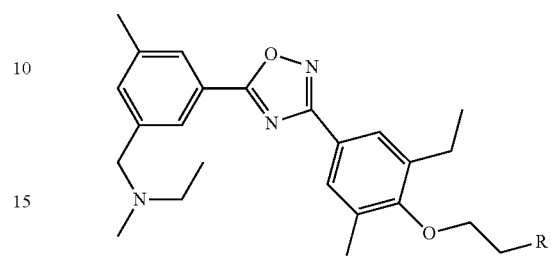

Methanesulfonic acid 2-[2-ethyl-4-(5-{3-[(ethyl-methyl-amino)-methyl]-5-methyl-phenyl}-[1,2,4]oxadiazol-3-yl)-6-methyl-phenoxy]-ethyl ester (58 mg, 120 μmol) is reacted with the appropriate amino acid ester hydrochloride (840 μmol) as described for Examples 119 to Examples 121. Upon completion of the reaction, water or 1N aq. NaOH is added and the mixture is stirred at rt for 3 to 16 h. The mixture is separated by prep. HPLC to give the desired amino acid derivatives as lyophilisates.

The following Example compounds were prepared using the abovementioned procedure:

| Example | R | LC-MS** t$_R$ (min) | [M + H]$^+$ |
|---|---|---|---|
| 122 | N(CH$_3$)-CH$_2$-COOH | 0.50 | 481.38 |
| 123 | HN~~COOH | 0.49 | 481.30 |
| 124 | azetidine-COOH | 0.50 | 493.26 |
| 125 | (S)-proline | 0.53 | 507.29 |
| 126 | pyrrolidine-3-COOH | 0.51 | 507.33 |

Example 124

$^1$H NMR (D$_6$-DMSO): δ 1.06 (t, J=7.3 Hz, 3H), 1.23 (t, J=7.5 Hz, 3H), 2.15 (s, 3H), 2.34 (s, 3H), 2.40-2.48 (m, 5H), 2.72 (q, J=7.5 Hz, 2H), 2.78 (t, J=5.5 Hz, 2H), 3.20-3.28 (m, 1H), 3.30 (t, J=6.5 Hz, 2H), 3.51 (t, J=7.3 Hz, 2H), 3.55 (s, 2H), 3.77 (t, J=5.5 Hz, 2H), 7.47 (s, 1H), 7.79 (s, 2H), 7.90 (s, 1H), 7.92 (s, 1H).

Example 125

$^1$H NMR (D$_6$-DMSO): δ 1.06 (t, J=7.0 Hz, 3H), 1.23 (t, J=7.5 Hz, 3H), 1.71-1.81 (m, 1H), 1.82-1.96 (m, 2H), 2.08-2.14 (m, 1H), 2.15 (s, 3H), 2.36 (s, 3H), 2.42-2.49 (m, 5H), 2.73 (q, J=7.5 Hz, 2H), 2.78-2.86 (m, 1H), 3.10-3.18 (m, 1H), 3.31-3.38 (m, overlapping with H$_2$O), 3.49-3.54 (m, 1H), 3.56 (s, 2H), 3.97-4.05 (m, 2H), 7.47 (s, 1H), 7.81 (s, 2H), 7.91 (s, 1H), 7.93 (s, 1H), 8.17 (s, 1H).

Example 127

N-(3-{4-[5-(4-dimethylaminomethyl-3-methyl-phenyl)-[1,2,4]oxadiazol-3-yl]-2,6-dimethyl-phenoxy}-2-hydroxy-propyl)-2-hydroxy-acetamide The title compound was prepared in analogy to Example 30. LC-MS**: t$_R$=0.50 min; [M+1]$^+$=483.12.

Examples 128 to 138

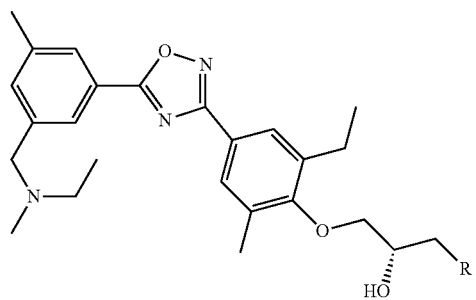

a) To a bi-phasic mixture of 2-ethyl-4-(5-{3-[(ethyl-methyl-amino)-methyl]-5-methyl-phenyl}-[1,2,4]oxadiazol-3-yl)-6-methyl-phenol (1.74 g, 4.76 mmol) in isopropanol (100 mL) and 3M aq. NaOH (23 mL), (R)-epichlorohydrin (4.40 g, 47.6 mmol) is added. The mixture is stirred at rt for 16 h before it is concentrated to about half its volume. The remaining solution is extracted with EA, the org. extract is washed with 1M aq. NaOH followed by water. The washings are extracted back with EA. The combined org. extracts are dried over Na$_2$SO$_4$, filtered and concentrated. The crude product is purified by prep. HPLC (Waters XBridge Prep C18, 50×150 mm ID, 10 μm, eluting with a gradient of MeCN in water containing 0.5% of sat. aq. ammonia) to give ethyl-{3-[3-((S)-3-ethyl-5-methyl-4-oxiranylmethoxy-phenyl)-[1,2,4]oxadiazol-5-yl]-5-methyl-benzyl}-methyl-amine as a colourless resin (950 mg). LC-MS*: t$_R$=1.26 min; [M+1]$^+$=422.23; $^1$H NMR (D$_6$-DMSO): δ 1.06 (t, J=7.0 Hz, 3H), 1.24 (t, J=7.5 Hz, 3H), 2.14 (s, 3H), 2.36 (s, 3H), 2.41-2.48 (m, 5H), 2.69-2.78 (m, 3H), 2.86 (t, J=5.0 Hz, 1H), 3.37-3.42 (m, 1H), 3.54 (s, 2H), 3.69 (dd, J=11.0, 6.8 Hz, 1H), 4.21 (dd, J=11.3, 2.5 Hz, 1H), 7.47 (s, 1H), 7.80 (s, 2H), 7.90 (s, 1H), 7.92 (s, 1H).

b) A solution of the above epoxide (43 mg, 103 μmol), DIPEA (58 mg, 450 μmol) and the appropriate amine, amino acid or amino acid ester (513 μmol) in methanol (2 mL) is stirred at 70° C. for 17 h. The reaction mixture is separated by prep. HPLC (Waters XBridge Prep C18, 50×150 mm ID, 10 μm, eluting with a gradient of MeCN in water containing 0.5% of sat. aq. ammonia) to give the desired products (12-40 mg) as colourless lyophilisates or resins.

The following Example compounds were prepared using the procedures mentioned in steps a) and b) described above:

| Example | R | LC-MS** t$_R$ (min) | [M + H]$^+$ |
|---|---|---|---|
| 128 | HN–/ | 0.48 | 453.20 |
| 129 | HN–\ | 0.50 | 467.18 |
| 130 | HN–\–OH | 0.48 | 483.15 |
| 131 | HN–\–\–OH | 0.48 | 497.33 |
| 132 | N–/ (methyl) | 0.49 | 467.22 |
| 133 | N–\ (methyl) | 0.51 | 481.37 |
| 134 | N–\–OH (methyl) | 0.48 | 497.35 |
| 135 | HN–\–NH$_2$ | 0.49 | 482.30 |
| 136 | HN–\–C(O)–O–Me | 0.51 | 525.26 |
| 137 | N-azetidinyl-COOH | 0.49 | 523.26 |
| 138 | N-pyrrolidinyl-COOH | 0.50 | 537.34 |

Example 129

$^1$H NMR (D$_6$-DMSO): δ 1.04 (t, J=7.3 Hz, 3H), 1.06 (t, J=7.3 Hz, 3H), 1.23 (t, J=7.3 Hz, 3H), 2.14 (s, 3H), 2.36 (s, 3H), 2.41-2.48 (m, 5H), 2.55-2.67 (m, 3H), 2.71-2.79 (m, 3H), 3.54 (s, 2H), 3.75 (dd, J=9.3, 6.0 Hz, 1H), 3.82 (dd, J=9.3, 4.8 Hz, 1H), 3.88-3.96 (m, 1H), 4.99 (br d, J=3.0 Hz, 1H), 7.47 (s, 1H), 7.79 (s, 2H), 7.90 (s, 1H), 7.92 (s, 1H).

Example 132

$^1$H NMR (D$_6$-DMSO): δ 1.06 (t, J=7.3 Hz, 3H), 1.23 (t, J=7.3 Hz, 3H), 2.14 (s, 3H), 2.22 (s, 6H), 2.28-2.35 (m, 1H), 2.36 (s, 3H), 2.41-2.48 (m, 6H), 2.76 (q, J=7.5 Hz, 2H), 3.55 (s, 2H), 3.75 (dd, J=9.5, 5.8 Hz, 1H), 3.82 (dd, J=9.5, 3.8 Hz, 1H), 3.91-3.99 (m, 1H), 4.88 (d, J=4.5 Hz, 1H), 7.47 (s, 1H), 7.79 (s, 2H), 7.90 (s, 1H), 7.92 (s, 1H).

Example 138

$^1$H NMR (D$_6$-DMSO): δ 1.06 (t, J=7.0 Hz, 3H), 1.23 (t, J=7.5 Hz, 3H), 1.95 (q, J=7.0 Hz, 2H), 2.14 (s, 3H), 2.36 (s, 3H), 2.41-2.48 (m, 5H), 2.59 (t, J=6.8 Hz, 1H), 2.67-2.95 (m,

6H), 3.55 (s, 2H), 3.73-3.78 (m, 1H), 3.80-3.86 (m, 1H), 3.92-3.98 (m, 1H), 7.47 (s, 1H), 7.79 (s, 2H), 7.90 (s, 1H), 7.92 (s, 1H).

Examples 139 and 140

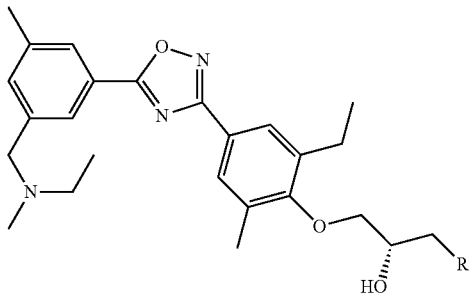

Ethyl-{3-[3-((S)-3-ethyl-5-methyl-4-oxiranylmethoxy-phenyl)-[1,2,4]oxadiazol-5-yl]-5-methyl-benzyl}-methyl-amine (43 mg, 103 µmol) is reacted with the appropriate amino acid ester (513 µmol) as described for Example 136. The material is then dissolved in acetonitrile (1 mL) and 1N aq. NaOH (0.3 mL). The mixture is stirred at rt for 2 h before formic acid (50 µL), followed by sat. aq. ammonia, is added. The mixture is separated by prep. HPLC (Waters XBridge Prep C18, 50×19 mm ID, 10 µm, eluting with a gradient of MeCN in water containing 0.5% of sat. aq. ammonia) to give the desired amino acid derivative as a white lyophilisate.

The compounds of Examples 139 and 140 were prepared using the above-mentioned procedure:

| Example | R | $t_R$ (min) LC-MS* | $[M + H]^+$ |
|---|---|---|---|
| 139 | HN⌒⌒COOH | 0.66 | 511.24 |
| 140 | pyrrolidine-COOH | 0.70 | 537.27 |

Example 140

$^1$H NMR (D$_6$-DMSO): δ 1.06 (t, J=7.0 Hz, 3H), 1.24 (t, J=7.5 Hz, 3H), 1.67-1.78 (m, 1H), 1.83-2.02 (m, 2H), 2.08-2.21 (m, 4H), 2.36 (s, 3H), 2.42-2.48 (m, 5H), 2.75 (q, J=7.5 Hz, 2H), 2.87-2.97 (m, 1H), 3.04-3.11 (m, 1H), 3.14-3.20 (m, 1H), 3.44-3.53 (m, 2H), 3.55 (s, 2H), 3.74-3.88 (m, 2H), 4.07-4.15 (m, 1H), 7.47 (s, 1H), 7.80 (s, 2H), 7.90 (s, 1H), 7.92 (s, 1H).

Examples 141 to 143

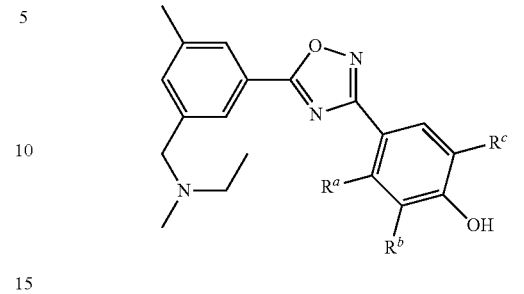

The following Example compounds were prepared by coupling and cyclizing 3-[(ethyl-methyl-amino)-methyl]-5-methyl-benzoic acid (64 mg, 310 µmol) with the appropriate hydroxy-benzamidine (279 µmol) as described for 3-[3-(3-ethyl-4-hydroxy-5-methyl-phenyl)-[1,2,4]oxadiazol-5-yl]-5-methyl-benzaldehyde.

| Example | $R^a$ | $R^b$ | $R^c$ | LC-MS** $t_R$ (min) | $[M + H]^+$ |
|---|---|---|---|---|---|
| 141 | H | CH$_3$ | n-propyl | 1.20 | 380.22 |
| 142 | H | CH$_3$ | Cl | 0.70 | 372.21 |
| 143 | OCH$_3$ | H | H | 0.71 | 354.23 |

Examples 144 to 147

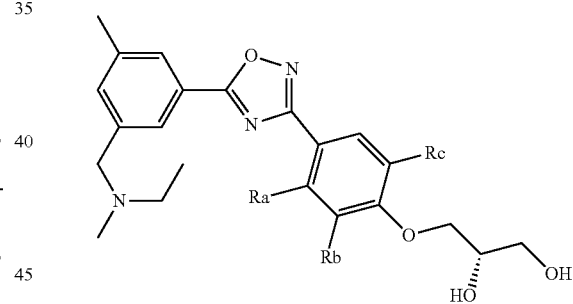

The following Example compounds were prepared by coupling and cyclizing 3-[(ethyl-methyl-amino)-methyl]-5-methyl-benzoic acid (64 mg, 310 µmol) with the appropriate (R)-4-(2,2-dimethyl-[1,3]dioxolan-4-ylmethoxy)-N-hydroxy-benzamidine (279 µmol) as described for 3-[3-(3-ethyl-4-hydroxy-5-methyl-phenyl)-[1,2,4]oxadiazol-5-yl]-5-methyl-benzaldehyde. The acetal protected diol intermediate is cleaved by dissolving the compound in 4M HCl in dioxane and stirring the mixture at rt. The mixture is concentrated and the crude product is purified by prep. HPLC to give the desired compound as a white lyophilisate.

| Example | $R^a$ | $R^b$ | $R^c$ | LC-MS** $t_R$ (min) | $[M + H]^+$ |
|---|---|---|---|---|---|
| 144 | H | CH$_3$ | Cl | 1.02 | 446.15 |
| 145 | H | CH$_3$ | OCH$_3$ | 0.94 | 442.21 |
| 146 | OCH$_3$ | H | H | 0.83 | 428.17 |

Example 146

¹H NMR (D₆-DMSO): δ 1.06 (t, J=7.0 Hz, 3H), 2.14 (s, 3H), 2.41-2.47 (m, 5H), 3.48 (t, J=5.8 Hz, 2H), 3.54 (s, 2H), 3.80-3.87 (m, 1H), 3.90 (s, 3H), 3.99 (dd, J=9.8, 6.0 Hz, 1H), 4.13 (dd, J=10.0, 4.0 Hz, 1H), 4.73 (t, J=5.8 Hz, 1H), 5.02 (d, J=5.0 Hz, 1H), 6.73 (dd, J=8.8, 2.3 Hz, 1H), 6.77 (d, J=2.0 Hz, 1H), 7.45 (s, 1H), 7.86 (s, 1H), 7.89 (s, 1H), 7.93 (d, J=8.5 Hz, 1H).

Examples 147 to 150

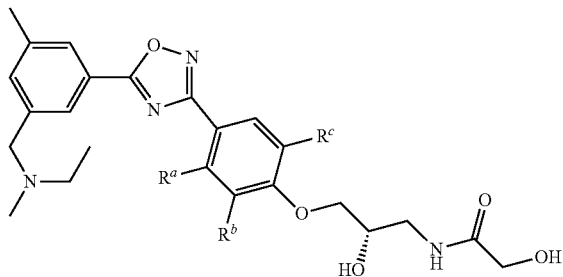

The following Example compounds were prepared by coupling and cyclizing 3-[(ethyl-methyl-amino)-methyl]-5-methyl-benzoic acid (64 mg, 310 µmol) with the appropriate (S)-2-hydroxy-N-{2-hydroxy-3-[4-(N-hydroxycarbamimidoyl)-phenoxy]-propyl}-acetamide (279 µmol) as described for 3-[3-(3-ethyl-4-hydroxy-5-methyl-phenyl)-[1,2,4]oxadiazol-5-yl]-5-methyl-benzaldehyde.

| Example | $R^a$ | $R^b$ | $R^c$ | LC-MS** $t_R$ (min) | $[M + H]^+$ |
|---|---|---|---|---|---|
| 147 | H | CH₃ | CH₃ | 0.90 | 483.23 |
| 148 | H | CH₃ | Cl | 0.93 | 503.20 |
| 159 | H | CH₃ | OCH₃ | 0.88 | 499.23 |
| 150 | CH₃ | H | H | 0.87 | 469.21 |

Example 147

¹H NMR (D₆-DMSO): δ 1.06 (t, J=7.3 Hz, 3H), 2.14 (s, 3H), 2.34 (s, 6H), 2.41-2.47 (m, 5H), 3.19-3.30 (m, 1H), 3.40-3.48 (m, 1H), 3.54 (s, 2H), 3.73 (dd, J=9.5, 6.0 Hz, 1H), 3.78 (dd, J=9.8, 4.5 Hz, 1H), 3.84 (d, J=5.5 Hz, 2H), 3.92-3.99 (m, 1H), 5.31 (d, J=5.0 Hz, 1H), 5.56 (t, J=5.8 Hz, 1H), 7.47 (s, 1H), 7.71 (t, J=5.8 Hz, 1H), 7.79 (s, 2H), 7.90 (s, 1H), 7.92 (s, 1H).

Example 148

¹H NMR (D₆-DMSO): δ 1.06 (t, J=7.0 Hz, 3H), 2.14 (s, 3H), 2.41 (s, 3H), 2.43-2.47 (m, 5H), 3.21-3.30 (m, 1H), 3.40-3.48 (m, 1H), 3.54 (s, 2H), 3.84 (d, J=5.5 Hz, 2H), 3.86-4.01 (m, 3H), 5.33 (d, J=5.0 Hz, 1H), 5.56 (t, J=5.8 Hz, 1H), 7.48 (s, 1H), 7.71 (t, J=5.8 Hz, 1H), 7.91 (s, 1H), 7.93 (s, 1H), 7.94 (d, J=2.0 Hz, 1H), 7.96 (d, J=2.0 Hz, 1H).

Example 151

3-[2-ethyl-4-(5-{3-[(ethyl-methyl-amino)-methyl]-5-methyl-phenyl}-[1,2,4]oxadiazol-3-yl)-6-methyl-phenoxy]-propan-1-ol 3-bromo-1-propanol (55 mg, 398 µmol) was added to a suspension of 2-ethyl-4-(5-{3-[(ethyl-methyl-amino)-methyl]-5-methyl-phenyl}-[1,2,4]oxadiazol-3-yl)-6-methyl-phenol (97 mg, 265 µmol) and K₂CO₃ (88 mg, 637 µmol) in DMF (2 mL). The mixture was stirred at 60° C. for 3 h before it was filtered. The filtrate was separated by prep. HPLC (XBridge 30×75 mm, eluting with a gradient of MeCN in water containing 0.5% of sat. aq. ammonia) to give the title compound as a colourless resin (67 mg). LC-MS**: $t_R$=0.61 min; [M+1]⁺=424.25; ¹H NMR (D₆-DMSO): δ 1.06 (t, J=7.0 Hz, 3H), 1.23 (t, J=7.3 Hz, 3H), 1.90-1.98 (m, 2H), 2.15 (s, 3H), 2.34 (s, 3H), 2.41-2.49 (m, 5H), 2.71 (q, J=7.3 Hz, 2H), 3.55 (s, 2H), 3.65 (q, J=5.8 Hz, 2H), 3.90 (t, J=6.0 Hz, 2H), 4.55 (t, J=4.8 Hz, 1H), 7.47 (s, 1H), 7.80 (s, 2H), 7.90 (s, 1H), 7.92 (s, 1H).

Example 152

(S)-3-[2-ethyl-4-(5-{3-[(ethyl-methyl-amino)-methyl]-5-methyl-phenyl}-[1,2,4]oxadiazol-3-yl)-6-methyl-phenoxy]-propane-1,2-diol To a solution of 2-ethyl-4-(5-{3-[(ethyl-methyl-amino)-methyl]-5-methyl-phenyl}-[1,2,4]oxadiazol-3-yl)-6-methyl-phenol (99 mg, 271 µmol) in THF (2 mL), PPh₃ (107 mg, 406 µmol) and (R)-2,2-dimethyl-1,3-dioxolane-4-methanol (36 mg, 271 µmol) were added. The mixture was cooled to 0° C. and DEAD (177 mg, 406 µmol, 186 µL of a 40% solution in toluene) was added. Stirring was continued at 0° C. for 10 min, then at rt for 1 h before another portion of PPh₃ (107 mg, 406 µmol) and (R)-2,2-dimethyl-1,3-dioxolane-4-methanol (36 mg, 271 µmol) was added. Stirring was continued for 1 h and the reaction mixture was separated by prep. HPLC. The product containing fraction were combined, evaporated and dissolved in MeCN (1.5 mL) and 1N aq. HCl (0.4 mL). The mixture was stirred at rt for 10 min before it was again separated by prep. HPLC to give the title compound as a colourless resin (27 mg). LC-MS**: $t_R$=0.56 min; [M+1]⁺ = 440.21; ¹H NMR (D₆-DMSO): δ 1.06 (t, J=7.0 Hz, 3H), 1.23 (t, J=7.0 Hz, 3H), 2.15 (s, 3H), 2.36 (s, 3H), 2.42-2.47 (m, 5H), 2.75 (q, J=7.3 Hz, 2H), 3.50 (d, J=4.8 Hz, 2H), 3.56 (s, 2H), 3.72-3.78 (m, 1H), 3.83-3.89 (m, 2H), 7.47 (s, 1H), 7.79 (s, 2H), 7.91 (s, 1H), 8.18 (s, 1H).

Example 153

2-ethyl-4-(5-{3-[(ethyl-methyl-amino)-methyl]-5-methyl-phenyl}-[1,3,4]oxadiazol-2-yl)-6-methyl-phenol a) To a solution of 3-[(ethyl-methyl-amino)-methyl]-5-methyl-benzoic acid (750 mg, 3.62 mmol) in THF (10 mL), DIPEA (940 mg, 7.24 mmol) and PyBOP (1.88 g, 3.62 mmol) was added. The mixture was stirred at rt for 1 h before 4-benzyloxy-3-ethyl-5-methyl-benzoic acid hydrazide (2.06 g, 3.62 mmol) was added. The mixture was stirred at rt for 1 h and was then diluted with EA and washed with sat. aq. NaHCO₃ solution. The org. phase was collected, dried over MgSO₄, filtered and concentrated. The residue was dissolved in THF and Burgess reagent (1.03 g, 4.34 mmol) was added. The mixture was stirred at 110° C. under microwave irradiation for 12 min. The mixture was cooled to rt, diluted with EA and washed with water. The org. phase was separated and concentrated. The crude product is purified by CC on silica gel eluting with DCM:MeOH 9:1 to 5:1 to give {3-[5-(4-benzyloxy-3-ethyl-5-methyl-phenyl)-[1,3,4]oxadiazol-2-yl]-5-methyl-benzyl}-ethyl-methyl-amine as a pale yellow oil (1.48 g). LC-MS: $t_R$=0.96 min; $[M+1]^+$=456.13.

b) To a solution of the above benzyl ether (1.48 g, 3.25 mmol) in THF (10 mL), Pd/C (80 mg, 10% Pd) followed by AcOH (0.5 mL) was added. The slurry was stirred at rt for 2 h under 1 bar of $H_2$. The catalyst was filtered off and the filtrate was concentrated and separated by CC on silica gel eluting with DCM:methanol 4:1 to give the title compound as a colourless oil (1.19 g). LC-MS: $t_R$=0.80 min; $[M+1]^+$=366.13.

Example 154

(S)-1-amino-3-[2-ethyl-4-(5-{3-[(ethyl-methyl-amino)-methyl]-5-methyl-phenyl}-[1,3,4]oxadiazol-2-yl)-6-methyl-phenoxy]-propan-2-ol The title compound was prepared in analogy to Example 128 starting from the compound of Example 153 using (R)-epichlorohydrine in step a) and ammonia in methanol in step b). LC-MS: $t_R$=0.65 min; $[M+1]^+$=439.20.

Example 155

N—{(S)-3-[2-ethyl-4-(5-{3-[(ethyl-methyl-amino)-methyl]-5-methyl-phenyl}-[1,3,4]oxadiazol-2-yl)-6-methyl-phenoxy]-2-hydroxy-propyl}-2-hydroxy-acetamide To a solution of (5)-1-amino-3-[2-ethyl-4-(5-{3-[(ethyl-methyl-amino)-methyl]-5-methyl-phenyl}-[1,3,4]oxadia-zol-2-yl)-6-methyl-phenoxy]-propan-2-ol (214 mg, 488 µmol) in THF (5 mL), DIPEA (91 mg, 732 µmol), HOBt (66 mg, 488 µmol), EDC (94 mg, 488 µmol) and glycolic acid (37 mg, 488 µmol) is added. The mixture is stirred at rt for 1 h before DMF (2 mL) is added. Stirring is continued for 30 min. The mixture is concentrated in vacuo and then separated by prep. HPLC to give the title compound as a colourless oil (38 mg). LC-MS: $t_R$=0.71 min; $[M+1]^+$=497.23.

Example 156

GTPγS Assay to Determine $EC_{50}$ Values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM $MgCl_2$ (Fluka, 63064), 0.1% BSA (Calbiochem, 126609), 1 µM GDP (Sigma, G-7127), 2.5% DMSO (Fluka, 41644), 50 pM $^{35}$5-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of $^{35}$5-GTPγS. After addition of 50 µl of $^{35}$5-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM $Na_2HPO_4/NaH_2PO_4$ (70%/30%), dried, sealed at the bottom and, after addition of 25 µl MicroScint20 (Packard Biosciences, order #6013621), sealed on the top. Membrane-bound $^{35}$S-GTPγS is measured with a TopCount from Packard Biosciences.

$EC_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay.

The $EC_{50}$ values of the compounds of Example 106, 153 and 154 were not measured. With the exception of the compound of Example 1, which shows an $EC_{50}$ value greater than 10 µM, the $EC_{50}$ values of all other exemplified compounds are in the range of 1 to 5340 nM with an average of 248 nM. Agonistic activities, determined according to the method described above, of some compounds of the present invention are displayed in Table 1.

TABLE 1

| Compound of Example | $EC_{50}$ [nM] | Compound of Example | $EC_{50}$ [nM] |
|---|---|---|---|
| 15 | 4.1 | 16 | 2.7 |
| 18 | 3.3 | 19 | 2.2 |
| 21 | 5.6 | 22 | 7.0 |
| 40 | 7.1 | 42 | 5.8 |
| 49 | 3.7 | 50 | 5.3 |
| 51 | 2.4 | 52 | 2.0 |
| 58 | 8.4 | 61 | 3.6 |
| 62 | 3.1 | 71 | 2.1 |
| 72 | 2.3 | 73 | 2.0 |
| 75 | 7.2 | 89 | 22 |
| 100 | 1.6 | 105 | 8.0 |
| 127 | 8.5 | 144 | 2.0 |
| 147 | 2.0 | 148 | 1.3 |

Example 157

Assessment of In Vivo Efficacy

The efficacy of the compounds of formula (I) is assessed by measuring the circulating lymphocytes after oral administration of 3 to 30 mg/kg of a compound of formula (I) to normotensive male Wistar rats. The animals are housed in climate-controlled conditions with a 12 h-light/dark cycle, and have free access to normal rat chow and drinking water.

Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 2 shows the effect on lymphocyte counts 3 h after oral administration of 10 mg/kg of compounds of the present invention to normotensive male Wistar rats as compared to a group of animals treated with vehicle only.

TABLE 2

| Compound of Example | Lymphocyte counts |
|---|---|
| 16 | −62.1% |
| 18 | −63.0% |
| 22 | −61.0% |

TABLE 2-continued

| Compound of Example | Lymphocyte counts |
| --- | --- |
| 53 | −61.0% |
| 99 | −61.0% |

Besides, lymphocyte counts 6 h after oral administration have been measured for 8 of the Example compounds and are in the range of −38% to −63% with an average of −56%.

The invention claimed is:

1. A compound of formula (I)

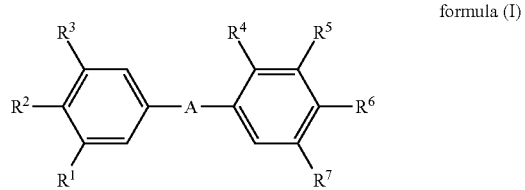

wherein

A represents

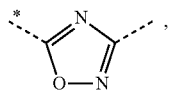

wherein the asterisks indicate the bond that is linked to the phenyl group bearing the substituents $R^1$, $R^2$ and $R^3$;

$R^1$ represents —$CH_2$—$NR^{1a}R^{1b}$, $R^2$ represents hydrogen, and $R^3$ represents hydrogen, $C_{1-4}$ alkyl, or $C_{1-3}$-alkoxy; or $R^1$ represents —$CH_2$—$NR^{1a}R^{1b}$, $R^2$ represents $C_{1-4}$-alkyl or $C_{1-3}$-alkoxy, and $R^3$ represents hydrogen or methyl; or $R^1$ represents hydrogen, $C_{1-4}$-alkyl or $C_{1-3}$-alkoxy, $R^2$ represents —$CH_2$—$NR^{2a}R^{2b}$, and $R^3$ represents hydrogen or methyl;

$R^{1a}$ represents $C_{1-4}$-alkyl, $R^{1b}$ represents hydrogen, or $C_{1-2}$-alkyl, or $R^{1a}$ and $R^{1b}$ together with the nitrogen atom to which they are attached form a pyrrolidine ring;

$R^{2a}$ represents $C_{1-4}$-alkyl, $R^{2b}$ represents hydrogen, or $C_{1-2}$-alkyl, or $R^{2a}$ and $R^2$, together with the nitrogen atom to which they are attached form a pyrrolidine ring;

$R^4$ represents hydrogen, methyl, methoxy or chloro;

$R^5$ represents hydrogen, $C_{1-3}$-alkyl, methoxy, fluoro or chloro;

$R^6$ represents 2,3-dihydroxypropyl, —$CH_2$—$(CH_2)_n$—$NR^{61}R^{62}$, —$CH_2$—$(CH_2)_n$—$NHCOR^{64}$, —$CH_2$—$(CH_2)_n$—$NHSO_2R^{63}$, —$CH_2$—$CH_2$—COOH, —$CH_2$—$CH_2$—$CONR^{61}R^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, —$CH_2$—CH(OH)—$CH_2$—$NR^{61}R^{62}$, —$CH_2$—CH(OH)—$CH_2$—$NHCOR^{64}$, —$CH_2$—CH(OH)—$CH_2$—$NHSO_2R^{63}$, hydroxy, hydroxy-$C_{2-4}$-alkoxy, 1-hydroxymethyl-2-hydroxy-ethoxy, 2,3-dihydroxypropoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —$OCH_2$—CH(OH)—$CH_2$—$NR^{61}R^{62}$, —$OCH_2$—CH(OH)—$CH_2$—$NHCOR^{64}$, —$OCH_2$—CH(OH)—$CH_2$—$NHSO_2R^{63}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, —$NR^{61}R^{62}$, —NHCO—$R^{64}$;

$R^{61}$ represents hydrogen, methyl, ethyl, 2-hydroxyethyl, 3-hydroxypropyl, 2-aminoethyl, 2-($C_{1-4}$-alkylamino)ethyl, 2-(di-($C_{1-4}$-alkyl)amino)ethyl, carboxymethyl, ($C_{1-4}$-alkylcarboxy)methyl, 2-carboxyethyl, or 2-($C_{1-4}$-alkylcarboxy)ethyl;

$R^{62}$ represents hydrogen or methyl;

$R^{63}$ represents methyl, ethyl, methylamino, or dimethylamino;

$R^{64}$ represents hydroxymethyl, 2-hydroxyethyl, methylaminomethyl, dimethylaminomethyl, or 2-methylamino-ethyl;

m represents the integer 1 or 2;

n represents 0, 1 or 2; and $R^7$ represents hydrogen, or $C_{1-2}$-alkyl;

or a pharmaceutically acceptable salt thereof.

2. A compound according to claim 1, wherein $R^1$ represents —$CH_2$—$NR^{1a}R^{1b}$, $R^2$ represents hydrogen, and $R^3$ represents $C_{1-2}$-alkyl;

or a pharmaceutically acceptable salt thereof.

3. A compound according to claim 1, wherein $R^1$ represents hydrogen or $C_{1-4}$-alkyl, $R^2$ represents —$CH_2$—$NR^{2a}R^{2b}$, and $R^3$ represents hydrogen;

or a pharmaceutically acceptable salt thereof.

4. A compound according to claim 1, wherein $R^4$ represents hydrogen, $R^5$ represents $C_{1-3}$-alkyl and $R^7$ represents $C_{1-2}$-alkyl;

or a pharmaceutically acceptable salt thereof.

5. A compound according to claim 1, wherein $R^6$ represents —$OCH_2$—CH(OH)—$CH_2$—$NHCOR^{64}$;

or a pharmaceutically acceptable salt thereof.

6. A compound according to claim 5, wherein the absolute configuration of the OH group in the side chain $R^6$ is (S), i.e. as represented below:

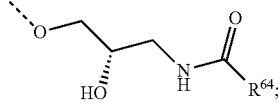

or a pharmaceutically acceptable salt thereof.

7. A compound according to claim 1 selected from the group consisting of:

N—((S)-3-{4-[5-(3-dimethylaminomethyl-5-methyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-[(ethyl-methyl-amino)-methyl]-5-methyl-phenyl}-[1,2,4]oxadiazol-3-yl)-6-methyl-phenoxy]-2-hydroxy-propyl}-2-hydroxy-acetamide;

N—{(S)-3-[2-ethyl-6-methyl-4-(5-{3-methyl-5-[(methyl-propyl-amino)-methyl]-phenyl}-[1,2,4]oxadiazol-3-yl)-phenoxy]-2-hydroxy-propyl}-2-hydroxy-acetamide;

N—{(S)-3-[4-(5-{3-[(butyl-methyl-amino)-methyl]-5-methyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{3-[(isobutyl-methyl-amino)-methyl]-5-methyl-phenyl}-[1,2,4]oxadiazol-3-yl)-6-methyl-phenoxy]-2-hydroxy-propyl}-2-hydroxy-acetamide;

N—((S)-3-{4-[5-(3-Diethylaminomethyl-5-methyl-phenyl)-[1,2,4]oxadiazol-3-yl]-2-ethyl-6-methyl-phenoxy}-2-hydroxy-propyl)-2-hydroxy-acetamide;

N—{(S)-3-[4-(5-{3-[(butyl-ethyl-amino)-methyl]-5-methyl-phenyl}-[1,2,4]oxadiazol-3-yl)-2-ethyl-6-methyl-phenoxy]-2-hydroxy-propyl}-2-hydroxy-acetamide;

N—((S)-3-{2-ethyl-6-methyl-4-[5-(3-methyl-5-pyrrolidin-1-ylmethyl-phenyl)-[1,2,4]oxadiazol-3-yl]-phenoxy}-2-hydroxy-propyl)-2-hydroxy-acetamide;

N—{(S)-3-[4-(5-{4-[(butyl-ethyl-amino)-methyl]-3-methyl-phenyl}-[1,2,4]oxadiazol-3-yl)-2,6-dimethyl-phenoxy]-2-hydroxy-propyl}-2-hydroxy-acetamide;

N—((S)-3-{4-[5-(4-dimethylaminomethyl-3-methyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{4-[(ethyl-methyl-amino)-methyl]-3-methyl-phenyl}-[1,2,4]oxadiazol-3-yl)-6-methyl-phenoxy]-2-hydroxy-propyl}-2-hydroxy-acetamide;

N—{(S)-3-[4-(5-{4-[(butyl-methyl-amino)-methyl]-3-methyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{4-[(isobutyl-methyl-amino)-methyl]-3-methyl-phenyl}-[1,2,4]oxadiazol-3-yl)-6-methyl-phenoxy]-2-hydroxy-propyl}-2-hydroxy-acetamide; and N—((S)-3-{4-[5-(4-diethylaminomethyl-3-methyl-phenyl)-[1,2,4]oxadiazol-3-yl]-2-ethyl-6-methyl-phenoxy}-2-hydroxy-propyl)-2-hydroxy-acetamide or a pharmaceutically acceptable salt thereof.

8. A compound according to claim 1 selected from the group consisting of:

N—((S)-3-{2-ethyl-4-[5-(3-ethyl-5-propylaminomethyl-phenyl)-[1,2,4]oxadiazol-3-yl]-6-methyl-phenoxy}-2-hydroxy-propyl)-2-hydroxy-acetamide;

N—((S)-3-{4-[5-(3-butylaminomethyl-5-ethyl-phenyl)-[1,2,4]oxadiazol-3-yl]-2-ethyl-6-methyl-phenoxy}-2-hydroxy-propyl)-2-hydroxy-acetamide;

N—[(S)-3-(2-ethyl-4-{5-[3-ethyl-5-(isobutylamino-methyl)-phenyl]-[1,2,4]oxadiazol-3-yl}-6-methyl-phenoxy)-2-hydroxy-propyl]-2-hydroxy-acetamide;

N—((S)-3-{4-[5-(3-dimethylaminomethyl-5-ethyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-ethyl-5-[(ethyl-methyl-amino)-methyl]-phenyl}-[1,2,4]oxadiazol-3-yl)-6-methyl-phenoxy]-2-hydroxy-propyl}-2-hydroxy-acetamide;

N—{(S)-3-[2-ethyl-4-(5-{3-ethyl-5-[(methyl-propyl-amino)-methyl]-phenyl}-[1,2,4]oxadiazol-3-yl)-6-methyl-phenoxy]-2-hydroxy-propyl}-2-hydroxy-acetamide;

N—{(S)-3-[4-(5-{3-[(butyl-methyl-amino)-methyl]-5-ethyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{3-ethyl-5-[(isobutyl-methyl-amino)-methyl]-phenyl}-[1,2,4]oxadiazol-3-yl)-6-methyl-phenoxy]-2-hydroxy-propyl}-2-hydroxy-acetamide;

N—((S)-3-{4-[5-(3-diethylaminomethyl-5-ethyl-phenyl)-[1,2,4]oxadiazol-3-yl]-2-ethyl-6-methyl-phenoxy}-2-hydroxy-propyl)-2-hydroxy-acetamide;

N—((S)-3-{2-ethyl-4-[5-(3-ethyl-5-pyrrolidin-1-ylmethyl-phenyl)-[1,2,4]oxadiazol-3-yl]-6-methyl-phenoxy}-2-hydroxy-propyl)-2-hydroxy-acetamide;

N—((S)-3-{2-ethyl-6-methyl-4-[5-(3-propyl-5-propylaminomethyl-phenyl)-[1,2,4]oxadiazol-3-yl]-phenoxy}-2-hydroxy-propyl)-2-hydroxy-acetamide;

N—((S)-3-{4-[5-(3-butylaminomethyl-5-propyl-phenyl)-[1,2,4]oxadiazol-3-yl]-2-ethyl-6-methyl-phenoxy}-2-hydroxy-propyl)-2-hydroxy-acetamide;

N—[(S)-3-(2-ethyl-4-{5-[3-(isobutylamino-methyl)-5-propyl-phenyl]-[1,2,4]oxadiazol-3-yl}-6-methyl-phenoxy)-2-hydroxy-propyl]-2-hydroxy-acetamide;

N—((S)-3-{4-[5-(3-dimethylaminomethyl-5-propyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-[(ethyl-methyl-amino)-methyl]-5-propyl-phenyl}-[1,2,4]oxadiazol-3-yl)-6-methyl-phenoxy]-2-hydroxy-propyl}-2-hydroxy-acetamide;

N—{(S)-3-[2-ethyl-6-methyl-4-(5-{3-[(methyl-propyl-amino)-methyl]-5-propyl-phenyl}-[1,2,4]oxadiazol-3-yl)-phenoxy]-2-hydroxy-propyl}-2-hydroxy-acetamide;

N—{(S)-3-[4-(5-{3-[(butyl-methyl-amino)-methyl]-5-propyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{3-[(isobutyl-methyl-amino)-methyl]-5-propyl-phenyl}-[1,2,4]oxadiazol-3-yl)-6-methyl-phenoxy]-2-hydroxy-propyl}-2-hydroxy-acetamide;

N—((S)-3-{4-[5-(3-diethylaminomethyl-5-propyl-phenyl)-[1,2,4]oxadiazol-3-yl]-2-ethyl-6-methyl-phenoxy}-2-hydroxy-propyl)-2-hydroxy-acetamide;

N—((S)-3-{2-ethyl-6-methyl-4-[5-(3-propyl-5-pyrrolidin-1-ylmethyl-phenyl)-[1,2,4]oxadiazol-3-yl]-phenoxy}-2-hydroxy-propyl)-2-hydroxy-acetamide;

N—((S)-3-{2-ethyl-4-[5-(3-isopropyl-5-propylaminomethyl-phenyl)-[1,2,4]oxadiazol-3-yl]-6-methyl-phenoxy}-2-hydroxy-propyl)-2-hydroxy-acetamide;

N—((S)-3-{4-[5-(3-butylaminomethyl-5-isopropyl-phenyl)-[1,2,4]oxadiazol-3-yl]-2-ethyl-6-methyl-phenoxy}-2-hydroxy-propyl)-2-hydroxy-acetamide;

N—[(S)-3-(2-ethyl-4-{5-[3-(isobutylamino-methyl)-5-isopropyl-phenyl]-[1,2,4]oxadiazol-3-yl}-6-methyl-phenoxy)-2-hydroxy-propyl]-2-hydroxy-acetamide;

N—((S)-3-{4-[5-(3-dimethylaminomethyl-5-isopropyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-[(ethyl-methyl-amino)-methyl]-5-isopropyl-phenyl}-[1,2,4]oxadiazol-3-yl)-6-methyl-phenoxy]-2-hydroxy-propyl}-2-hydroxy-acetamide;

N—{(S)-3-[2-ethyl-4-(5-{3-isopropyl-5-[(methyl-propyl-amino)-methyl]-phenyl}-[1,2,4]oxadiazol-3-yl)-6-methyl-phenoxy]-2-hydroxy-propyl}-2-hydroxy-acetamide;

N—{(S)-3-[4-(5-{3-[(butyl-methyl-amino)-methyl]-5-isopropyl-phenyl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{3-[(isobutyl-methyl-amino)-methyl]-5-isopropyl-phenyl}-[1,2,4]oxadiazol-3-yl)-6-methyl-phenoxy]-2-hydroxy-propyl}-2-hydroxy-acetamide;

N—((S)-3-{4-[5-(3-diethylaminomethyl-5-isopropyl-phenyl)-[1,2,4]oxadiazol-3-yl]-2-ethyl-6-methyl-phenoxy}-2-hydroxy-propyl)-2-hydroxy-acetamide;

N—((S)-3-{2-ethyl-4-[5-(3-isopropyl-5-pyrrolidin-1-yl-methyl-phenyl)-[1,2,4]oxadiazol-3-yl]-6-methyl-phenoxy}-2-hydroxy-propyl)-2-hydroxy-acetamide;

N—((S)-3-{4-[5-(4-dimethylaminomethyl-3-ethyl-phenyl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{3-ethyl-4-[(ethyl-methyl-amino)-methyl]-phenyl}-[1,2,4]oxadiazol-3-yl)-6-methyl-phenoxy]-2-hydroxy-propyl}-2-hydroxy-acetamide;

N—{(S)-3-[2-ethyl-4-(5-{3-ethyl-4-[(isobutyl-methyl-amino)-methyl]-phenyl}-[1,2,4]oxadiazol-3-yl)-6-methyl-phenoxy]-2-hydroxy-propyl}-2-hydroxy-acetamide;

N—((S)-3-{2-ethyl-4-[5-(3-ethyl-4-pyrrolidin-1-ylmethyl-phenyl)-[1,2,4]oxadiazol-3-yl]-6-methyl-phenoxy}-2-hydroxy-propyl)-2-hydroxy-acetamide;

N—((S)-3-{4-[5-(4-dimethylaminomethyl-3-methyl-phenyl)-[1,2,4]oxadiazol-3-yl]-2,6-dimethyl-phenoxy}-2-hydroxy-propyl)-2-hydroxy-acetamide;

(S)-3-[2-chloro-4-(5-{3-[(ethyl-methyl-amino)-methyl]-5-methyl-phenyl}-[1,2,4]oxadiazol-3-yl)-6-methyl-phenoxy]-propane-1,2-diol;

N—{(S)-3-[4-(5-{3-[(ethyl-methyl-amino)-methyl]-5-methyl-phenyl}-[1,2,4]oxadiazol-3-yl)-2,6-dimethyl-phenoxy]-2-hydroxy-propyl}-2-hydroxy-acetamide;

N—{(S)-3-[2-chloro-4-(5-{3-[(ethyl-methyl-amino)-methyl]-5-methyl-phenyl}-[1,2,4]oxadiazol-3-yl)-6-methyl-phenoxy]-2-hydroxy-propyl}-2-hydroxy-acetamide;

N—{(S)-3-[4-(5-{3-[(ethyl-methyl-amino)-methyl]-5-methyl-phenyl}-[1,2,4]oxadiazol-3-yl)-2-methoxy-6-methyl-phenoxy]-2-hydroxy-propyl}-2-hydroxy-acetamide; and (S)-3-[2-ethyl-4-(5-{3-[(ethyl-methyl-amino)-methyl]-5-methyl-phenyl}-[1,2,4]oxadiazol-3-yl)-6-methyl-phenoxy]-propane-1,2-diol, or a pharmaceutically acceptable salt thereof.

9. A pharmaceutical composition comprising a compound according to claim 1, or a pharmaceutically acceptable salt thereof, and a pharmaceutically acceptable carrier.

10. A method for the treatment or prophylaxis of diseases or disorders associated with an activated immune system, comprising administering to a patient in need thereof an effective amount of a compound according to claim 1 or a pharmaceutically acceptable salt thereof wherein said disease or disorder is selected from the group consisting of rejection of transplanted organs, kidney, liver, heart, lung, pancreas, cornea, and skin.

* * * * *